US012233033B2

(12) United States Patent
Went et al.

(10) Patent No.: US 12,233,033 B2
(45) Date of Patent: *Feb. 25, 2025

(54) AMANTADINE COMPOSITIONS, PREPARATIONS THEREOF, AND METHODS OF USE

(71) Applicant: Adamas Pharma, LLC, Emeryville, CA (US)

(72) Inventors: Gregory T. Went, San Francisco, CA (US); Timothy J. Fultz, Jasper, GA (US); Sangita Ghosh, Foster City, CA (US); Natalie McClure, Portola Valley, CA (US)

(73) Assignee: Adamas Pharma, LLC, Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/339,618

(22) Filed: Jun. 4, 2021

(65) Prior Publication Data

US 2022/0117914 A1   Apr. 21, 2022

Related U.S. Application Data

(60) Continuation of application No. 16/677,431, filed on Nov. 7, 2019, now Pat. No. 11,065,213, which is a division of application No. 16/409,554, filed on May 10, 2019, now Pat. No. 11,077,073, which is a continuation of application No. PCT/US2018/047754, filed on Aug. 23, 2018.

(60) Provisional application No. 62/549,921, filed on Aug. 24, 2017.

(51) Int. Cl.
*A61K 31/136* (2006.01)
*A61K 9/00* (2006.01)
*A61K 9/50* (2006.01)
*A61K 31/13* (2006.01)
*A61P 25/16* (2006.01)
*A61P 25/28* (2006.01)

(52) U.S. Cl.
CPC .......... *A61K 31/136* (2013.01); *A61K 9/0053* (2013.01); *A61K 9/501* (2013.01); *A61K 9/5015* (2013.01); *A61K 9/5026* (2013.01); *A61K 9/5031* (2013.01); *A61K 9/5042* (2013.01); *A61K 9/5047* (2013.01); *A61K 9/5078* (2013.01); *A61K 31/13* (2013.01); *A61P 25/16* (2018.01); *A61P 25/28* (2018.01)

(58) Field of Classification Search
None
See application file for complete search history.

(56) References Cited

U.S. PATENT DOCUMENTS

| | | |
|---|---|---|
| 4,606,909 A | 8/1986 | Bechgaard et al. |
| 5,190,763 A | 3/1993 | Edgren et al. |
| 5,213,808 A | 5/1993 | Bar-Shalom et al. |
| 5,358,721 A | 10/1994 | Guittard et al. |
| 5,378,474 A | 1/1995 | Morella et al. |
| 5,382,601 A | 1/1995 | Nurnberg et al. |
| 5,849,800 A | 12/1998 | Smith |
| 6,194,000 B1 | 2/2001 | Smith et al. |
| 6,217,905 B1 | 4/2001 | Edgren et al. |
| 6,290,990 B1 | 9/2001 | Grabowski et al. |
| 6,372,255 B1 | 4/2002 | Saslawski et al. |
| 6,569,463 B2 | 5/2003 | Patel et al. |
| 7,211,275 B2 | 5/2007 | Ying et al. |
| 7,619,007 B2 | 11/2009 | Went et al. |
| 7,718,677 B2 | 5/2010 | Quik et al. |
| 8,039,009 B2 | 10/2011 | Rastogi et al. |
| 8,058,291 B2 | 11/2011 | Went et al. |
| 8,168,209 B2 | 5/2012 | Went et al. |
| 8,173,708 B2 | 5/2012 | Went et al. |
| 8,247,438 B2 | 8/2012 | Elkashef |
| 8,252,331 B2 | 8/2012 | Meyer et al. |
| 8,263,125 B2 | 9/2012 | Vaya et al. |
| 8,268,352 B2 | 9/2012 | Vaya et al. |
| 8,283,379 B2 | 10/2012 | Went et al. |
| 8,293,794 B2 | 10/2012 | Went et al. |
| 8,313,770 B2 | 11/2012 | Pathak et al. |
| 8,329,752 B2 | 12/2012 | Went et al. |
| 8,338,485 B2 | 12/2012 | Went et al. |

(Continued)

FOREIGN PATENT DOCUMENTS

| | | |
|---|---|---|
| AU | 2002323873 B2 | 11/2006 |
| CA | 2323805 A1 | 9/1999 |

(Continued)

OTHER PUBLICATIONS

U.S. Appl. No. 17/848,265, filed Jun. 23, 2022, by Went et al. (Copy not attached).
U.S. Appl. No. 18/160,961, filed Jan. 27, 2023, by Went et al. (Copy not attached).
Aarsland et al. (2002). "Donepezil for cognitive impairment in Parkinson's disease: a randomised controlled study," J Neurol Neurosurg Psychiatry 72:708-712.
Abou, Z. et al. (2009). "Gait apraxia in multiple sclerosis," Can J Neurol Sci. 36:562-565.
Adamas Pharmaceuticals Press Release (2009). "Adamas Pharmaceuticals raise $40 Million in Series D Financing", 3 pages.

(Continued)

*Primary Examiner* — H. Sarah Park
(74) *Attorney, Agent, or Firm* — Cooley LLP

(57) ABSTRACT

Provided herein are oral pharmaceutical compositions comprising amantadine, or a pharmaceutically acceptable salt thereof, and a pharmaceutically acceptable excipient, and which have a low level of organic solvent. Provided are also methods of orally administrating a composition comprising amantadine, or a pharmaceutically acceptable salt thereof, to a subject, which has reduced gastrointestinal side effects or sleep disturbances. Further provided are extended release oral compositions comprising amantadine, or a pharmaceutically acceptable salt thereof, that are suitable for once daily administration.

34 Claims, 6 Drawing Sheets

(56) References Cited

U.S. PATENT DOCUMENTS

| | | |
|---|---|---|
| 8,338,486 B2 | 12/2012 | Went et al. |
| 8,357,397 B2 | 1/2013 | Bouwstra et al. |
| 8,362,085 B2 | 1/2013 | Went et al. |
| 8,389,008 B2 | 3/2013 | Baichwal et al. |
| 8,389,578 B2 | 3/2013 | Went et al. |
| 8,426,472 B2 | 4/2013 | Went et al. |
| 8,574,626 B2 | 11/2013 | Vergez et al. |
| 8,580,858 B2 | 11/2013 | Went et al. |
| 8,598,233 B2 | 12/2013 | Went et al. |
| 8,741,343 B2 | 6/2014 | Went et al. |
| 8,796,337 B2 | 8/2014 | Went et al. |
| 8,889,740 B1 | 11/2014 | Went et al. |
| 8,895,614 B2 | 11/2014 | Went et al. |
| 8,895,615 B1 | 11/2014 | Went et al. |
| 8,895,616 B1 | 11/2014 | Went et al. |
| 8,895,617 B1 | 11/2014 | Went et al. |
| 8,895,618 B1 | 11/2014 | Went et al. |
| 8,895,662 B2 | 11/2014 | Yang et al. |
| 8,920,837 B2 | 12/2014 | Pilgaonkar et al. |
| 8,987,333 B2 | 3/2015 | Went et al. |
| 9,072,697 B2 | 7/2015 | Went et al. |
| 9,867,791 B2 | 1/2018 | Went et al. |
| 9,867,792 B2 | 1/2018 | Went et al. |
| 9,867,793 B2 | 1/2018 | Went et al. |
| 9,877,933 B2 | 1/2018 | Went et al. |
| 10,154,971 B2 | 12/2018 | Went et al. |
| 10,646,456 B2 | 5/2020 | Went et al. |
| 11,065,213 B2 | 7/2021 | Went et al. |
| 11,077,073 B2 | 8/2021 | Went et al. |
| 11,197,835 B2 | 12/2021 | Went et al. |
| 11,903,908 B2 | 2/2024 | Went et al. |
| 2001/0031278 A1 | 10/2001 | Oshlack et al. |
| 2002/0071863 A1 | 6/2002 | Dong et al. |
| 2003/0045577 A1 | 3/2003 | Madhat |
| 2003/0082230 A1 | 5/2003 | Baichwal et al. |
| 2003/0158154 A1 | 8/2003 | Fleshner-Barak |
| 2004/0087658 A1 | 5/2004 | Moebius |
| 2004/0102525 A1 | 5/2004 | Kozachuk |
| 2005/0119249 A1 | 6/2005 | Buntinx |
| 2005/0245460 A1 | 11/2005 | Meyerson et al. |
| 2005/0267176 A1 | 12/2005 | Barberich |
| 2006/0024366 A1 | 2/2006 | Hirsh et al. |
| 2006/0063810 A1 | 3/2006 | Vergez et al. |
| 2006/0142398 A1 | 6/2006 | Went et al. |
| 2006/0159763 A1 | 7/2006 | Meyer et al. |
| 2006/0189694 A1 | 8/2006 | Went et al. |
| 2006/0252788 A1 | 11/2006 | Went et al. |
| 2007/0104778 A1 | 5/2007 | Zeng et al. |
| 2008/0057123 A1 | 3/2008 | Grenier et al. |
| 2008/0089861 A1 | 4/2008 | Went et al. |
| 2008/0227743 A1 | 9/2008 | Nguyen et al. |
| 2008/0248107 A1 | 10/2008 | Pilgaonkar et al. |
| 2008/0260825 A1 | 10/2008 | Quik et al. |
| 2008/0274061 A1 | 11/2008 | Schollmayer et al. |
| 2008/0279819 A1 | 11/2008 | Went et al. |
| 2009/0169587 A1 | 7/2009 | Baichwal et al. |
| 2009/0215840 A1 | 8/2009 | Elkashef |
| 2009/0247481 A1 | 10/2009 | Nguyen et al. |
| 2010/0004251 A1 | 1/2010 | Barberich et al. |
| 2010/0221328 A1 | 9/2010 | Wertz et al. |
| 2010/0239635 A1 | 9/2010 | McClain et al. |
| 2010/0266684 A1 | 10/2010 | Went et al. |
| 2011/0021419 A1 | 1/2011 | Zimmer et al. |
| 2011/0053981 A1 | 3/2011 | Ieni et al. |
| 2011/0077276 A1 | 3/2011 | Quik et al. |
| 2011/0142905 A1 | 6/2011 | Bar-Shalom et al. |
| 2011/0189273 A1* | 8/2011 | Went ............... A61K 9/5015 424/458 |
| 2011/0287094 A1 | 11/2011 | Penhasi et al. |
| 2012/0045506 A1 | 2/2012 | Baer et al. |
| 2012/0045508 A9 | 2/2012 | Went et al. |
| 2012/0064167 A1 | 3/2012 | Hall et al. |
| 2012/0288560 A1 | 11/2012 | Went et al. |
| 2013/0022676 A1 | 1/2013 | Mullen et al. |
| 2013/0059008 A1 | 3/2013 | Atkinson et al. |
| 2013/0115249 A1 | 5/2013 | Vergez et al. |
| 2013/0165517 A1 | 6/2013 | Went et al. |
| 2013/0165527 A1 | 6/2013 | Went et al. |
| 2013/0236544 A1 | 9/2013 | Bhagwatwar et al. |
| 2014/0134243 A1 | 5/2014 | Went et al. |
| 2014/0135529 A1 | 5/2014 | Went et al. |
| 2014/0179797 A1 | 6/2014 | Went et al. |
| 2014/0193490 A1 | 7/2014 | Schoenhard |
| 2014/0242163 A1 | 8/2014 | Went et al. |
| 2014/0323582 A1 | 10/2014 | Went et al. |
| 2014/0336266 A1 | 11/2014 | Went et al. |
| 2014/0343152 A1 | 11/2014 | Went et al. |
| 2014/0343153 A1 | 11/2014 | Went et al. |
| 2014/0343154 A1 | 11/2014 | Went et al. |
| 2014/0343163 A1 | 11/2014 | Went et al. |
| 2014/0343164 A1 | 11/2014 | Went et al. |
| 2014/0356425 A1 | 12/2014 | Went et al. |
| 2015/0045438 A1 | 2/2015 | Went et al. |
| 2015/0045439 A1 | 2/2015 | Went et al. |
| 2015/0045446 A1 | 2/2015 | Went et al. |
| 2015/0045447 A1 | 2/2015 | Went et al. |
| 2015/0045448 A1 | 2/2015 | Went et al. |
| 2015/0051292 A1 | 2/2015 | Went et al. |
| 2015/0057355 A1 | 2/2015 | Went et al. |
| 2015/0087721 A1 | 3/2015 | Went et al. |
| 2015/0119465 A1 | 4/2015 | Went et al. |
| 2015/0126605 A1 | 5/2015 | Went et al. |
| 2015/0126612 A1 | 5/2015 | Went et al. |
| 2015/0150991 A1 | 6/2015 | Pilgaonkar et al. |
| 2015/0157579 A1 | 6/2015 | Gregory et al. |
| 2015/0297537 A1 | 10/2015 | Went et al. |
| 2016/0151307 A1 | 6/2016 | Went et al. |
| 2016/0220545 A1 | 8/2016 | Went et al. |
| 2016/0228388 A1 | 8/2016 | Went et al. |
| 2016/0243035 A1 | 8/2016 | Went et al. |
| 2016/0243058 A1 | 8/2016 | Went et al. |
| 2016/0243093 A1 | 8/2016 | Went et al. |
| 2016/0243094 A1 | 8/2016 | Went et al. |
| 2016/0243095 A1 | 8/2016 | Went et al. |
| 2016/0250149 A1 | 9/2016 | Went et al. |
| 2016/0250161 A1 | 9/2016 | Went et al. |
| 2016/0256413 A1 | 9/2016 | Went et al. |
| 2016/0256414 A1 | 9/2016 | Went et al. |
| 2016/0263052 A1 | 9/2016 | Went et al. |
| 2016/0263053 A1 | 9/2016 | Went et al. |
| 2016/0263054 A1 | 9/2016 | Went et al. |
| 2016/0263055 A1 | 9/2016 | Went et al. |
| 2016/0263056 A1 | 9/2016 | Went et al. |
| 2016/0263057 A1 | 9/2016 | Went et al. |
| 2016/0263058 A1 | 9/2016 | Went et al. |
| 2017/0056340 A1 | 3/2017 | Went et al. |
| 2017/0151185 A1 | 6/2017 | Went et al. |
| 2017/0151186 A1 | 6/2017 | Went et al. |
| 2017/0151187 A1 | 6/2017 | Went et al. |
| 2017/0151188 A1 | 6/2017 | Went et al. |
| 2017/0151189 A1 | 6/2017 | Went et al. |
| 2017/0151190 A1 | 6/2017 | Went et al. |
| 2017/0281565 A1 | 10/2017 | Went et al. |
| 2018/0253914 A1 | 9/2018 | Mueller |
| 2018/0263928 A1 | 9/2018 | Went et al. |
| 2019/0008799 A1 | 1/2019 | Went et al. |
| 2019/0328684 A1 | 10/2019 | Went et al. |
| 2021/0251919 A1 | 8/2021 | Went et al. |
| 2022/0211641 A1 | 7/2022 | Went et al. |

FOREIGN PATENT DOCUMENTS

| | | |
|---|---|---|
| CN | 1086708 A | 5/1994 |
| CN | 102883601 A | 1/2013 |
| EP | 1 542 660 B1 | 1/2011 |
| EP | 2 506 709 A2 | 10/2012 |
| EP | 2 965 753 A1 | 1/2016 |
| JE | P-2 623 099 A1 | 8/2013 |
| JP | 2008-520736 A | 6/2008 |
| JP | 2013-512919 A | 4/2013 |
| WO | WO-94/03158 A1 | 2/1994 |
| WO | WO-00/00197 A1 | 1/2000 |
| WO | WO-03/101458 A1 | 12/2003 |
| WO | WO-2004/012741 A1 | 2/2004 |

(56) References Cited

FOREIGN PATENT DOCUMENTS

| WO | WO-2004/037190 A2 | 5/2004 |
|---|---|---|
| WO | WO-2004/037190 A3 | 5/2004 |
| WO | WO-2004/037234 A2 | 5/2004 |
| WO | WO-2004/037234 A3 | 5/2004 |
| WO | WO-2004/087116 A2 | 10/2004 |
| WO | WO-2004/087116 A3 | 10/2004 |
| WO | WO-2005/072705 A1 | 8/2005 |
| WO | WO-2005/079779 A1 | 9/2005 |
| WO | WO-2005/084655 A1 | 9/2005 |
| WO | WO-2006/058059 A2 | 6/2006 |
| WO | WO-2006/058059 A3 | 6/2006 |
| WO | WO-2006/058236 A2 | 6/2006 |
| WO | WO-2006/058236 A3 | 6/2006 |
| WO | WO-2007/022255 A2 | 2/2007 |
| WO | WO-2007/022255 A3 | 2/2007 |
| WO | WO-2011/069010 A2 | 6/2011 |
| WO | WO-2011/069010 A3 | 6/2011 |
| WO | WO-2014/204933 A1 | 12/2014 |
| WO | WO-2016/073510 A1 | 5/2016 |

OTHER PUBLICATIONS

Adamas Pharmaceuticals press release (2013). "Adamas Pharmaceuticals to Report Positive Phase 2/3 Results for ADS-5102 for the Treatment of Levodopa-Induced Dyskinesia in Parkinson's Disease," 2 total pages.

Adamas Pharmaceuticals, Inc. Press Release, Adamas announces FDA approval of Gocovri as first and only medication for the treatment of dyskinesia in parkinson's disease patients, 4 total pages.

Alisky et al. (2003). "A case history illustrating how extended release cholinesterase inhibitors could improve management of Alzheimer's disease," J Alzheimers Dis. 5:477-478.

Almeida et al. (2006). "Evidence for the involvement of L-Arginine-Nitric Oxide-Cyclic Guanosine Monophosphate Pathway in the Antidepressant-Like Effect of Memantine in Mice," Behavioral Brain Res. 168:318-322.

Amantadine Drug Info. Located at http://medlineplus.gov/druginfo/meds/a682064.html; accessed online on Oct. 21, 2019, 6 total pages.

Anand, Om. (2009). "Dissolution Testing: An FDA perspective" AAPS Workshop, Physical pharmacy and Biopharmaceutics, 8 pages.

Baas, H. et al. (1997). "Catechol-O-methyltransferase inhibition with tolcapone reduces the "wearing off" phenomenon and levodopa requirements in fluctuating parkinsonian patients," J. Neurology, Neurosurgery, and Psychiatry 63:421-428.

Benson and Prankerd. (1997). "Optimisation of Drug Delivery, 3. Sustained/Controlled-Release Oral Drug Delivery," The Australian Journal of Hospital Pharmacy 27:381-389.

Blanchet, P.J. et al. (1998). "Amantadine reduces levodopa-induced dyskinesias in parkinsonian monkeys," Mov Disord, 13:798-802.

Bonnett (2000). A. Involvement of Non-Dopaminergic Pathways in Parkinson's Disease:Pathophysiology and Therapeutic Implications, CNS Drugs 13:351-364.

Braga, et al. (2005). "Making crystals from crystals: a green route to crystal engineering and polymorphism," Chemical Communications 3635-3645.

Breimer, D.D. (1996). "An integrated pharmacokinetic and pharmacodynamics approach to controlled drug delivery," J. Drug targeting 3:411-415.

Brigham, E.F. et al. (2018). "Pharmacokinetic/Pharmacodynamic correlation analysis of amantadine for Levodopa-induced dyskinesia," JPET, 37 total pages.

Brigham, E.F. et al. (2017). "Pharmacokinetic/Pharmacodynamic correlation analysis of amantadine for Levodopa-induced dyskinesia," J. Pharmacology and Experimental Therapeutics 367:373-381.

Brooks, D.J. (2008), "Optimizing levodopa therapy for Parkinson's disease with levodopa/carbidopa/entacapone: Implications from a clinical and patient perspective," Neuropsychiatric disease and Treatment 4:39-47.

Cameron, M.H. et al. (2019). "INROADS: A phase 3 study to assess the efficacy and safety of ADS-5102 (Amantadine) extended release capsules in multiple sclerosis patients with walking impairment," Poster, Adamas Pharmaceuticals, Emeryville, CA, 1 total page.

Cder (1997). "Guidance for Industry Extended Release Oral Dosage Forms: Development, Evaluation, and Application of in Vitro/In Vivo Correlations," Sep. 1997, U.S. Department of Health and Human Services Food and Drug Administration, pp. 1-24.

Cersosimo, et al. (2000). "Amantadine for the treatment of levodopa dyskinesias in Parkinson's disease," Medicina (B Aires) 60:321-325 (with full English translation).

Chung, M. et al. (1998). "Clinical pharmacokinetics of doxazosin in a controlled-release gastrointestinal therapeutic system (GITS) formulation," Br. J. Clin. Pharmacol. 48:678-687.

Clinical Trials.gov. (2013). Randomized Trial of Extended Release Amantadine Safety and Efficacy Study in Levodopa-Induced Dyskinesia (EASED Study).

Clinical Trials.gov. (2019). Extended Release Amantadine Safety and Efficacy Study in Levodopa-Induced Dyskinesia (EASED Study), NCT01397422, 1 total page.

Cohen, J. et al. (2017). "A phase 2 study of ADS-5102 (amantadine hydrochloride) extended release capsules in multiple sclerosis patients with walking impairment," Poster, Adamas Pharmaceuticals, Emeryville, CA, 1 total page.

Cohen, J.A. et al. (2018). "Safety and efficacy of ADS-5102 (amantadine) extended release capsules to improve walking in multiple sclerosis: A randomized, placebo-controlled, phase 2 trial," Multiple Sclerosis Journal, pp. 1-9.

Cohen, J.A. et al. (2018). "Safety and efficacy of ADS-5102 (amantadine) extended release capsules to improve walking in multiple sclerosis: A randomized, placebo-controlled, phase 2 trial," Multiple Sclerosis Journal, Supplementary Figure e-1, 1 total page.

CZ Arzneimittel: Amantadin-CT 100 mg. (2008) (with English translation), 19 total pages.

Da Silva-Junior, F.P. et al. (2005). "Amantadine reduces the duration of levodopa-induced dyskinesia: a randomized, double-blind, placebo-controlled study," Parkinsonism Relat Disord, 11(7):449-452.

Daugirdas, et al. (1984). "Binding o amantadine to red blood cells," Ther Drug Monit. 6:399-401.

De Graan, A.J.M. et al. (2011). "Dextromethorphan as a Phenotyping Test to Predict Endoxifen Exposure in Patients on Tamoxifen Treatment," Journal of Clinical Oncology 29:3240-3246.

Drapier, S. et al. (2011). "Apomorphine infusion in advanced Parkinson's patients with subthalamic stimulation contraindications," Parkin. Rel. Dis. 18:40-44.

Dr. Gabriele Ahrens. Opposition against EP2506709B1 of Adams Pharmaceuticals, Inc. US dated Apr. 20, 2017 filed in European Patent Office, 32 total pages.

Dunn, J. et al. (2017). "ADS-5102 (amantadine hydrochloride) extended-release capsules improve clinician's global impression of change (CGI-C) and activities of daily living (ADL) by reducing Levodopa-Induced Dyskinesia (LID) in patients with Parkinson's Disease (PD) (EASE LID Study)," Poster, Adamas Pharmaceuticals, Emeryville, CA, 1 total page.

Elmer, L.W. et al. (2018). "Pooled analyses of phase III studies of ADS-5102 (amantadine) extended-release capsules for dyskinesia in Parkinson's disease," CNS Drugs, 12 total pages.

Encarnacion, E.V. et al. (2008). "Levodopa-induced dyskinesias in Parkinson's disease: etiology impact on quality of life, and treatments," Eur Neurol, 60:57-66.

EP 05852057 (EP 1827385 A) Third Party Submission Under Art. 115 EPC dated May 25, 2012, 11 total pages.

EP 1874282 Patentee's Written Submissions Under Rule 1.16 EPC dated Sep. 7, 2012, 38 total pages.

EP 1874282 (Appl. No. 06749777.6) Granted Patent Claims—granted Sep. 15, 2010, 64 total pages.

EP 1874282 (Appl. No. 06749777.6) Opposition Against Patent dated Jun. 10, 2011, 31 total pages.

EP 1874282 (Appl. No. 06749777.6) Oral Proceedings Request dated May 30, 2012, 11 total pages.

Evidente, V.G.H. et al. (2000). "Amantadine is Beneficial in Restless Leg Syndrome," Movement Disorders 15:324-327.

(56) References Cited

OTHER PUBLICATIONS

European Search Report dated Dec. 20, 2016 for EP Application No. 16176422.0, 6 total pages.
European Search Report dated Apr. 22, 2013 for EP App. No. 10835150.3, 6 total pages.
European Search Report mailed on Apr. 21, 2021, for EP Application No. 18 848 121.2, filed on Aug. 23, 2018, 9 pages.
Final Office Action mailed on Apr. 10, 2020, for U.S. Appl. No. 16/409,554, filed May 10, 2019, 14 pages.
Final Office Action mailed on Jul. 20, 2020, for U.S. Appl. No. 16/677,431, filed Nov. 7, 2019, 15 pages.
Final Office Action mailed on Mar. 1, 2021, for U.S. Appl. No. 16/409,554, filed May 10, 2019, 15 pages.
Fox, S.H. et al. (2006). "Translation of non-dopaminergic treatments for levodopa-induced dyskinesia from MPTP-lesioned non-human primates to phase IIa clinical studies: keys to success and roads to failure," Mov Disord. 21:1578-1594.
Fung et al, Aust. Prescriber, 24(4) 2001, pp. 92-95).
Gocovri (2017). Orange Book: Approved drug products with therapeutics equivalence evaluations, Product details for NDA 208944 with Patent and exclusivity details for NDA 208944, 2 total pages.
Gocovri (2020). Highlights of prescribing information label, 19 total pages.
Goetz, et al. (2008). "Movement disorder Society-Sponsored Revision of the Unified Parkinson's Disease Rating Scale (MDS-UPDRS): Scale Presentation and Clinimetric Testing Results," Mov Disord 23:2129-2170.
Gracies JM, et al. (2002). "Current and Experimental Therapeutics of Parkinson's Disease; Neuropsychopharmacology: the Fifth Generation of Progress," pp. 1795-1816; American College of Neuropsychopharmacology.
Guidance for Industry: Bioavailability and Bioequivalence Studies for Orally Administered Drug Products—General Considerations. U.S. Department of Health and Human Services, FDA, CDER, Mar. 2003, 26 total pages.
Guidance For Industry: Food Effect Bioavailability and Fed Bioequivalence Studies. U.S. Department of Health and Human Services, FDA, CDER, Dec. 2002, 12 total pages.
Guidance for Industry. Waiver of In Vivo Bloavailability and Bioequivalence Studies for Immediate—Release Solid Oral Dosage Forms Based on a Blopharmaceutics Classification System. U.S. Dept. of Health and Human Services, FDA, CDER, Aug. 2000, 16 total pages.
Guide to MS Medications, Multiple Sclerosis Society of Canada, 2004, p. 9.
Guideline on the Investigation of Bioequivalence, European Medicines Agency, Jan. 20, 2010, 27 total pages.
Guttman, M. et al. (2003). "Current concepts in the diagnosis and management of Parkinson's disease," Cmaj, 168:293-301.
Hayden (1983). "Differences in Side Effects of Amantadine Hydrochloride and Rimantadine Hydrochloride Relate to Differences in Pharmacokinetics," AAC. 23:458-464.
Hayden, F. (1981). "Comparative Toxicity of Amantadine Hydrochloride and Rimantadine Hydrochloride in Healthy Adults," Antimicrobial Agents and Chemotherapy 19:226-233.
Hayden, F. (1985). "Comparative single-doser pharmacokinetics of amantadine hydrochloride and rimantadine hydrochloride in young and elderly adults," Antimicrobial Agents and Chemotherapy 28:216-221.
Hauser, et al. (2000). "A Home Diary to Assess Functional Status in Patients with Parkinson's Disease with Motor Fluctuations and Dyskinesia," Clin. Neuropharmacol. 23:75-81.
Hauser, R.A. et al. (2018). "Pharmacokinetics of ADS-5102 (amantadine) extended release capsules administered once daily at bedtime for the treatment of dyskinesia," Clin. Pharmacokinet. 12 total pages.
Hauser, R.A. et al. (2019). "Prevalence of dyskinesia and OFF by 30-minute intervals through the day and assessment of daily episodes of dyskinesia and OFF: Novel analyses of diary data from Gocovri pivotal trials," J. Parkins. Disease, 10 total pages.
Hauser, R.A. et al. (2019). "Prevalence of dyskinesia and OFF by 30-minute intervals through the day and assessment of daily episodes of dyskinesia and OFF: Novel analyses of diary data from Gocovri pivotal trials," J. Parkins. Disease, Supplemental Material, 5 total pages.
Hauser, R.A. et al. (2017). "ADS-5102 (amantadine) extended-release capsules for Levodopa-induced dyskinesia in Parkinson's disease (EASE LID 2 study): Interim results of an open-label safety study," J. Parkins. Disease 7:511-522.
Hauser, R.A. et al. (2017). "ADS-5102 (amantadine) extended-release capsules for Levodopa-induced dyskinesia in Parkinson's disease (EASE LID 2 study): Interim results of an open-label safety study," J. Parkins. Disease 7:511-522, Supplemental Table 1, 1 total page.
Hauser, R.A. et al. (2017). "Update to interim results of a long-term open-label safety study of ADS-5102 (amantadine hydrochloride) extended-release capsules for treatment of Levodopa-Induced Dyskinesia (LID) (EASE LID 2 study)," Poster, Adamas Pharmaceuticals, Emeryville, CA, 1 total page.
Hauser, R.A. et al. (2019). "Troublesome Dyskinesia and OFF prevalence throughout the day: Population profile and Gocovri effects on frequency and duration of these episodes relative to placebo," Poster, Adamas Pharmaceuticals, Emeryville, CA, 1 total page.
Hauser, R.A. et al. (2017). "Expanded results of an ongoing long term open-label Phase 3 study of ADS-5102 (amantadine) extended-release capsules for treatment of Levodopa-induced Dyskinesia (LID) (EASE LID 2 study)," Poster, Adamas Pharmaceuticals, Emeryville, CA, 1 total page.
Hauser, R.A. et al. (2018). "Pharmacokinetics of ADS-5102 (amantadine) extended release capsules administered once-daily at bedtime for the treatment of Dyskinesia," Poster, Adamas Pharmaceuticals, Emeryville, CA, 1 total page.
Hauser, R.A. et al. (2018). "Final MDS-UPDRS, Part IV results of the EASE LID 2 study: Long term, open-label study of ADS-5102 for Dyskinesia in Parkinson's disease (PD) patients," Poster, Adamas Pharmaceuticals, Emeryville, CA, 1 total page.
Hobart, J.C. et al. (2003). "Measuring the impact of MS on walking ability: The 12-item MS walking scale (MSWS-12)," Neurology 60:31-36.
Hunter, S. et al. (2017). "ADS-5102 (amantadine) extended release capsules in multiple sclerosis patients with walking impairment: A phase 2 proof of concept study," Poster, Adamas Pharmaceuticals, Emeryville, CA, 2 total pages.
Ing et al. (1979). "Toxic effects of amantadine in patients with renal failure," CMA Journal 120:695-697.
International Search Report mailed on Oct. 4, 2018, for PCT Application No. PCT/US2018/047754, filed on Aug. 23, 2018, 3 pages.
International search report dated Feb. 7, 2011 for PCT/US2010/058789, 3 total pages.
International search report dated May 8, 2006 for PCT Application No. PCT/US2005/042424 (522), 4 total pages.
International search report dated Aug. 9, 2006 for PCT Application No. PCT/US2005/42780, 5 total pages.
International Search Report for PCT/US2006/013506, mailed Jan. 12, 2007, Feb. 23, 2007 Corrected Version, 6 total pages.
International Search Report for PCT/US2014/42690, mailed Jun. 17, 2014, 3 total pages.
International Search Report malled on Jan. 27, 2016, for PCT Application No. PCT/US2015/58872, filed on Nov. 3, 2015, 3 pages.
International Written Opinion dated Aug. 8, 2006 for PCT/US2005/42780, 9 total pages.
Isaacson, S.H. et al. (2018). "Parkinson's patients with Dyskinesia switched from immediate release amantadine to open-label ADS-5102," Movement Dis., 8 total pages.
Isaacson, S.H. et al. (2018). "Parkinson's patients with Dyskinesia switched from immediate release amantadine to open-label ADS-5102," Movement Dis., Supplemental Tables 1 and 2, 2 total pages.
Isaacson, S. et al. (2019). "A two-year phase 3 open-label study of Gocovri in Parkinson's disease patients with OFF and Dyskinesia

(56) References Cited

OTHER PUBLICATIONS (EASE LID 2): Analysis of changes to Levodopa daily dose," Poster, Adamas Pharmaceuticals, Emeryville, CA, 1 total page.
Isaacson, S. et al. (2018). "Final safety results of EASE LID 2 study: Long term open-label study of ADS-5102 for dyskinesia in Parkinson's disease (PD) patients," Poster, Adamas Pharmaceuticals, Emeryville, CA, 1 total page.
Isaacson, S.H. et al. (2017). "ADS-5102 provided reduction in motor complications in Parkinson's disease (PD) patients with dyskinesia switched from amantadine IR (AMT-IR): Subgroup analysis from an ongoing open-label Phase 3 study (EASE LID 2)," Poster, Adamas Pharmaceuticals, Emeryville, CA, 1 total page.
Jackson et al. (1967). "Chemoprophylaxis of viral respiratory diseases," Pan American Health Organization pp. 595-603.
Jackson, G.G. et al. (1976). "Prevention and control of influenza by chemoprophylaxis and chemotherapy. Prospects from examination of recent experience," JAMA 235:2739-2742.
Kim, Y.E. et al. (2012). "Intravenous amantadine for freezing of gait resistant to dopaminergic therapy: a randomized, double-blind, placebo-controlled, cross-over clinical trial," PLOS ONE 7:e488960, 6 total pages.
Klockgether, et al. NMDA antagonists potentiate antiparkinsonian actions of L-dopa in monoamine-depleted rats. Ann Neurol. Oct. 1990; 28(4):539-46.
Kuo, S.H. et al. (2008). "Bilateral pedunculopontine nuclei strokes presenting as freezing of gait," Mov. Disorder 23:616-619.
Lewitt, et al. (2008). "Adenosine A2A receptor antagonist istradefylline (KW-6002) reduces "off" time in Parkinson's disease: a double-blind, randomized, multicenter clinical trial (6002-US-005)," Ann Neural 63:295-302.
Lowenthal, D.T. et al. (1985). "The effect of renal function on enalapril kinetics," Clinical Pharmacology and Therapeutics 38:661-666.
Luginger, E. et al. (2000). "Beneficial effects of amantadine on L-dopa-induced dyskinesias in Parkinson's disease," Mov Disord, 15:873-878.
MedLinePlus: Amantadine citation retrieved from http Located at http://medlineplus.gov/druginfo/meds/a682064.html; accessed online on Feb. 2, 2018, 4 total pages.
Mehta, S. et al. (2018). "Effects of ADS-5102 on non-motor symptoms in Parkinson's disease patients with Dyskinesia," Poster, Adamas Pharmaceuticals, Emeryville, CA, 1 total page.
Metman, L.V. et al. (1999). "Amantadine for levodopa-induced dyskinesias: a 1-year follow-up study," Arch Neurol. 56:1383-1386.
Metman et al. (1998). "Amantadine as treatment for dyskinesias and motor fluctuations in Parkinson's disease," Neurology 50:1323-1326.
Mitra, A. et al. (2018). "The NMDA receptor channel blocker Amantadine reduces LTP in multiple brain regions," Poster, Adamas Pharmaceuticals, Emeryville, CA, 1 total page.
Mori, S. (2002). "Responses to Donepezil in Alzheimer's Disease and Parkinson's Disease," Ann. NY Acad Sci. 977:493-500.
Morrison et al. (2007). "A randomized, crossover study to evaluate the pharmacokinetics of amantadine and oseltamivir administered alone and in combination," PLoS One 12: e1305.
ND 21-487 Namenda Approved Labeling. 2003; p. 1-20.
National Sleep Foundation (2006). Sleep-wake cycle: Its physiology and impact on health, 27 total pages.
Navarro, R. et al. (2017). "An assessment of the persistence and medication possession ratio of adjunctive treatments to Levodopa in patients with Parkinson's disease (PD)," Poster, Adamas Pharmaceuticals, Emeryville, CA, 1 total page.
Neutel et al. (1996). "Novel delivery system for verapamil designed to achieve maximal blood pressure control during the early morning," American Heart Journal 132:1202-1206.
Nguyen, J. et al. (2013). "Preclinical and clinical update on Nurelin (ADS-5102), a novel formulation of amantadine HCl for CNS disorders," Poster, Adamas Pharmaceuticals, Emeryville, CA, 1 total page.
Nguyen, J. et al. (2013). "Amantadine improves cognitive outcome after fluid percussion traumatic brain injury in rats," Poster, Adamas Pharmaceuticals, Emeryville, CA. and University of California, Davis, CA. 1 total page.
Nguyen, J. et al. (2017). "Amantadine ameliorates gait deficits and disease severity in an animal model of multiple sclerosis," Poster, Adamas Pharmaceuticals, Emeryville, CA. 1 total page.
Nguyen, J. et al. (2018). "Initial rate of rise in plasma concentrations is a significant contributor to CNS side effects associated with amantadine," Poster, Adamas Pharmaceuticals, Emeryville, CA, 1 total page.
Nguyen, J. (2018). "Pharmacokinetic/Pharmacodynamic analysis of amantadine for levodopa-induced dyskinesia," Presentation, Abstract No. 1476, Platform presentation No. 006, 11 total pages.
Nilsgard, Y. et al. (2007). "Clinical relevance using timed walk tests and 'timed up and go' testing in persons with multiple sclerosis," Physiother. Res. Int. 12:105-114.
Non-Final Office Action mailed on Dec. 30, 2019, for U.S. Appl. No. 16/677,431, filed Nov. 7, 2019, 10 pages.
Non-Final Office Action mailed on Dec. 4, 2019, for U.S. Appl. No. 16/409,554, filed May 10, 2019, 12 pages.
Non-Final Office Action mailed on Jul. 20, 2020, for U.S. Appl. No. 16/409,554, filed May 10, 2019, 17 pages.
Non-Final Office Action mailed on Feb. 2, 2021, for U.S. Appl. No. 16/677,431, filed Nov. 7, 2019, 10 pages.
Notice of Allowance mailed on May 26, 2021, for U.S. Appl. No. 16/409,554, filed May 10, 2019, 9 pages.
Notice of Allowance mailed on May 26, 2021, for U.S. Appl. No. 16/677,431, filed Nov. 7, 2019, 9 pages.
Note for Guidance on Modified Release Oral and Transdermal Dosage Forms: Section II, European Agency for the Evaluation of medicinal Products, Jul. 28, 1999, 12 total pages.
Nutt, J.G. (2001). "Motor fluctuations and dyskinesia in Parkinson's disease," Parkin. Rel. Dis. 8:101-108.
Oertel, W. et al. (2017). "Randomized, placebo-controlled trial of ADS-5102 (amantadine) extended-release capsules for Levodopa-induced dyskinesia in Parkinson's disease (EASE LID 3)," Movement Disorders, 9 total pages.
Oertel, W. et al. (2017). "Randomized, placebo-controlled trial of ADS-5102 (amantadine) extended-release capsules for Levodopa-induced dyskinesia in Parkinson's disease (EASE LID 3)," Movement Disorders, Supplemental Materials, 3 total pages.
Paci, C. et al. (2001). "Amantadine for dyskinesia in patients affected by severe Parkinson's disease," Neurol Sci, 22:75-76.
Pahwa et al. (2015). "Amantadine Extended Release for Levodopa-Induced Dyskinesia in Parkinson's Disease (EASED Study)," Mov Disord. 30:788-795.
Pahwa, R. et al. (2013). Randomized Trial of Extended Release Amantadine in Parkinson's Disease Patients with Levodopa-induced Dyskinesia (EASED Study), In 17th International Congress of Parkinson's Disease and Movement Disorders (MDS), Sydney, Australia, presented Jun. 18, 2013, 1 total page.
Pahwa et al. (2017). "ADS-5102 (Amantadine) Extended-Release Capsules for Levodopa-Induced Dyskinesia in Parkinson Disease (EASE LID Study): A Randomized Clinical Trial," *JAMA Neurol.* 174:941-949.
Pahwa et al. (2017). "ADS-5102 (Amantadine) Extended-Release Capsules for Levodopa-Induced Dyskinesia in Parkinson Disease (EASE LID Study): A Randomized Clinical Trial," *JAMA Neurol.* 74:941-949, Supplemental Material, 5 total pages.
Pahwa, R. et al. (2018). "Impact of dyskinesia on activities of daily living in Parkinson's disease: Results from pooled phase 3 ADS-5102 clinical trials," Parkin, Related Dis., 8 total pages.
Pahwa, R. et al. (2013). "Safety and efficacy study of ADS-5102 in Levodopa-induced dyskinesia (EASED study)," Poster, Adamas Pharmaceuticals, Emeryville, CA, 1 total page.
Pahwa, R. et al. (2014). "Safety and efficacy study of ADS-5102 (amantadine HCl) extended release capsules in Levodopa induced dyskinesia (EASED study)," Poster, Adamas Pharmaceuticals, Emeryville, CA, 1 total page.

(56) References Cited

OTHER PUBLICATIONS

Pahwa, R. et al. (2016). "ADS-5102 (amantadine HCl) extended-release capsules reduced Levodopa-induced Dyskinesia (LID) in the Phase 3 EASE LID study," Poster, Adamas Pharmaceuticals, Emeryville, CA, 1 total page.

Pahwa, R. et al. (2016). "Interim results of a long-term open-label safety study of ADS-5102 extended-release capsules for treatment of Levodopa-induced Dyskinesia (EASE LID 2 study)," Poster, Adamas Pharmaceuticals, Emeryville, CA, 1 total page.

Pahwa, R. et al. (2016). "ADS-5102 extended-release capsules reduced Levodopa-induced Dyskinesia in the Phase 3 EASE LID study," Poster, Adamas Pharmaceuticals, Emeryville, CA, 1 total page.

Pahwa, R. et al. (2016). "Results of a phase 3 efficacy and safety study of ADS-5102 (amantadine HCl) extended-release capsules in Parkinson's disease patients with Levodopa-induced Dyskinesia (EASE LID 3)," Poster, Adamas Pharmaceuticals, Emeryville, CA, 1 total page.

Pahwa, R. et al. (2016). "ADS-5102 (amantadine HCl) extended-release capsules improves activities of daily living in Parkinson's disease patients by reducing Levodopa-induced Dyskinesia: A post-Hoc analysis from the Phase 3 EASE LID study," Poster, Adamas Pharmaceuticals, Emeryville, CA, 1 total page.

Pahwa, R. (2017). "Pooled analysis of Phase 3 studies of ADS-5102 (amantadine) extended release capsules for levodopa-induced Dyskinesia," Presentation, Abstract No. 2907, Platform lpresentation No. 03, 10 total pages.

Pahwa, R. (2017). "Pooled analysis of Phase 3 studies of ADS-5102 (amantadine) extended release capsules for levodopa-induced Dyskinesia: A detailed review of UDysRS results," Poster, Adamas Pharmaceuticals, Emeryville, CA, 1 total page.

Pahwa, R. et al. (2018). "ADS-5102 reduces ON time with troublesome Dyskinesia and OFF time throughout the walking day—time course analysis," Poster, Adamas Pharmaceuticals, Emeryville, CA, 1 total page.

Pahwa, R. et al. (2018). "Impact of dyskinesia in Parkinson's disease (PD) on activities of daily living (ADLs) and daily tasks: Results from pooled Phase 3 ADS-5102 clinical trials," Poster, Adamas Pharmaceuticals, Emeryville, CA, 1 total page.

Pahwa, R. et al. (2018). "A clinically important difference (CID) for the unified Dyskinesia rating scale (UDysRS) total score change in Parkinson's Disease (PD) patients with Dyskinesia," Poster, Adamas Pharmaceuticals, Emeryville, CA, 1 total page.

Parkes, J.D. et al. (1970). "Amantadine dosage in treatment of Parkinson's disease," The Lancet 295:1130-1133.

Parkes, J.D. (1989). "Clinical pharmacology of amantadine and derivatives, in Early Diagnosis and Preventative Therapy in Parkinson's Disease," Springer-Verlag/Wien, pp. 335-341.

PD Workbook (2006). Unified Parkinson's Disease rating scale, 8 total pages.

Physicians' Desk Reference (2002). Sinemet Prescribing Information, 5 total pages.

Physicians' Desk Reference (2002). Detrol LA Prescribing Information, 4 total pages.

Physicians' Desk Reference (2002). Detrol Prescribing Information, 4 total pages.

Physicians' Desk Reference (2002). Effexor XR Prescribing Information, 7 total pages.

Physicians' Desk Reference (2002). Glucotrol Prescribing Information, 3 total pages.

Physicians' Desk Reference (2002). Glucotrol XL Prescribing Information, 5 total pages.

Physicians' Desk Reference (2002). Lescol Prescribing Information, 6 total pages.

Physicians' Desk Reference (2002). Ritalin Prescribing Information, 3 total pages.

Physicians' Desk Reference (2002). Symmetrel Prescribing Information, 4 total pages.

PK-Merz film coated tablet (2003). Summary of Product Characteristics, pp. 1-8.

Qiu, Y. et al. (2000). "Research and development aspects of oral controlled-release dosage forms," *Handbook of Pharmaceutical Controlled Release* Technology, Marcel Dekker, Inc., pp. 465-503.

Rajput, et al. (1998). "New use for an old drug: amantadine benefits levodopa induced dyskiensias," Mov Disord 13:851-854.

Rascol, O. et al. (2005). Rasagiline as an adjunct to levodopa in patients with Parkinson's disease and motor fluctuations (LARGO, lasting effect in adjunct therapy with Rasagiline given once daily.

Rollins (2000). "Clinical Pharmacokinetics," Remington: The Practice and Science of Pharmacy, 20th Ed., Ch. 59, p. 1145-1155.

Ruzicka, et al. (2000). "Amantadine infusion treatment of motor fluctuations and dyskinesias in Parkinson's disease," J Neural Trans. 102:1297-1306.

Sakai, S. (2008). How to read or understand a prescription: Insomnia, Yuge Hospital Saori Sakai, English translation, pp. 1-29.

Schrag, A. (2005). "Entacapone in the treatment of Parkinson's Disease," Lancet Neurol. 4:366-370.

Schwab, R. et al. (1972). "Amantadine in Parkinson's Disease Review of More Than Two Years' Experience," JAMA. 222:792-795.

Shafer, S.L. (1991). "Targeting the effect site a computer controlled infusion pump," Adv. Meth. Pharma. Pharma. Systems Analysis, pp. 185-197.

Shannon, K.M. et al. (1987). "Amantadine and Motor Fluctuations in Chronic Parkinson's Disease," Clinical Neuropharmacology 10:522-526.

Socie et al. (2013). Multiple Sclerosis Int'l., vol. 2013, Article ID No. 645197, 7 pages.

Snow, B.J. et al. (2000). "The effect of amantadine on levodopa-induced dyskinesias in Parkinson's disease: a double-blind, placebo-controlled study," Clin Neuropharmacol. 23:82-85.

Spieker et al. (1999). "The NMDA antagonist budipine can alleviate levodopa-induced motor fluctuations," Mov Disord. 14:517-519.

Standaert, et al. (2001). Chapter 22: Treatment of central nervous system degenerative disorders. Goodman and Gilman's The Pharmacological Basis of Therapeutics 10th Ed., Hardman Limbird and Gilman Eds., McGraw-Hill, New York, 20 total pages.

Stempien, M.J. et al. (2014). "Rater training and data completeness in the study of ADS-5102 in Levodopa-induced dyskinesia (EASED study)," Poster Session No. 722, Movement Disorders, vol. 29, Suppl. 1, 1 total page.

Stempien, M.J. et al. (2015). "ADS-5102 increased ON time without troublesome Dyskinesia throughout waking hours in the EASED study," Poster, Adamas Pharmaceuticals, Emeryville, CA. 1 total page.

Symmetrel Amantadine HCl. (2012). Retrieved from the internet: URL http://www.pbs.gov.au/meds%2Fpi%2Fnvpsymor10611.pdf (retrievedonJul. 25, 2012), 15 total pages.

SYMMETREL (2002). Amantadine hydrochloride, USP, tablets and syrup, 12 total pages.

SYMMETREL® (Amantadine Hydrochloride, USP), Tablets and Syrup ("Symmetrel Label") issued in Jan. 2009, 15 total pages.

Tanner, C.M. et al. (2017). "Pooled analysis of Phase 3 studies of ADS-5102 (amantadine) extended release capsules for levodopa-induced dyskinesia: A detailed review of PD home diary results," Poster, Adamas Pharmaceuticals, Emeryville, CA. 1 total page.

Tanner, C.M. et al. (2017). "Pooled analysis of Phase 3 studies of ADS-5102 for levodopa-induced dyskinesia: A detailed review of MDS-UPDRS, Part IV (motor complications)," Poster, Adamas Pharmaceuticals, Emeryville, CA. 1 total page.

Thanvi et al. (2004). "Long term motor complications of levodopa: clinical features, mechanisms, and management strategies," Postgrad Med. J. 80:452-458.

Thobois, S. et al. (2005). "Treatment of motor dysfunction in Parkinson's disease: An overview," Clin. Neurol. Neurosurg. 107:269-281.

Thomas, A. et al. (2004). "Duration of amantadine benefit on dyskinesia of severe Parkinson's disease," J Neurol Neurosurg Psychiatry 75:141-143.

Toutain et al. (2004). "Bioavailability and its assessment," J. of Pharmacology and Therapeutics 27:455-466.

(56) References Cited

OTHER PUBLICATIONS

Wakelkamp, M. et al. (1998). "The influence of drug input rate on the development of tolerance to frusemide," Br. J. Clin. Pharmacol. 46:479-487.

Wang, T. et al. (2012). "Repeated post-injury dosing with amantadine improves cognitive outcome after fluid percussion TBI in rats," Poster, University of California, Davis, CA and Adamas Pharmaceuticals, Emeryville, CA, 1 total page.

Warren et al. (2004), "The use of amantadine in Parkinson's disease and other Akinetic-rigid disorders," ACNR 4:38-41.

Warren et al. (2009). "The scientific and clinical basis for the treatment of Parkinson disease (2009)," Neurology 72(Suppl 4):S1-S136.

Waters, C.H. et al. (2004). "Zydis selegiline reduces Off time in Parkinson's disease patients with motor fluctuations: A 3-month, randomized, placebo-controlled study," Movement Disorders 19:426-432.

Waters, C.H. (2002). "Treatment of advanced stage patients with Parkinson's disease," Parkinsonsim and Related Disorders 9:15-21.

Wessell et al. (2004). "NR2B selective NMDA receptor antagonist CP-101,606 prevents levodopa-induced motor response alterations in hemi-parkinsonian rats," Neuropharmacology 47:184-194.

Wilkinson, GR. (2001). Chapter 1: Pharmacokinetics. Goodman and Gilman's The Pharmacological Basis of Therapeutics 10th Ed., Hardman Limbird and Gilman Eds., McGraw-Hill, New York.

Wilson, et al. (2002). Combination drug regimens hold great promise for Alzheimer treatment. Science Blog. Located at http://www3.scienceblog.com/community/older/archives/K/5/pub5611.html, retrieved on Oct. 22, 2019, 3 total pages.

Wimo et al. (2002). Effect of long-term treatment with memantine, and nmda antagonist on costs associated with advanced Alzheimer's disease: results of a 28-week, randomized, double-blind, placebo-controlled study. Abstracts from the 8th International Conference on Alzheimer's Disease and Related Disorders. Stockholm, Sweden. Jul. 20-25, 2002. No. 167, 1 total page.

Wimo, et al. (2002). Pharmacoeconomics and dementia. Abstracts from the 8th International Conference on Alzheimer's Disease and Related Disorders. Stockholm, Sweden. Jul. 20-25, 2002.

Winblad et al. (2001). "A 1-year, randomized, placebo-controlled study of donepezil in patients with mild to moderate AD," Neurology 57:489-495.

Written Opinion of the International Searching Authority mailed on Oct. 4, 2018, for PCT Application No. PCT/US2018/047754, filed on Aug. 23, 2018, 9 pages.

Zeldowicz, L.R. et al. (1973). "Long-term therapy of Parkinson's disease with amantadine, alone and combined with levodopa," CMA Journal 109:588-593.

Zesiewicz, T.A. et al. (2007). "Levodopa-induced Dyskinesia in Parkinson's Disease: Epidemiology, Etiology, and Treatment," Curr. Neurol, Neurosci. Rep. 7:302-310.

U.S. Appl. No. 16/841,452, filed Apr. 6, 2020, by Went et al. (Copy not attached).

U.S. Appl. No. 16/877,067, filed May 18, 2020, by Went et al. (Copy not attached).

U.S. Appl. No. 17/088,369, filed Nov. 3, 2020, by Went et al. (Copy not attached).

U.S. Appl. No. 17/135,202, filed Dec. 28, 2020, by Went et al. (Copy not attached).

U.S. Appl. No. 17/522,752, filed Nov. 9, 2021, by Went et al. (Copy not attached).

U.S. Appl. No. 17/399,659, filed Aug. 11, 2021, by Went et al. (Copy not attached).

Bauer, K.H. et al. (1997). "Chapter 16: Dosage forms with controlled release of active substance—Retardation and depot dosage forms," in Pharmaceutical Technology, Gustav Fischer Verlag, pp. 361-362, (with English Translation).

Voigt, R. et al. (2000). "Chapter 12: Peroral depot dosage forms," in Pharmaceutical Technology, German Pharmacist Publishing House Stuttgart, pp. 245-248 (with English Translation).

U.S. Appl. No. 18/500,801, filed Nov. 2, 2023, by Went et al. (Copy not attached).

U.S. Appl. No. 18/404,230, filed Jan. 4, 2024, by Went et al. (Copy not attached).

U.S. Appl. No. 18/440,533, filed Feb. 13, 2024, by Went et al. (Copy not attached).

U.S. Appl. No. 18/748,810, filed on Jun. 20, 2024, by Went et al. (Copy not attached).

\* cited by examiner

FIG. 1: Dissolution Profiles of two extended release compositions of amantadine HCl FIG. 2: Single dose plasma concentration curve for two amantadine formulations FIG. 3: Single dose plasma concentration curve for two amantadine formulations

AMANTADINE COMPOSITIONS, PREPARATIONS THEREOF, AND METHODS OF USE

CROSS-REFERENCE TO RELATED APPLICATIONS

This application is a continuation of U.S. patent application Ser. No. 16/677,431, filed on Nov. 7, 2019, now issued as U.S. Pat. No. 11,065,213, which is a divisional of U.S. patent application Ser. No. 16/409,554, filed on May 10, 2019, now issued as U.S. Pat. No. 11,077,073, which is a continuation application of International Application No. PCT/US2018/047754, filed on Aug. 23, 2018, which claims the benefit of U.S. Provisional Application No. 62/549,921, filed on Aug. 24, 2017, the disclosures of which are incorporated herein by reference in their entireties.

FIELD

This disclosure generally relates to oral pharmaceutical compositions comprising amantadine, or pharmaceutically acceptable salts thereof, and more specifically relates to extended release oral pharmaceutical compositions comprising amantadine, or pharmaceutically acceptable salts thereof, the preparation of such compositions, and methods of using such compositions.

BACKGROUND

Amantadine is indicated for various conditions that can be treated by NMDA receptor antagonists including the treatment of idiopathic Parkinson's disease (Paralysis Agitans), post-encephalitic Parkinsonism, and symptomatic Parkinsonism which may follow injury to the nervous system by carbon monoxide intoxication. Amantadine also has activity as a viral M2 channel inhibitor and is used for the prophylaxis and treatment of infection of viral diseases, especially influenza A virus.

Levodopa, the most commonly prescribed and effective drug treatment for symptomatic relief in Parkinson's disease (PD) is associated with dose-limiting motor side-effects, including abnormal involuntary movements known as levodopa-induced dyskinesia (LID). With continued levodopa treatment, and as PD progresses to moderate and severe stages, dyskinesias can become severely disabling and have been associated with a decrease in the quality of life. Encarnacion, E. V. and Hauser, R. A., Levodopa-induced dyskinesias in Parkinson's disease: etiology, impact on quality of life, and treatments. Eur Neurol, 2008. 60(2): p. 57-66. There are currently no medications approved for the treatment of LID, thus there is a significant unmet medical need (as of August 2017).

LID may require a reduction in the levodopa dose causing patients to receive sub-optimal PD treatment. The treatment of LID that becomes severely disabling resulting in a decrease in the quality of life is an unmet medical need. Encarnacion et al., supra.

As of August 2018, the extended release formulation of amantadine hydrochloride GOCOVRI™ was the first and only medicine approved by the U.S. Food and Drug Administration (FDA) for the treatment of dyskinesia in people with Parkinson's disease receiving levodopa-based therapy, with or without concomitant dopaminergic medications. GOCOVRI™ is the first Parkinson's disease medicine proven in controlled trials to reduce both dyskinesia and OFF time in Parkinson's disease patients receiving levodopa.

Amantadine (amantadine) is a weak, non-competitive N-methyl d-aspartate (NMDA) receptor antagonist that promotes release of dopamine. Guttman, M., Kish, S. J., Furukawa, Y., Current concepts in the diagnosis and management of Parkinson's disease. Cmaj, 2003. 168(3): p. 293-301. Amantadine has shown efficacy in animal models of LID and is used off-label by neurologists and movement disorder specialists to treat LID in patients with PD. Blanchet, P. J., Konitsiotis, S., Chase, T. N., Amantadine reduces levodopa-induced dyskinesias in parkinsonian monkeys. Mov Disord, 1998. 13(5): p. 798-802. Fox, S. H., Lang, A. E., Brotchie, J. M., Translation of non-dopaminergic treatments for levodopa-induced dyskinesia from MPTP-lesioned nonhuman primates to phase IIa clinical studies: keys to success and roads to failure. Mov Disord, 2006. 21(10): p. 1578-94.

A number of small studies with different designs and outcome measures in PD patients have shown amantadine (IR formulation) to be effective in the treatment of LID. At amantadine doses of 200 mg/day, an approximately 25% reduction in LID was reported (da Silva-Junior, F. P., Braga-Neto, P., Monte, F. S., et al., Amantadine reduces the duration of levodopa-induced dyskinesia: a randomized, double-blind, placebo-controlled study. Parkinsonism Relat Disord, 2005. 11(7): p. 449-52; Snow, B. J., Macdonald, L., Mcauley, D., et al., The effect of amantadine on levodopa-induced dyskinesias in Parkinson's disease: a double-blind, placebo-controlled study. Clin Neuropharmacol, 2000. 23(2): p. 82-85) and at doses of 300 mg/day, the reduction of LID was reported to be ~40% (Luginger, E., Wenning, G. K., Bosch, S., et al., Beneficial effects of amantadine on L-dopa-induced dyskinesias in Parkinson's disease. Mov Disord, 2000. 15(5): p. 873-8; Paci, C., Thomas, A., Onofrj, M., Amantadine for dyskinesia in patients affected by severe Parkinson's disease. Neurol Sci, 2001. 22(1): p. 75-6; Thomas, A., Iacono, D., Luciano, A. L., et al., Duration of amantadine benefit on dyskinesia of severe Parkinson's disease. J Neurol Neurosurg Psychiatry, 2004. 75(1): p. 141-3.) In one study conducted at 300 to 400 mg/day, the reduction was reported to be ~60% (Metman, L. V., Del Dotto, P., Lepoole, K., et al., Amantadine for levodopa-induced dyskinesias: a 1-year follow-up study. Arch Neurol, 1999. 56(11): p. 1383-6.) In general, the reduction in LID appears to increase with increasing amantadine dose.

Many marketed forms of amantadine are generally immediate release formulations that are typically administered two or more times a day. Amantadine's use is limited by dose related CNS side effects including dizziness, confusion, hallucinations, insomnia and nightmares (Gracies J M, Olanow C W; Current and Experimental Therapeutics of Parkinson's Disease; *Neuropsychopharmacology: the Fifth Generation of Progress pp* 1802; American College of Neuropsychopharmacology 2002), which can be particularly exacerbated when amantadine is administered late in the day (Jackson et al., Bull Pan Am Health Org, 147, 595-603 (1967)); Jackson, JAMA, 235(25), (1976), 2739-2742; Hayden, AAC, 19(2) 1981, pp. 226-233; and Hayden, AAC, 23(3) 1983, pp. 458-464).

Doses of 200 mg/day of amantadine (IR formulation) have been generally tolerated by the majority of PD patients. However, at this dose level, amantadine efficacy in LID is sub-optimal for many patients. Doses of 300 mg/day or higher amantadine IR produce greater reduction in LID symptoms but are associated with central nervous system (CNS) side effects including hallucinations, insomnia, nausea and dizziness (lightheadedness) and gastrointestinal (GI) side effects including loss of appetite, nausea, vomiting, and diarrhea (Jackson et al., supra; Hayden, supra). In one study of immediate release amantadine, increased plasma concentrations were associated with a higher incidence of CNS and sleep related side effects, but not with GI side effects (Hayden 1983, supra).

It is known that immediate release amantadine can act as a stimulant, causing insomnia and sleep disturbance. Therefore, the last dose is typically administered no later than 4 pm in order to minimize these side effects (Fachinformation—Amantadin CT 100 mg Filmtabletten, March, 2008; Fung et al, Aust. Prescriber, 24(4) 2001, pp 92-95). Such dosing of amantadine results in peak plasma amantadine concentrations occurring in the evening or night, and very low plasma concentrations in the morning.

Extended release forms of amantadine have been described in the art. U.S. Pat. No. 5,358,721, to Guittard et al., and U.S. Pat. No. 6,217,905, to Edgren et al., each disclose an oral osmotic dosage form comprising an antiviral or anti-Parkinson's drug, respectively, where in each case amantadine is listed as a possible drug to be utilized in the dosage form. U.S. Pat. No. 6,194,000, to Smith et al., discloses analgesic immediate and controlled release pharmaceutical compositions utilizing NMDA receptor antagonists, such as amantadine, as the active agent. U.S. Patent Appl. Publication Nos. US 2006/0252788, US 2006/0189694 (U.S. Pat. No. 8,389,578), US 2006/0142398, US 2008/0227743, and US2011/0189273 (U.S. Pat. No. 8,741,343), all to Went et al., each disclose the administration of an NMDA receptor antagonist, such as amantadine, optionally in controlled release form.

Recently, an extended release formulation of amantadine has been shown to reduce LID in Parkinson's patients taking levodopa (Pahwa et al. Amantadine Extended Release for Levodopa-Induced Dyskinesia in Parkinson's Disease (EASED Study), Mov Disord. 2015. 30(6):788-795). These extended release compositions are administered once nightly at 260 to 420 mg without increasing sleep related adverse effects (US20110189273, US20150087721, Pahwa et al., supra). Immediate release forms of amantadine have been used to treat fatigue in patients with Multiple Sclerosis. Recently, extended release compositions have been investigated for treating hypokinetic movement disorders in patients with Multiple Sclerosis (US2016/0228388). As discussed above, the extended release formulation of amantadine hydrochloride GOCOVRI™ was recently approved by the FDA as the first and only medicine approved by the FDA for the treatment of dyskinesia in people with Parkinson's disease receiving levodopa-based therapy, with or without concomitant dopaminergic medications. GOCOVRI™ is the first Parkinson's disease medicine proven in controlled trials to reduce both dyskinesia and OFF time in Parkinson's disease patients receiving levodopa.

However, gastrointestinal side effects associated with administration of immediate release and known extended release amantadine formulations remain a significant issue; thus, improved compositions and methods are needed.

SUMMARY

Described herein are extended release oral compositions comprising amantadine, or a pharmaceutically acceptable salt thereof, and methods of administering amantadine, or a pharmaceutically acceptable salt thereof (such as amantadine hydrochloride), which provide improved gastrointestinal adverse event rates over the known formulations. The compositions of the present disclosure also provide improved gastrointestinal adverse events rates over the previously described extended release formulations. When these extended release oral compositions are administered at an amantadine dose of 50 mg to 500 mg, or an equivalent amount of a pharmaceutically acceptable salt thereof, once nightly to a subject Parkinson's disease the compositions are well tolerated and provide improvements in Parkinson's symptoms, motor fluctuations, levodopa induced dyskinesia (LID), and provides an improvement in physician's Clinical Global Impression of Change (CGIC). The effectiveness measures for once nightly administration of the amantadine oral compositions described herein are superior to currently available formulations of amantadine, e.g., immediate release forms administered in divided doses. Additionally, the compositions of the present disclosure provide improved tolerability relative to known formulations, particularly when administered once daily and especially when administered once daily 0 to 4 hours before bedtime.

The present disclosure, in some aspects, provides an extended release oral composition comprising 50 mg to 500 mg, 60 mg to 400 mg, 60 mg to 300 mg, 137 mg to 500 mg, preferably 260 mg to 420 mg, of amantadine or a pharmaceutically acceptable salt thereof in the form of a composition described herein, and upon administration to subjects of a single dose, fasting human pharmacokinetic study provides a low incidence of gastrointestinal side effects including one or more of the following gastrointestinal disorders: abdominal distension, constipation, diarrhea, dyspepsia, gingival pain, dry lip, lower abdominal pain, nausea, stomach discomfort, toothache, upper abdominal pain, and vomiting. In some variations, the extended release oral composition comprises less than 6000 ppm organic solvent, for example less than 5500 ppm, less than 5000 ppm, less than 4500 ppm, less than 4000 ppm, less than 3500 ppm, less than 3000 ppm, less than 2500 ppm, less than 2000 ppm, less than 1500 ppm, or less than 1200 ppm organic solvent. In certain embodiments, the extended release oral composition comprises a plurality of core seeds, wherein each core seed is surrounded by a drug coating, and the plurality of coated core seeds comprises less than 6000 ppm, less than 5500 ppm, less than 5000 ppm, less than 4500 ppm, less than 4000 ppm, less than 3500 ppm, less than 3000 ppm, less than 2500 ppm, less than 2000 ppm, less than 1500 ppm, or less than 1200 ppm organic solvent. In some embodiments, the extended release oral composition comprises about 68.5 mg, about 137 mg, about 205.5 mg, or about 274 mg of amantadine. In certain embodiments, the extended release oral composition comprises from about 60 mg to about 80 mg, from about 120 mg to about 155 mg, from about 185 mg to about 230 mg, or from about 245 mg to about 305 mg of amantadine. In some embodiments, the extended release oral composition comprises about 85 mg, about 170 mg, about 255 mg, or about 340 mg of amantadine hydrochloride. In certain embodiments, the extended release oral composition comprises from about 75 mg to about 95 mg, from about 150 mg to about 190 mg, from about 230 mg to about 285 mg, or from about 305 to about 375 mg of amantadine hydrochloride.

In a second aspect, the disclosure provides a method of administering an extended release oral composition comprising 50 mg to 500 mg, 60 mg to 400 mg, 60 mg to 300 mg, 137 mg to 500 mg, preferably 260 mg to 420 mg, of amantadine, or an equivalent amount of a pharmaceutically acceptable salt thereof, to a human subject once daily, wherein the extended release oral composition is therapeutically effective for treatment of said subject and wherein the extended release oral composition has a low incidence of one or more of the aforementioned gastrointestinal side effects when administered to subjects of a fasted, single dose human pharmacokinetic study. In some embodiments, the single dose, fasted human pharmacokinetic study is dosed in the morning following an overnight fast. In some variations, the extended release oral composition comprises less than 6000 ppm organic solvent, for example less than 5500 ppm, less than 5000 ppm, less than 4500 ppm, less than 4000 ppm, less than 3500 ppm, less than 3000 ppm, less than 2500 ppm, less than 2000 ppm, less than 1500 ppm, or less than 1200 ppm organic solvent. In certain embodiments, the extended release oral composition comprises a plurality of core seeds, wherein each core seed is surrounded by a drug coating, and the plurality of coated core seeds comprises less than 6000 ppm, less than 5500 ppm, less than 5000 ppm, less than 4500 ppm, less than 4000 ppm, less than 3500 ppm, less than 3000 ppm, less than 2500 ppm, less than 2000 ppm, less than 1500 ppm, or less than 1200 ppm organic solvent. In some embodiments, the extended release oral composition comprises about 68.5 mg, about 137 mg, about 205.5 mg, or about 274 mg of amantadine, or an equivalent amount of a pharmaceutically acceptable salt thereof. In certain embodiments, the extended release oral composition comprises from about 60 mg to about 80 mg, from about 120 mg to about 155 mg, from about 185 mg to about 230 mg, or from about 245 mg to about 305 mg of amantadine, or an equivalent amount of a pharmaceutically acceptable salt thereof. In some embodiments, the extended release oral composition comprises about 85 mg, about 170 mg, about 255 mg, or about 340 mg of amantadine hydrochloride. In certain embodiments, the extended release oral composition comprises from about 75 mg to about 95 mg, from about 150 mg to about 190 mg, from about 230 mg to about 285 mg, or from about 305 to about 375 mg of amantadine hydrochloride.

In a third aspect, the disclosure provides a method of administering an extended release oral composition comprising 50 mg to 500 mg, 60 mg to 400 mg, 60 mg to 300 mg, 137 mg to 500 mg, preferably 260 mg to 420 mg, of amantadine, or an equivalent amount of a pharmaceutically acceptable salt thereof, to a human subject once daily, 0 to 4 hours before bedtime, wherein the extended release oral composition is therapeutically effective for treatment of said subject and wherein the extended release oral composition has a low incidence of one or more of the aforementioned gastrointestinal side effects when administered to subjects of a fasted, single dose human pharmacokinetic study. In some embodiments, the extended release oral composition comprises about 68.5 mg, about 137 mg, about 205.5 mg, or about 274 mg of amantadine, or an equivalent amount of a pharmaceutically acceptable salt thereof. In certain embodiments, the extended release oral composition comprises from about 60 mg to about 80 mg, from about 120 mg to about 155 mg, from about 185 mg to about 230 mg, or from about 245 mg to about 305 mg of amantadine, or an equivalent amount of a pharmaceutically acceptable salt thereof. In some embodiments, the extended release oral composition comprises about 85 mg, about 170 mg, about 255 mg, or about 340 mg of amantadine hydrochloride. In certain embodiments, the extended release oral composition comprises from about 75 mg to about 95 mg, from about 150 mg to about 190 mg, from about 230 mg to about 285 mg, or from about 305 to about 375 mg of amantadine hydrochloride.

In some embodiments of any of the aspects described herein, the extended release oral composition has a low incidence of sleep related adverse effects when administered to subjects of a fasted, single dose human pharmacokinetic study. In some embodiments of any of the aspects described herein, the extended release oral composition has a low incidence of sleep related adverse effects when administered at a therapeutically effective dose to subjects of a fasted, single dose human pharmacokinetic study. In some embodiments of any of the aspects described herein, the extended release oral composition has a low incidence of gastrointestinal adverse events when administered to subject of a fasted, single dose human pharmacokinetic study. In other embodiments of any of the aspects described herein, the extended release oral composition has a low incidence of both sleep related adverse events and gastrointestinal adverse events when administered at a therapeutically effective dose to subjects of a fasted, single dose human pharmacokinetic study. In some embodiments, a low incidence of gastrointestinal adverse events includes less than 12%, less than 10%, less than 8%, less than 7%, less than 6%, less than 5%, less than 4%, less than 3%, less than 2%, or less than 1% of the subjects of a fasted, single dose human pharmacokinetic study experiencing at least one gastrointestinal adverse event.

In some aspects of the disclosure, amantadine, or an equivalent amount of a pharmaceutically acceptable salt thereof (such as the hydrochloride), in the form of a composition described herein, is administered at 50 mg to 500 mg, 60 mg to 400 mg, 60 mg to 300 mg, 137 mg to 500 mg, preferably 209 mg to 339 mg once nightly, 0 to 4 hours before bedtime without sleep related adverse effects in a subject with Parkinson's disease, and one (or more) of the following: A. LID in the subject is significantly improved; B. the PD symptoms are improved; C. the Clinical Global Impression of Change is significantly improved (relative to placebo); and/or D. the Clinical Global Impression of Change is significant, whereas higher and lower doses are not significantly different from placebo. In some aspects of the disclosure, the dyskinesia metrics in A can be from UDysRS or some of other form of metrics, infra. In some embodiments, the extended release oral composition comprises about 68.5 mg, about 137 mg, about 205.5 mg, or about 274 mg of amantadine, or an equivalent amount of a pharmaceutically acceptable salt thereof. In certain embodiments, the extended release oral composition comprises from about 60 mg to about 80 mg, from about 120 mg to about 155 mg, from about 185 mg to about 230 mg, or from about 245 mg to about 305 mg of amantadine, or an equivalent amount of a pharmaceutically acceptable salt thereof. In some embodiments, the extended release oral composition comprises about 85 mg, about 170 mg, about 255 mg, or about 340 mg of amantadine hydrochloride. In certain embodiments, the extended release oral composition comprises from about 75 mg to about 95 mg, from about 150 mg to about 190 mg, from about 230 mg to about 285 mg, or from about 305 to about 375 mg of amantadine hydrochloride. In some embodiments, the amantadine is administered as amantadine hydrochloride at 260 mg to 420 mg. In certain embodiments, 340 mg amantadine hydrochloride is administered (i.e. equivalent to 274 mg amantadine).

In some aspects of the disclosure, amantadine, or an equivalent amount of a pharmaceutically acceptable salt thereof (such as the hydrochloride), in the form of a composition described herein, is administered at 50 mg to 500 mg, 60 mg to 400 mg, 60 mg to 300 mg, 137 mg to 500 mg, preferably 260 mg to 420 mg (more preferably 340 mg) once nightly, 0 to 4 hours before bedtime to a subject with Parkinson's disease, resulting in one or more of the following: A. the daily ON time without troublesome dyskinesia is increased relative to placebo; B. the daily ON time without dyskinesia is increased relative to placebo; C. the daily ON time with dyskinesia is decreased relative to placebo (or in a dose responsive manner); D. the daily ON time with troublesome dyskinesia is decreased relative to placebo (or in a dose responsive manner); and/or E. the daily OFF time is decreased relative to placebo and/or higher amantadine dosage strengths. Thus, in some embodiments, administration of this drug once nightly before bedtime provides marked improvement on following day measurements of efficacy (e.g., increase in ON time without dyskinesia, decrease in OFF time, improvement in dyskinesia) and/or tolerability. There is a need in the art for improved formulations, and methods of treatment with such formulations, of amantadine (or a pharmaceutically acceptable salt thereof) that result in a subject having higher plasma concentrations of amantadine upon waking in the morning with low incidence of gastrointestinal side effects and, preferably, without adversely affecting sleep compared with conventional amantadine therapy. In particular, there is a need in the art for a method of administering amantadine, or a pharmaceutically acceptable salt thereof, in the late afternoon or evening, e.g., after 4 pm, which reduces side effects of insomnia and sleep disturbance, provides a low incidence of gastrointestinal side effects and provides effective plasma concentrations of amantadine upon waking. In some embodiments, the extended release oral composition comprises about 68.5 mg, about 137 mg, about 205.5 mg, or about 274 mg of amantadine, or an equivalent amount of a pharmaceutically acceptable salt thereof. In certain embodiments, the extended release oral composition comprises from about 60 mg to about 80 mg, from about 120 mg to about 155 mg, from about 185 mg to about 230 mg, or from about 245 mg to about 305 mg of amantadine, or an equivalent amount of a pharmaceutically acceptable salt thereof. In some embodiments, the extended release oral composition comprises about 85 mg, about 170 mg, about 255 mg, or about 340 mg of amantadine hydrochloride. In certain embodiments, the extended release oral composition comprises from about 75 mg to about 95 mg, from about 150 mg to about 190 mg, from about 230 mg to about 285 mg, or from about 305 to about 375 mg of amantadine hydrochloride.

Therefore, there exists a need in the art for improved methods of amantadine therapy for the treatment of Parkinson's disease, LID in Parkinson's Disease, and the overall symptoms of Parkinson's Disease, including motor fluctuations, which can be administered to a subject shortly before they wish to sleep (e.g., at bedtime) without causing insomnia or sleep disturbance and provides a low incidence of gastrointestinal side effects. In addition, there is a need for an amantadine therapy which can be taken by the subject before they go to sleep and then provides a suitable plasma concentration of amantadine when they wake up, e.g., in the morning, after a full night's sleep. Furthermore, there is exists a need in the art for improved methods of treating walking disorders in subjects with Multiple Sclerosis, including, for example, methods of improving walking speed, improving overall mobility, and/or improving the ability to get up.

In some aspects of the disclosure, a method of administering amantadine to a subject in need thereof is provided, said method comprising orally administering an extended release (ER) oral composition comprising amantadine, or a pharmaceutically acceptable salt thereof, less than three hours before bedtime (e.g., the time at which the subject wishes to go to sleep). This aspect also includes the use of such compositions and the use of amantadine, or a pharmaceutically acceptable salt thereof, for the manufacture of a medicament as described herein. Alternatively, the composition is administered less than about 4 hours before bedtime. In some variations, the composition comprises less than 6000 ppm organic solvent. In certain variations, the composition comprises less than 5500 ppm, less than 5000 ppm, less than 4500 ppm, less than 4000 ppm, less than 3500 ppm, less than 3000 ppm, less than 2500 ppm, less than 2000 ppm, less than 1500 ppm, or less than 1200 ppm organic solvent. In some variations, the composition comprises a plurality of core seeds wherein each core seed is surrounded by a drug coating, and the plurality of coated core seeds comprises less than 6000 ppm organic solvent, less than 5500 ppm, less than 5000 ppm, less than 4500 ppm, less than 4000 ppm, less than 3500 ppm, less than 3000 ppm, less than 2500 ppm, less than 2000 ppm, less than 1500 ppm, or less than 1200 ppm organic solvent. In some variations, the organic solvent is an alcohol, such as isopropyl alcohol. In some embodiments, the organic solvent is a linear or cyclic ketone (e.g., acetone, methyl ethyl ketone, etc.) In some embodiments, the organic solvent is a sulfoxide (e.g., dimethyl sulfoxide, etc.). In some embodiments, the organic solvent is an amide (e.g., dimethyl formamide, N-methyl pyrrolidone, hexamethyl phosphorous triamide (HMPT), etc.). In some embodiments, the organic solvent is a linear or cyclic ether (e.g., tetrahydrofuran, diethyl ether, bis(2-methoxyethyl) ether (diglyme), dimethoxy ethane (glyme), 1,4-dioxane, etc.). In some embodiments, the organic solvent is a phosphoramide (e.g., hexamethyl phosphoramide (HPMA), etc.). In some embodiments, the organic solvent is a chlorinated hydrocarbon (e.g., chloroform, dichloromethane, dichloro ethane, carbon tetrachloride, etc.). In some embodiments, the organic solvent is a glycol (e.g., ethylene glycol, diethylene glycol, propylene glycol, etc.). In some embodiments, the organic solvent is a, nitrogen-containing solvent (e.g., pyridine, acetonitrile, etc.). In some embodiments, the organic solvent is an alcohol (e.g., a $C_1$-$C_6$ alcohol (e.g., ethanol, methanol, isopropanol, 1-butanol, 2-butanol, glycerol)), such as isopropyl alcohol. In some embodiments, mixtures of two or more solvents can be used. In some embodiments of the levels of organic solvent described herein, the provided level refers to the total amount of two or more organic solvents.

In some aspects, administration occurs less than two and a half, less than two, less than one and a half, less than one or less than half hour before bedtime.

In some aspects, the disclosure provides a method of reducing sleep disturbance in a human subject undergoing treatment with amantadine, said method comprising administering an extended release (ER) oral composition comprising amantadine, or a pharmaceutically acceptable salt thereof, less than about three hours before bedtime (e.g., the time at which the subject wishes to go to sleep). This aspect also includes the use of such compositions and the use of amantadine or a pharmaceutically acceptable salt thereof for the manufacture of a medicament as described herein. Alternatively, the composition is administered less than about 4 hours before bedtime.

In some aspects of the disclosure, amantadine, or a pharmaceutically acceptable salt thereof (such as the hydrochloride), in the form of a composition described herein, is administered at a reduced amount, e.g., 68.5 to 260 mg per day, or an equivalent amount of a pharmaceutically acceptable salt thereof, for at least one week prior to once daily administration of the maintenance dose. This titration period may improve tolerability of the maintenance dose. In some aspects of the disclosure, a subject is administered 68.5 or 137 mg per day of amantadine, or an equivalent amount of a pharmaceutically acceptable salt thereof, in the form of a composition described herein, for at least one week prior to increasing the dose to 137 or 274 mg per day, or an equivalent amount of a pharmaceutically acceptable salt thereof; in this aspect, the amantadine may be in the form of a pharmaceutically acceptable salt such as amantadine hydrochloride, and the amount of amantadine hydrochloride may be 85 or 170 mg per day for at least one week prior to increasing the dose to 170 or 340 mg per day. In some embodiments of methods including a titration period, and the oral pharmaceutical compositions for use in methods described herein, the subject has Parkinson's disease. In certain embodiments, the method comprises treating levodopa induced dyskinesia, or fatigue, or dementia, or any other symptom of Parkinson's disease. In certain embodiments, the method comprises decreasing OFF time, or increasing ON time without troublesome dyskinesia, or a combination thereof, in a subject with Parkinson's disease, wherein the subject is being treated with a Parkinson's medication. In some embodiments, the Parkinson's medication is levodopa. In certain embodiments, the Parkinson's medication comprises levodopa. In some embodiments, the Parkinson's medication comprises levodopa in combination with carbidopa. In other embodiments of methods including a titration period, and the oral pharmaceutical compositions for use in methods described herein, the subject has Multiple Sclerosis. In certain embodiments, the method comprises treating a hypokinetic disorder in a subject with Multiple Sclerosis. In some embodiments, the hypokinetic disorder is walking impairment. In some embodiments, treating a hypokinetic disorder comprises improving walking speed, improving walking ability, improving overall mobility, and/or improving the ability to get up.

In some aspects, the disclosure provides a method of treating levodopa induced dyskinesia, or fatigue, or dementia, or any other symptom of Parkinson's disease, said method comprising administering an extended release (ER) oral composition comprising amantadine, or a pharmaceutically acceptable salt thereof, less than about three hours before bedtime (e.g., the time at which the subject wishes to go to sleep). In other aspects, the disclosure provides a method of treating a hypokinetic disorder in a subject with Multiple Sclerosis, said method comprising administering an extended release (ER) oral composition comprising amantadine, or a pharmaceutically acceptable salt thereof, less than about three hours before bedtime. Also provided herein are oral pharmaceutical compositions for use in one or more of these methods. For example, in some aspects, provided herein is an oral pharmaceutical composition for use in treating levodopa induced dyskinesia in a subject with Parkinson's disease, or decreasing OFF time in a subject with Parkinson's disease, or decreasing ON time with troublesome dyskinesia in a subject with Parkinson's disease, or increasing ON time without troublesome dyskinesia in a subject with Parkinson's disease, or treating a hypokinetic disorder in subject with Multiple Sclerosis. These aspects also include the use of such compositions and the use of amantadine or pharmaceutically acceptable salt thereof for the manufacture of a medicament as described herein. In some aspects, the medicament comprises less than 6000 ppm organic solvent. In certain variations, the composition comprises less than 5500 ppm, less than 5000 ppm, less than 4500 ppm, less than 4000 ppm, less than 3500 ppm, less than 3000 ppm, less than 2500 ppm, less than 2000 ppm, less than 1500 ppm, or less than 1200 ppm organic solvent. In some variations, the medicament comprises a plurality of core seeds wherein each core seed is surrounded by a drug coating, and the plurality of coated core seeds comprises less than 6000 ppm, less than 5500 ppm, less than 5000 ppm, less than 4500 ppm, less than 4000 ppm, less than 3500 ppm, less than 3000 ppm, less than 2500 ppm, less than 2000 ppm, less than 1500 ppm, or less than 1200 ppm organic solvent. In some variations, the organic solvent is an alcohol, such as isopropyl alcohol. In some embodiments, the organic solvent is a linear or cyclic ketone (e.g., acetone, methyl ethyl ketone, etc.) In some embodiments, the organic solvent is a sulfoxide (e.g., dimethyl sulfoxide, etc.). In some embodiments, the organic solvent is an amide (e.g., dimethyl formamide, N-methyl pyrrolidone, hexamethyl phosphorous triamide (HMPT), etc.). In some embodiments, the organic solvent is a linear or cyclic ether (e.g., tetrahydrofuran, diethyl ether, bis(2-methoxyethyl) ether (diglyme), dimethoxy ethane (glyme), 1,4-dioxane, etc.). In some embodiments, the organic solvent is a phosphoramide (e.g., hexamethyl phosphoramide (HPMA), etc.). In some embodiments, the organic solvent is a chlorinated hydrocarbon (e.g., chloroform, dichloromethane, dichloroethane, carbon tetrachloride, etc.). In some embodiments, the organic solvent is a glycol (e.g., ethylene glycol, diethylene glycol, propylene glycol, etc.). In some embodiments, the organic solvent is a, nitrogen-containing solvent (e.g., pyridine, acetonitrile, etc.). In some embodiments, the organic solvent is an alcohol (e.g., a $C_1$-$C_6$ alcohol (e.g., ethanol, methanol, isopropanol, 1-butanol, 2-butanol, glycerol)), such as isopropyl alcohol. In some embodiments, mixtures of two or more solvents can be used. In some embodiments of the levels of organic solvent described herein, the provided level refers to the total amount of two or more organic solvents.

In some aspects, the disclosure provides a method of treating brain injury, brain trauma, dementia, Alzheimer's disease, stroke, Huntington's disease, ALS, Multiple Sclerosis, neurodegenerative diseases, dementias, cerebrovascular conditions, movement disorders, cranial nerve disorders, neuropsychiatric disorders, said method comprising administering to a subject certain extended release (ER) oral compositions comprising amantadine, or a pharmaceutically acceptable salt thereof, less than about three hours before bedtime (e.g., the time at which the subject wishes to go to sleep). This aspect also includes methods of treating symptoms associated with the aforementioned disorders including hypokinetic disorders such as walking impairment in Multiple Sclerosis. This aspect also includes the use of such compositions and the use of amantadine or a pharmaceutically acceptable salt thereof for the manufacture of a medicament as described herein.

In some embodiments of any of the aspects herein, administration occurs less than two and a half, less than two, less than one and a half, less than one or less than half hour before bedtime (e.g., the time at which the subject wishes to go to sleep).

In some embodiments of any of the aspects herein, the subject has been diagnosed with Parkinson's disease. In some embodiments, the subject has been diagnosed with Multiple Sclerosis.

In some embodiments of any of the aspects herein, the composition is administered once nightly.

In other embodiments, the daily dose of amantadine is from 50 mg to 500 mg, 60 mg to 400 mg, 60 mg to 300 mg, 137 to 274 mg (preferably 274 mg), or an equivalent amount of a pharmaceutically acceptable salt thereof. In some embodiments, the daily dose is 60 mg to 340 mg, or 170 to 340 mg of amantadine hydrochloride, or an equivalent amount of a different pharmaceutically acceptable salt thereof, and is given in 1, 2 or 3 capsules of size 0, 1 or 2, in normal and/or EL formats (e.g., sizing system for capsules).

In certain embodiments, the daily dose of amantadine is about 68.5 mg, about 137 mg, about 205.5 mg, or about 274 mg, or an equivalent amount of a pharmaceutically acceptable salt thereof. In certain embodiments, the daily dose of amantadine is from about 60 mg to about 80 mg, from about 120 mg to about 155 mg, from about 185 mg to about 230 mg, or from about 245 mg to about 305 mg, or an equivalent amount of a pharmaceutically acceptable salt thereof. In still other embodiments, the daily dose is about 85 mg, about 170 mg, about 255 mg, or about 340 mg of amantadine hydrochloride. In certain embodiments, the daily dose is from about 75 mg to about 95 mg, from about 150 mg to about 190 mg, from about 230 mg to about 285 mg, or from about 305 to about 375 mg of amantadine hydrochloride. In any of these embodiments, the dose may, in some embodiments, be is given in 1, 2, or 3 capsules of size 0, 1 or 2, in normal and/or EL formats (e.g., sizing system for capsules).

In some embodiments of any of the aspects herein, administration of the composition to a subject with Parkinson's disease results in a significant reduction in levodopa induced dyskinesia (LID). In a specific embodiment, administration of the composition results in about 20%, 25%, 30%, 35%, 40%, 45%, 50%, 55%, 60%, 65%, 70%, 75% or 80% reduction in levodopa induced dyskinesia. In further embodiments, the reduction in levodopa induced dyskinesia is measured on a numeric scale that is used by the FDA to evaluate effectiveness of drugs indicated to reduce LID. In further specific embodiments, the scale used in measuring the reduction in LID could be UDysRS, UPDRS Part IV (subscores 32, 33), MDS-UPDRS Part IV and subscores 4.1 and 4.2, Dyskinesia Rating Scale (DRS), Abnormal Involuntary Movement Scale (AIMS), or other scales developed for this purpose.

In some embodiments of any of the aspects herein, administration of the oral composition to a subject with Parkinson's disease results in a significant reduction in Parkinson's disease symptoms, including motor fluctuations. In a specific embodiment, administration of the composition results in about 5%, 10%, 15%, 20%, 25%, 30%, 35%, or 40% reduction in Parkinson's symptoms, including motor fluctuations. In further specific embodiments, the reduction in Parkinson's symptoms is measured on a numeric scale that is used by the FDA to evaluate effectiveness of drugs indicated to reduce Parkinson's symptoms, including motor fluctuations. In further specific embodiments, the scale used in measuring the reduction in Parkinson's symptoms, including motor fluctuations, could be the Unified Parkinson's Disease Rating Scale (UPDRS), MDS-UPDRS, or analysis of PD Diary data (for motor fluctuations).

In some embodiments of any of the aspects herein, administration of the oral composition to a subject results in a significant improvement in Clinician Global Impression (CGI) or any other physician measurement of a subject's overall condition. In a specific embodiment, administration of the composition results in about 5%, 10%, 15%, 20%, 25%, 30%, 35%, or 40% improvement in CGI. In further specific embodiments, the improvement in CGI is measured on a numeric scale that is used by the FDA to evaluate effectiveness of drugs indicated to treat CNS disorders.

In still further embodiments, provided herein is a method of, and an oral pharmaceutical composition for use in, reducing OFF time in a subject with Parkinson's disease, wherein the subject is being treated with a Parkinson's medication, comprising administering to the subject an oral pharmaceutical composition as described herein. In some embodiments, the total daily amount of OFF time is reduced by at least 10%, at least 20%, at least 30%, at least 40%, at least 50%, at least 60%, or at least 70%. In some embodiments, OFF time is reduced relative to a placebo, as evaluated in a placebo-controlled double blind clinical study. In other embodiments, OFF time is reduced relative to the OFF time of the subject before beginning administering of the oral pharmaceutical composition.

In still other embodiments, provided herein is a method of, and an oral pharmaceutical composition for use in, increasing ON time without troublesome dyskinesia in a subject with Parkinson's disease, wherein the subject is being treated with a Parkinson's medication, comprising administering to the subject a pharmaceutical composition as described herein. In some embodiments, the total daily amount of ON time without troublesome dyskinesia is increased at least 10%, at least 20%, at least 30%, at least 40%, at least 50%, at least 60%, or at least 70%. In some embodiments, ON time without troublesome dyskinesia is increased relative to a placebo, as evaluated in a placebo-controlled double blind clinical study. In other embodiments, ON time without troublesome dyskinesia is increased relative to the ON time without troublesome dyskinesia of the subject before beginning administering of the oral pharmaceutical composition.

In some embodiments of the methods of, and an oral pharmaceutical composition for use in, treating a hypokinetic disorder in a subject with Multiple Sclerosis provided herein, walking speed is improved, walking ability is improved, overall mobility is improved, or the ability to get up is improved, or any combinations thereof. In some embodiments, administration of a composition as described herein to a subject with Multiple Sclerosis results in a 5%, 10%, 15%, 20%, 25%, 30%, 35%, 40%, 45%, 50%, 55%, or 60% improvement in one or more of walking speed, walking ability, overall mobility, or ability to get up. Overall mobility may include, for example, the total amount of walking over the course of a day, or ability to get up at one or more times over the course of a day, or combinations thereof. In some embodiments, walking speed, walking ability, overall mobility, or ability to get up is evaluated via at least one of the following or a combination thereof: Timed 25-Foot Walking test (T25FW), Timed Up and Go (TUG), 2 minute walk test, six minute timed walk test (6MTW), and/or, Twelve Item Multiple Sclerosis Walking Scale (MSWS-12). In some embodiments, the T25FW, TUG, 2 minute walk, 6MTW and/or MSWS-12 is significantly improved relative to placebo, as evaluated in a placebo-controlled double blind clinical trial. In other embodiments, the T25FW, TUG, 2 minute walk, 6MTW and/or MSWS-12 is significantly improved in the subject relative to before beginning administration of the composition as described herein. In some embodiments, the reduction walking impairment is measured on a numeric scale that is used by or accepted by the FDA or other regulatory agencies to evaluate the effectiveness of and to approve for licensure drugs for the treatment of walking impairment. In some embodiments, administration of the composition results in about 5%, 10%, 15%, 20%, 25%, 30%, 35%, 40%, 45%, 50%, 55%, or 60% improvement in one or more of the assessment scores described herein.

In some embodiments of any of the aspects herein, there is no increase in plasma concentration of amantadine for at least one hour after the administration at steady state plasma concentrations.

In some embodiments of any of the aspects herein, there is no increase in the plasma concentration of amantadine for at least two hours after the administration at steady state plasma concentrations.

In some embodiments of any of the aspects herein, the administration of the oral composition to a human subject at steady state amantadine plasma concentrations increases the amantadine plasma concentration by less than 5%, 10%, 15%, 20% or 25% at 1, 2, 2.5 or 3 hours following such administration. For example, administration of the composition to a human subject at steady state amantadine plasma concentrations increases the amantadine plasma concentration by less than 5% at 1, 2, 2.5 or 3 hours following such administration; or by less than 10% at 1, 2, 2.5 or 3 hours following such administration; or by less than 15% at 1, 2, 2.5 or 3 hours following such administration; or by less than 20% at 1, 2, 2.5 or 3 hours following such administration; or by less than 25% at 1, 2, 2.5 or 3 hours following such administration.

In some embodiments of any of the aspects herein, the amantadine has a single dose Tmax of 11 to 19 hours. In more specific embodiments, the amantadine has a single dose Tmax of 11 to 18 hours after administration. In some embodiments, the Tmax for amantadine is 11, 12, 13, 14 hours to 15, 16, 17, 18, 19 hours after administration to a healthy subject of a single dose, fasting human pharmacokinetic study.

In some embodiments of any of the aspects herein, the amantadine has a steady state Tmax of 7 to 16 hours. In certain embodiments, the amantadine has a steady state Tmax of 7 to 14 hours after administration. In other embodiments, the amantadine has a steady state Tmax of 8 to 12 hours after administration. In some embodiments, the steady state Tmax is the median value obtained from a multi dose, fasting human pharmacokinetic study in healthy subjects.

In some embodiments of any of the aspects described herein, at least 80%, preferably at least 90%, of the amantadine or pharmaceutically acceptable salt thereof is released from the composition upon administration to a subject of a single dose, fasting human pharmacokinetic study as determined from bioavailability relative to an immediate release oral formulation of the same drug substance at a similar dose.

In some embodiments of any of the aspects described herein, the $AUC_{inf}$ for amantadine for the compositions of the present disclosure is 40, 41, 42, 43, 44, or 45 to 64, 66, 68, 70, or 72 ng*hr/ml per mg of drug of the composition as determined by administration of the composition to a subject of a single dose, fasting human pharmacokinetic study. In some embodiments, compositions will have an $AUC_{inf}$ of 42 to 72 ng*hr/ml per mg of drug of the composition as determined by administration of the composition to a subject of a single dose, fasting human pharmacokinetic study. In certain embodiments, compositions will have an $AUC_{inf}$ of 44 to 72 ng*hr/ml per mg of drug of the composition as determined by administration of the composition to a subject of a single dose, fasting human pharmacokinetic study.

In some embodiments described herein, the $pAUC_{0-6}$ for amantadine for the compositions of the present disclosure is less than or equal to 1.0 ng*hr/ml per mg of drug of the composition as determined by administration of the composition to a subject of a single dose, fasting human pharmacokinetic study. Preferably the $pAUC_{0-6}$ for amantadine for the composition is 0.1, 0.2, 0.3, 0.4, or 0.5 to 0.6, 0.7, 0.8, 0.9, or 1.0 ng*hr/ml per mg of drug of the composition as determined by administration of the composition to a subject of a single dose, fasting human pharmacokinetic study. More preferably, the $pAUC_{0-6}$ for amantadine for the composition is 0.3 to 0.9 ng*hr/ml per mg of drug of the composition as determined by administration of the composition to a subject of a single dose, fasting human pharmacokinetic study.

In some embodiments described herein, the $pAUC_{0-8}$ for amantadine for the compositions of the present disclosure is less than or equal to 2.0 ng*hr/ml per mg of drug of the composition as determined by administration of the composition to a subject of a single dose, fasting human pharmacokinetic study. Preferably the $pAUC_{0-8}$ for amantadine for the composition is 1.0, 1.1, 1.2, 1.3, or 1.4 to 1.8, 1.9, 2.0, 2.1, 2.2, 2.3, or 2.4 ng*hr/ml per mg of drug of the composition as determined by administration of the composition to a subject of a single dose, fasting human pharmacokinetic study. More preferably, the $pAUC_{0-8}$ for amantadine for the composition is 1.0 to 2.0 ng*hr/ml per mg of drug of the composition as determined by administration of the composition to a subject of a single dose, fasting human pharmacokinetic study.

In some embodiments of any of the aspects herein, a once nightly oral administration of the composition to a human subject provides a steady state plasma concentration profile characterized by a concentration increase of amantadine of less than 25% at three hours after the administration. In more specific embodiments, the steady state plasma concentration profile is characterized by a concentration increase of amantadine of less than 25% at four hours after the administration.

In some embodiments of any of the aspects herein, the composition is administered once a day and the ratio of Cmax to Cmin at steady state is 1.3 to 1.8, or, more specifically, 1.4 to 1.7, or, more specifically, about 1.6.

In embodiments of any of the aspects herein, the steady state plasma concentration profile following multiple administrations to a human subject of the composition at bedtime is characterized by an average plasma concentration during the day ("C-ave-day", defined as the average day time amantadine plasma concentration as measured in a human PK study) that is 1.2 to 1.7 times the average plasma concentration during the night ("C-ave-night", defined as the average night time amantadine plasma concentration as measured in a human PK study). In more specific embodiments the C-ave-day is the average amantadine plasma concentration as measured between the hours of 5 am, 6 am, 7 am, 8 am or 9 am to the hours of 4 pm, 5 pm, 6 pm, 7 pm or 8 pm; for example, between the hours of 6 am and 4 pm, between the hours of 6 am and 4 pm, between the hours of 7 am and 6 pm, or between the hours of 7 am and 5 pm. The C-ave-night is the average amantadine plasma concentration as measured between the hours of 4 pm, 5 pm, 6 pm, 7 pm, 8 pm, 9 pm, 10 pm or 11 pm to the hours of 5 am, 6 am, 7 am, 8 am or 9 am; for example, between the hours of 8 pm and 5 am, between the hours of 10 pm and 6 am, between the hours of 7 pm and 6 am, or between the hours of 8 pm and 6 am.

In some embodiments of any of the aspects herein the amantadine is administered as a pharmaceutically acceptable salt, preferably as amantadine hydrochloride.

In some embodiments of any of the aspects herein, administration of a single dose of the composition to a human subject provides a plasma concentration profile characterized by: a fractional AUC from 0 to 4 hours that is less than 1%, preferably less than 0.5%, more preferably less than 0.3%, and most preferably less than 0.2% of $AUC_{0-inf}$; a fractional AUC from 0 to 8 hours that is not more than 4.5%, preferably 1.0% to 4.0%, more preferably 1.5% to 3.75%, and most preferably 1.75% to 3.5% of $AUC_{0-inf}$; a fractional AUC from 0 to 12 hours that is about 5% to 15%, and preferably about 7.0% to 12.0% of $AUC_{0-inf}$; a fractional AUC from 0 to 18 hours that is about 20% to 35%, and preferably about 22.5% to 27.5% of $AUC_{0-inf}$; and a fractional AUC from 0 to 24 hours that is about 34% to 48%, and preferably about 36% to 44% of $AUC_{0-inf}$. In some embodiments, the subject is a subject in a single dose, fasted human pharmacokinetic study. In some embodiments, the single dose, fasted human pharmacokinetic study is dosed in the morning following an overnight fast.

In some embodiments of any of the aspects described herein, the once nightly dose of amantadine in the form of a composition described herein, may be in the range of 68.5 mg to 500 mg, or an equivalent range of a pharmaceutically acceptable salt thereof. Preferably, the dose of amantadine is 50 mg to 500 mg, 60 mg to 400 mg, 60 mg to 300 mg, 137 mg to 403 mg, or an equivalent amount of a pharmaceutically acceptable salt thereof. More preferably, the dose of amantadine is 68.5 mg to 274 mg, or 137 mg to 274 mg, or an equivalent amount of a pharmaceutically acceptable salt thereof. Alternatively the dose of amantadine hydrochloride is 60 mg to 340 mg, or 170 mg to 340 mg. In other embodiments, the once nightly dose of amantadine exceeds 340 mg per day, or an equivalent amount of a pharmaceutically acceptable salt thereof, e.g., the dose of amantadine is between 340 and 500 mg per day, more specifically is between 410 and 480 mg per day, or an equivalent amount of a pharmaceutically acceptable salt thereof. In other embodiments, the once nightly dose of a pharmaceutically acceptable salt of amantadine, for example amantadine hydrochloride, exceeds 340 mg per day, e.g., the dose of the pharmaceutically acceptable salt is between 340 and 500 mg per day, more specifically is between 410 and 480 mg per day. In various specific embodiments, the daily dose of amantadine may be 50 to 75 mg, 70 to 95 mg, 90 to 115 mg, 110 to 135 mg, 130 to 155 mg, 150 to 175 mg, 170 to 195 mg, 190 to 215 mg, 210 to 235 mg, 230 to 255 mg, 250 to 275 mg, 270 to 295 mg, 290 to 305 mg, 300 to 315 mg, 310 to 325 mg, 320 to 335 mg, 330 to 345 mg, 340 to 355 mg, 350 to 365 mg, 360 to 375 mg, 370 to 385 mg, 380 to 395 mg, 390 to 405 mg, 400 to 415 mg, 410 to 425 mg, 420 to 435 mg, 430 to 445 mg or 440 to 455 mg, or an equivalent amount of a pharmaceutically acceptable salt thereof. In still further embodiments, the once daily dose of amantadine is about 68.5 mg, about 137 mg, about 205.5 mg, or about 274 mg or an equivalent amount of a pharmaceutically acceptable salt thereof. In certain embodiments, the once daily dose is from about 60 mg to about 80 mg, from about 120 mg to about 155 mg, from about 185 mg to about 230 mg, or from about 245 mg to about 305 mg of amantadine, or an equivalent amount of a pharmaceutically acceptable salt thereof. In some embodiments, the once daily dose is about 85 mg, about 170 mg, about 255 mg, or about 340 mg of amantadine hydrochloride. In certain embodiments, once daily dose is from about 75 mg to about 95 mg, from about 150 mg to about 190 mg, from about 230 mg to about 285 mg, or from about 305 mg to about 375 mg of amantadine hydrochloride.

In some embodiments of any of the aspects herein, the composition comprises 50 mg to 500 mg of amantadine, or an equivalent amount of a pharmaceutically acceptable salt thereof. More specifically, the composition may comprise 100 mg to 450 mg of amantadine, or an equivalent amount of a pharmaceutically acceptable salt thereof. Still more specifically, the composition may comprise 130 mg to 210 mg of amantadine, or an equivalent amount of a pharmaceutically acceptable salt thereof. In various specific embodiments, a dosage form containing the composition comprises 50 to 75 mg, 70 to 95 mg, 90 to 115 mg, 110 to 135 mg, 130 to 155 mg, 150 to 175 mg, 170 to 195 mg, 190 to 215 mg, 210 to 235 mg, 230 to 255 mg, 250 to 275 mg, 270 to 295 mg, 290 to 305 mg, 300 to 315 mg, 310 to 325 mg, 320 to 335 mg, 330 to 345 mg, 340 to 355 mg, or 350 to 365 mg of amantadine, or an equivalent amount of a pharmaceutically acceptable salt thereof. In some embodiments, the once nightly dose of a pharmaceutically acceptable salt of amantadine is 340 mg, in the form of a composition described herein. In still further embodiments, a dosage form of the composition comprises from about 60 mg to about 80 mg, from about 120 mg to about 155 mg, from about 185 mg to about 230 mg, from about 245 mg to about 305 mg, about 68.5 mg, about 137 mg, about 205.5 mg, or about 274 mg of amantadine, or an equivalent amount of a pharmaceutically acceptable salt thereof. In certain embodiments, a dosage form of the composition comprises from about 75 mg to about 95 mg, from about 150 mg to about 190 mg, from about 230 mg to about 285 mg, from about 305 to about 375 mg, about 85 mg, about 170 mg, about 255 mg, or about 340 mg of amantadine hydrochloride.

In some embodiments of any of the aspects described herein, the once nightly oral composition is administered as one, two, three or four unit dosage forms in unequally or, preferably, equally divided units. In some more specific embodiments, the composition is administered as two or three unit dosage forms each comprising 68.5 to 175 mg amantadine, or an equivalent amount of a pharmaceutically acceptable salt thereof. In certain embodiments, the composition is administered as two or three unit dosage forms each comprising from about 60 mg to about 175 mg, or from about 60 mg to about 155 mg, or from about 60 mg to about 80 mg of amantadine, or an equivalent amount of a pharmaceutically acceptable salt thereof.

In some embodiments of any of the aspects herein, the composition is administered as two or three unit dosage forms of unequal, or preferably equal, dosage, each comprising 68.5 to 250 mg amantadine, or an equivalent amount of a pharmaceutically acceptable salt thereof. In some more specific embodiments, the composition is administered as two unit dosage forms each comprising 150 to 180 mg amantadine, or an equivalent amount of a pharmaceutically acceptable salt thereof. In still further embodiments, the composition is administered as two unit dosage forms each comprising 150 to 180 mg of a pharmaceutically acceptable salt of amantadine.

In some embodiments of any of the aspects herein, oral administration of a single dose of the composition to a cohort of human healthy volunteer subjects in a fasted state provides an average maximum plasma concentration (Cmax) for amantadine of 1.1 to 2.3 ng/ml per mg of amantadine or pharmaceutically acceptable salt thereof. In more specific embodiments, oral administration of a single dose of the composition to a cohort of human subjects in a fasted state provides an average maximum plasma concentration (Cmax) for amantadine of 1.2 to 2.0 ng/ml per mg of amantadine or pharmaceutically acceptable salt thereof and an $AUC_{0-inf}$ (Area under the concentration-curve curve from t=0 to t=infinity) for amantadine of 42 to 72 ng*h/mL per mg of amantadine or pharmaceutically acceptable salt thereof.

In some embodiments of any of the aspects herein, the daily oral administration of a dose of the composition to a cohort of human subjects provides a steady state plasma concentration profile characterized by at least one of: (i) a mean Cmax for amantadine of 2.2 to 3.6 ng/ml per mg of amantadine or pharmaceutically acceptable salt thereof, (ii) a mean Cmin for amantadine of 1.4 to 2.0 ng/ml per mg of amantadine or pharmaceutically acceptable salt thereof, and (iii) a mean $AUC_{0-24}$ of 46 to 72 ng*h/mL per mg of amantadine or pharmaceutically acceptable salt thereof. In more specific examples, all three criteria of (i), (ii) and (iii) are met.

In more specific embodiments, the steady state plasma concentration profile is further characterized by: (iv) no increase in concentration of amantadine for at least one hour after the administration; and (v) Cmax/Cmin ratio of 1.4 to 2.0. In more specific embodiments, both criteria of (iv) and (v) are met.

In some embodiments of any of the aspects herein the composition has an in vitro dissolution profile of amantadine or a pharmaceutically acceptable salt thereof which shows at least one of (i) not more than 10% dissolution at 2 hours, (ii) 5% to 13% dissolution at 4 hours, (iii) 20% to 43% dissolution at 6 hours, (iv) 50% to 70% dissolution at 8 hours, and (v) at least 80% dissolution at 12 hours, using a USP Apparatus II (Paddles) at 50 rpm with 500 ml water at 37.0±0.5° C. as the dissolution medium. In a more specific embodiment two of criteria (i), (ii), (iii), (iv) and (v) are met. In a more specific embodiment, three of criteria (i), (ii), (iii), (iv) and (v) are met. In a more specific embodiment, four of criteria (i), (ii), (iii), (iv) and (v) are met. And in an even more specific embodiment, all five of criteria (i), (ii), (iii), and (iv) are met. In some embodiments, criteria (i), (iii), (iv) and (v) are met.

In some embodiments of any of the aspects herein the composition has an in vitro dissolution profile of amantadine, or a pharmaceutically acceptable salt thereof, which shows at least one of (i) not more than 9% dissolution at 2 hours, (ii) 3% to 14% dissolution at 4 hours, (iii) 20% to 43% dissolution at 6 hours, (iv) 45% to 70% dissolution at 8 hours, and (v) at least 82% dissolution at 12 hours, using a USP Apparatus II (Paddles) at 50 rpm with 500 ml water at 37.0±0.5° C. as the dissolution medium. In a more specific embodiment two of criteria (i), (ii), (iii), (iv) and (v) are met. In a more specific embodiment, three of criteria (i), (ii), (iii), (iv) and (v) are met. In certain embodiments, four of criteria (i), (ii), (iii), (iv) and (v) are met. And in an even more specific embodiment, all five of criteria (i), (ii), (iii), and (iv) are met. In some embodiments, criteria (i), (iii), (iv) and (v) are met. In another aspect, the present disclosure provides an oral pharmaceutical composition comprising a plurality of coated core seeds and a capsule shell, wherein the coated core seeds are encapsulated within the capsule shell, and wherein the coated core seeds comprise a core seed comprising an inert material; a drug coating comprising amantadine or a pharmaceutically acceptable salt thereof and a binder; and an extended release coating surrounding the drug coating, wherein the drug coating comprises ethyl cellulose, a pore forming agent such as hydroxypropyl methyl cellulose or povidone, and a plasticizer. In some embodiments of this aspect, the amantadine and binder drug coating is prepared and applied to the core seed without the use of organic solvents.

In another aspect, the present disclosure provides an oral pharmaceutical composition for use in the methods of the aspects described herein, wherein said composition is for oral administration and comprises a capsule for oral administration, said capsule comprising a plurality of coated core seeds comprising: (a) a core seed, (b) a drug coating surrounding the core seed, wherein the drug coating comprises amantadine, or a pharmaceutically acceptable salt thereof, and (c) an extended release coating surrounding the drug coating. In some embodiments of this aspect, the drug coating comprises amantadine or a pharmaceutically acceptable salt thereof and one or more binders, and the drug coating is prepared and applied to the core seed without the use of organic solvents.

In some embodiments, the extended release coating comprises ethyl cellulose and at least one of povidone and hydroxypropyl methyl cellulose, and a plasticizer. In a more specific embodiment, the extended release coating comprises ethyl cellulose, povidone, and a plasticizer.

In some embodiments, the drug coating comprises amantadine and a binder, and surrounds the core seed. In some embodiments, the core seed is a sugar sphere (nonpareil) or microcrystalline cellulose seed (e.g. Celphere®). In a more specific embodiment, the core seed is a microcrystalline cellulose core. In another specific embodiment, the core seed has a diameter in the range of 100 microns to 1,000 microns. In additional specific embodiments, the core seed has a diameter of 100, 200, 300, 400, 500, 600 or 700 microns. In additional specific embodiments, 90% or more of the core seeds of the composition have a diameter of 100 to 200 microns, 150 to 250 microns, 200 to 300 microns, 250 to 350 microns, 300 to 400 microns, 350 to 450 microns, 400 to 500 microns, 500 to 600 microns, 550 to 650 microns, 600 to 700 microns. In some embodiments, the core seed has a diameter of less than 500 microns.

In some embodiments, based on the combined weight of the core seed, the drug coating, and the extended release coating, the amantadine, or a pharmaceutically acceptable salt thereof, is present in amounts from 20 to 80 wt %, with a bulk density of 0.3 to 1.2 $g/cm^3$.

In some embodiments, based on the combined weight of the core seed, the drug coating, and the extended release coating, the amantadine, or a pharmaceutically acceptable salt thereof, is present in amounts from 40 to 60 wt %, with a bulk density of 0.5 to 1.2 $g/cm^3$.

In some embodiments, based on the combined weight of the core seed, the drug coating, and the extended release coating, the amantadine, or a pharmaceutically acceptable salt thereof, is present in amounts from 60 to 80 wt %, with a bulk density of 0.5 to 1.2 $g/cm^3$.

In some embodiments, based on the combined weight of the core seed, the drug coating, and the extended release coating, the binder is present in amounts from 8 to 25 wt %, In some embodiments, based on the combined weight of the core seed, the drug coating, and the extended release coating, the core seed is present in amounts from 8 to 25 wt %, In some embodiments, based on the combined weight of the core seed, the drug coating, and the extended release coating, the ethyl cellulose is present in amounts from 10 to 24 wt %, In some embodiments, based on the combined weight of the core seed, the drug coating, and the extended release coating, the povidone is present in amounts from 1 to 4 wt %, In some embodiments, based on the combined weight of the core seed, the drug coating, and the extended release coating, the plasticizer is present in amounts from 1 to 4 wt %.

In some embodiments, the coated core seeds have an average diameter in the range of 200 microns to 1700 microns. In additional specific embodiments, the coated core seeds have an average diameter of 200, 300, 400, 500, 600, 700, 800, 900, 1000, 1100, 1200, 1300 or 1500 microns. In additional embodiments, the coated core seeds have an average diameter ranging from 200, 300, 400, 500, 600, 700, 800, 900 microns to 400, 500, 600, 700, 800, 900, 1000, 1100, 1200, 1300, 1400, or 1500 microns. In certain specific embodiments, the coated core seeds have an average diameter of less than 1000 microns, e.g., from 500 to 1000 microns.

In some embodiments, the coated core seeds further comprise a seal coating surrounding the drug coating, wherein the extended release coating surrounds the seal coating. In some embodiments, an inert coating can be applied to the inert core seed prior to drug coating or on drug-coated core seeds or on extended release coated core seeds. In another embodiment, an enteric coating can be applied to the drug coated core seeds or extended release coated core seeds.

In some embodiments, the drug coating comprises a binder, selected from the group consisting of hydroxypropyl methyl cellulose, copovidone, and mixtures thereof.

In some embodiments, the composition described herein is provided in a size 3, size 2, size 1, size 0 or size 00 capsules in normal and/or EL formats.

In some embodiments, the therapeutically effective daily dose of the composition described herein is administered in no more than two capsules. In another embodiment, the therapeutically effective daily dose of the composition is administered in no more than three size 1 capsules. In another embodiment, the therapeutically effective daily dose of the composition is administered in no more than two size 0 capsules. In yet other embodiments, the therapeutically effective daily dose of the composition is administered in no more than two size 1 capsules. In another embodiment, the therapeutically effective daily dose of the composition is administered in no more than three size 2 capsules.

In some embodiments, the composition described herein is provided in an amount of 50 to 110 mg of amantadine or an equivalent amount of a pharmaceutically acceptable salt thereof in a size 2 capsule, and in the amount of 110 mg to 210 mg of amantadine or an equivalent amount of a pharmaceutically acceptable salt thereof in a size 1 capsule. In additional embodiments, the composition described herein comprises coated core seeds of diameter 300 to 1000 microns, with amantadine or pharmaceutically acceptable salt thereof content of 40-80% wt % and at a bulk density of 0.5-1.2 g/cm$^3$. In certain embodiments, the composition described herein has an in vitro dissolution profile of amantadine which shows at least one of (i) not more than 10% dissolution in 2 hours, (ii) 5% to 13% dissolution in 4 hours, (iii) 20% to 43% dissolution at 6 hours, (iv) 45% to 70% dissolution in 8 hours, and (v) at not less than 82% dissolution in 12 hours, using a USP Apparatus II (Paddles) at 50 rpm with 500 ml water at 37.0±0.5° C. as the dissolution medium. In a more specific embodiment two of criteria (i), (ii), (iii), (iv) and (v) are met. In some embodiments, three of criteria (i), (ii), (iii), (iv) and (v) are met. In a more specific embodiment, four of criteria (i), (ii), (iii), (iv) and (v) are met. In an even more specific embodiment, all five of criteria (i), (ii), (iii), (iv) and (v) are met. In certain embodiments, criteria (i), (iii), (iv) and (v) are met.

In some embodiments, the plasticizer is selected from the group consisting of medium chain triglycerides, diethyl phthalate, citrate esters, polyethylene glycol, glycerol, acetylated glycerides, and castor oil. In certain embodiments, the plasticizer is medium chain triglycerides, e.g. Miglyol 812 N.

In other embodiments, the present disclosure provides method of treating Parkinson's disease and/or LID in a human subject in need thereof, said method comprising orally administering a composition of any of the aspects herein. In certain embodiments, the present disclosure provides a method of treating disease in a human subject in need thereof, said method comprising orally administering a composition of any of the aspects herein once nightly at nighttime, administering 1, 2 or 3 dosage forms.

References to administering amantadine or a pharmaceutically acceptable salt thereof to a subject in need thereof include treating a subject with a disease or condition, including an iatrogenic condition (e.g., LID), which may be treated, prevented or cured by a NMDA antagonist. More specifically, administering amantadine or a pharmaceutically acceptable salt thereof to a subject in need thereof includes treating a subject diagnosed with Parkinson's Disease, brain injury, brain trauma, dementia, Alzheimer's disease, stroke, Huntington's disease, ALS, Multiple Sclerosis, neurodegenerative diseases, dementias, cerebrovascular conditions, movement disorders, cranial nerve disorders, neuropsychiatric disorders and other CNS disorders.

Some embodiments described herein provide a method of improving CGI in a subject with Parkinson's disease, comprising administering to said subject once nightly, 0 to 4 hours before bedtime a composition comprising 260 to 420 mg amantadine, or an equivalent amount of a pharmaceutically acceptable salt thereof, and at least one release modifying excipient. In some embodiments, the composition comprises 260 to 340 mg amantadine, or an equivalent amount of a pharmaceutically acceptable salt thereof. In some embodiments, the composition comprises 260 mg amantadine, or an equivalent amount of a pharmaceutically acceptable salt thereof. In some embodiments, the composition comprises 340 mg of a pharmaceutically acceptable salt of amantadine. In some embodiments, the change in CGI is determined in a placebo controlled, double blind clinical study. Also provided is an oral pharmaceutical composition as described herein for use in improving CGI in a subject with Parkinson's disease, comprising administering to said subject once nightly, 0 to 4 hours before bedtime.

Some embodiments described herein provide a method resulting in at least one, preferably at least two, of the results selected from the group consisting of (A) increasing ON time without troublesome dyskinesia; and (B) reducing OFF time; and (C) improving CGI; in a subject with a CNS disorder, comprising administering to said subject once nightly, 0 to 4 hours before bedtime a composition comprising 260 to 420 mg amantadine, or an equivalent amount of a pharmaceutically acceptable salt thereof, and at least one release modifying excipient. In some embodiments, the composition comprises 260 to 340 mg amantadine, or an equivalent amount of a pharmaceutically acceptable salt thereof. In some embodiments, the composition comprises 260 mg amantadine, or an equivalent amount of a pharmaceutically acceptable salt thereof. In some embodiments, the composition comprises 340 mg of a pharmaceutically acceptable salt of amantadine. In some embodiments, the change in ON time without dyskinesia, the OFF time and/or the CGI are determined in a placebo controlled, double blind clinical study using the PD Home diary. In some embodiments, the CGI is determined by a question completed by the investigator. Also provided is an oral pharmaceutical composition as described herein for use in at least one, or at least two, of the results selected from the group consisting of (A) increasing ON time without troublesome dyskinesia; (B) reducing OFF time; and (C) improving CGI; in a subject with a CNS disorder, comprising administering to said subject once nightly, 0 to 4 hours before bedtime.

Some embodiments described herein provide a method resulting in at least one, preferably at least two, of the results selected from the group consisting of (A) increasing ON time without troublesome dyskinesia; and (B) reducing OFF time; and (C) improving CGI; in a subject with a CNS disorder, comprising administering to said subject once daily, a composition comprising 260 to 420 mg amantadine, or an equivalent amount of a pharmaceutically acceptable salt thereof, and at least one release modifying excipient. Also provided herein is an oral pharmaceutical composition for use in such methods. In some embodiments, the composition comprises 260 to 340 mg amantadine, or an equivalent amount of a pharmaceutically acceptable salt thereof. In some embodiments, the composition comprises 260 mg amantadine, or an equivalent amount of a pharmaceutically acceptable salt thereof. In some embodiments, the composition comprises 340 mg of a pharmaceutically acceptable salt of amantadine. In some embodiments, the change in ON time without dyskinesia, the OFF time and/or the CGI are determined in a placebo controlled, double blind clinical study using the PD Home diary. In some embodiments, the CGI is determined by a question completed by the investigator. In some such methods, the C-ave-day is 1.2 to 1.7 times the C-ave-night; in some embodiments of the method, the C-ave-day is determined between the hours of 8 am to 8 pm and the C-ave-night is determined between the hours of 8 pm to 8 am. In certain embodiments of the method, C-ave-day is determined between the hours of 5 am to 4 pm and C-ave-night is determined between the hours of 8 pm to 5 am. In some such methods, administration of a single dose of the composition to a cohort of human healthy volunteer subjects in a fasted state provides an average maximum plasma concentration (Cmax) of 1.1 to 2.0 ng/ml per mg of amantadine, or a pharmaceutically acceptable salt thereof, or an $AUC_{0-inf}$ (Area under the concentration-curve curve from t=0 to t=infinity) of 44 to 72 ng*h/mL per mg of amantadine, or a pharmaceutically acceptable salt thereof, or both. In some such methods, the daily oral administration of a dose of the composition to a cohort of human subjects provides a steady state plasma concentration profile characterized by at least one of: (i) a mean Cmax of 2.4 to 3.1 ng/ml per mg of amantadine, or a pharmaceutically acceptable salt thereof, (ii) a mean Cmin of 1.4 to 2.1 ng/ml per mg of amantadine, or a pharmaceutically acceptable salt thereof, and (iii) a mean $AUC_{0-24}$ of 44 to 72 ng*h/mL per mg of amantadine, or a pharmaceutically acceptable salt thereof, in more specific methods, all three criteria of (i), (ii) and (iii) are met.

The PD home diary is described in *Hauser*, et al., "A Home Diary to Assess Functional Status in Patients with Parkinson's Disease with Motor Fluctuations and Dyskinesia", Clin. Neuropharmacol., 23(3), pp. 75-81 (2000), which is incorporated herein by reference in its entirety. As used herein, the terms "ON time" and "OFF time," have the meanings described by Hauser et al. Id. Briefly, ON time is the period during which Parkinson's medication is providing benefit with regard to mobility, slowness, and stiffness; and OFF time is the period during which Parkinson's medication has worn off and is no longer providing benefit with regard to mobility, slowness, and stiffness. Id. These measures of time are separate from the scales used to measure reduction in LID, which primarily assess the change in dyskinesia severity or intensity. As such, these scales capture the benefit throughout the day and night of a given treatment for all four motor states. In some embodiments, a product profile includes benefits across this measure.

Dyskinesia is involuntary twisting, turning movements. Id. These movements are an effect of medication (i.e., levodopa) and occur during ON time. Id. Dyskinesia is distinct from tremor, which is shaking back and forth, a symptom of the underlying Parkinson's disease. Troublesome dyskinesia is dyskinesia that causes at least some difficulty with function. Id.

DETAILED DESCRIPTION OF THE INVENTION

Figure 1:
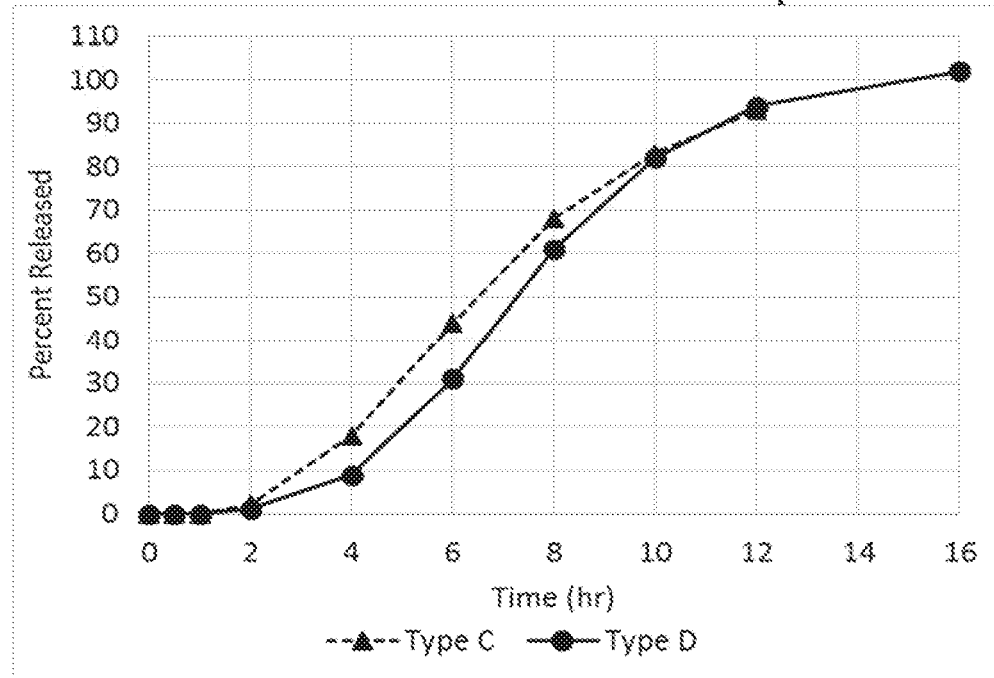
FIG. 1 shows the dissolution profiles for two formulations described in Examples 1 and 2.

Pharmaceutical compositions formulated for oral administration may include, for example, tablets, capsules, or a plurality of pellets within a capsule. These formulations may include one or more coatings, such as a drug coating in the case of compositions with pellets. In the preparation of pharmaceutical compositions, it is common to dissolve or disperse one or more ingredients (such as the active drug) in a solvent (such as an organic solvent) to make a mixture; use the mixture in one or more steps of the process; and then remove at least a portion of the solvent to produce the intended product. In the preparation of solid formulations, for example, pellets within a capsule, all or nearly all of the solvent is removed, such as by the application of heat and/or flowing of a gas. Thus, some pharmaceutical formulations have a very low, if any, residual solvent content.

As described herein, administration of compositions amantadine or a pharmaceutically acceptable salt thereof, for example in the treatment of symptoms of Parkinson's disease, can cause gastrointestinal side effects such as dry mouth, loss of appetite, nausea, vomiting, or diarrhea. The inventors have surprisingly found that in preparing certain formulations of oral compositions comprising amantadine, or a pharmaceutically acceptable salt thereof, the use of an organic solvent in certain steps results in residual organic solvent content in the final pharmaceutical composition, and that additional efforts to remove said organic solvent (such as increased drying time) did not lead to consistently lowered organic solvent content. However, by replacing the organic solvent in certain steps with water (though not necessarily all steps), compositions with lower residual organic solvent content could be obtained. Thus, in some embodiments, organic solvent is still used in one or more steps, but the resulting final formulation has a low residual organic solvent content. In some embodiments, the amount of organic solvent is reduced in one or more steps, for example, by replacing a portion of the organic solvent with water, and the resulting final formulation has a low residual organic solvent content. The inventors further surprisingly found that a higher incidence of gastrointestinal side effects was associated with administration of the compositions with higher residual organic solvent content. Thus, provided herein are oral pharmaceutical compositions comprising amantadine, or a pharmaceutically acceptable salt thereof, and a pharmaceutically acceptable excipient, with low organic solvent content. Also provided herein are methods of administering oral pharmaceutical compositions comprising amantadine or a pharmaceutically acceptable salt thereof.

I. Methods of Administration

The disclosure provides a method of orally administering once daily a composition comprising a therapeutically effective dose of amantadine, or a pharmaceutically acceptable salt thereof with a reduced incidence of gastrointestinal adverse events as compared to known amantadine formulations. Some embodiments described herein provide a method of increasing the ON time without dyskinesia in a subject with Parkinson's disease, comprising orally administering to the subject once per day, 0 to 4 hours before bedtime, a composition comprising 260 to 420 mg amantadine, or an equivalent amount of a pharmaceutically acceptable salt thereof (e.g., amantadine hydrochloride) and at least one release modifying excipient. In certain embodiments, provided is a method of increasing the ON time without dyskinesia in a subject with Parkinson's disease, comprising orally administering to the subject once per day, 0 to 4 hours before bedtime, a composition comprising about 68.5 mg, about 137 mg, about 205.5 mg, about 274 mg, from about 60 mg to about 80 mg, from about 120 mg to about 155 mg, from about 185 mg to about 230 mg, or from about 245 mg to about 305 mg of amantadine, or an equivalent amount of a pharmaceutically acceptable salt thereof (e.g., amantadine hydrochloride), and at least one release modifying excipient. In some embodiments, the oral composition is administered at night. In some such methods, the change in ON time without dyskinesia is determined in a placebo controlled, double blind clinical study using the PD Home Diary. In some such methods, the amantadine is provided as amantadine hydrochloride and the dose is from 300 to 360 mg per day, particularly 330 to 350 mg per day, and in particular 340 mg per day. In some embodiments, the once daily dose also provides a treatment that reduces or results in no increase in sleep related adverse events as compared to placebo (as determined from a randomized, double blind, placebo controlled study in subjects with Parkinson's).

Some embodiments described herein provide a method of reducing the ON time with dyskinesia in a subject with Parkinson's disease comprising orally administering to said subject once per day, 0 to 4 hours before bedtime a composition comprising 260 to 420 mg amantadine, or an equivalent amount of a pharmaceutically acceptable salt thereof (e.g., amantadine hydrochloride), and at least one release modifying excipient. In certain embodiments described herein, provided is a method of reducing the ON time with dyskinesia in a subject with Parkinson's disease comprising orally administering to said subject once per day, 0 to 4 hours before bedtime a composition comprising about 68.5 mg, about 137 mg, about 205.5 mg, about 274 mg, from about 60 mg to about 80 mg, from about 120 mg to about 155 mg, from about 185 mg to about 230 mg, or from about 245 mg to about 305 mg of amantadine, or an equivalent amount of a pharmaceutically acceptable salt thereof (e.g., amantadine hydrochloride), and at least one release modifying excipient. In some embodiments, the oral composition is administered once nightly. In some such methods, the change in ON time with dyskinesia is determined in a placebo controlled double blind clinical study using the PD Home Diary. In some such methods, the dose of a pharmaceutically acceptable salt of amantadine, is from 300 to 360 mg per day, particularly 330 to 350 mg per day, and in particular 340 mg per day.

Some embodiments described herein provide a method of reducing the ON time with troublesome dyskinesia in a subject with Parkinson's disease, comprising orally administering to said subject once per day, 0 to 4 hours before bedtime, a composition comprising 260 to 420 mg amantadine, or an equivalent amount of a pharmaceutically acceptable salt thereof (e.g., amantadine hydrochloride), and at least one release modifying excipient. In certain embodiments described herein, provided is a method of reducing the ON time with troublesome dyskinesia in a subject with Parkinson's disease, comprising orally administering to said subject once per day, 0 to 4 hours before bedtime, a composition comprising about 68.5 mg, about 137 mg, about 205.5 mg, about 274 mg, from about 60 mg to about 80 mg, from about 120 mg to about 155 mg, from about 185 mg to about 230 mg, or from about 245 mg to about 305 mg of amantadine, or an equivalent amount of a pharmaceutically acceptable salt thereof (e.g., amantadine hydrochloride), and at least one release modifying excipient. In some such methods, the change in ON time without troublesome dyskinesia is determined in a placebo controlled, double blind clinical study using the PD Home Diary. In some embodiments, the composition comprises 260 to 340 mg amantadine hydrochloride. In some such methods, the dose comprises amantadine hydrochloride from 300 to 360 mg per day, particularly 330 to 350 mg per day, and in particular 340 mg per day. In some embodiments, the oral composition is administered at night.

Some embodiments described herein provide a method of reducing the OFF time in a subject with Parkinson's disease comprising orally administering to said subject once per day, 0 to 4 hours before bedtime, a composition comprising 260 to 340 mg amantadine hydrochloride and at least one release modifying excipient. In certain embodiments described herein, provided is a method of reducing the OFF time in a subject with Parkinson's disease comprising orally administering to said subject once per day, 0 to 4 hours before bedtime, a composition comprising about 68.5 mg, about 137 mg, about 205.5 mg, about 274 mg, from about 60 mg to about 80 mg, from about 120 mg to about 155 mg, from about 185 mg to about 230 mg, or from about 245 mg to about 305 mg of amantadine, or an equivalent amount of a pharmaceutically acceptable salt thereof (e.g., amantadine hydrochloride), and at least one release modifying excipient. In some such methods, the change in OFF time is determined in a placebo controlled, double blind clinical study using the PD Home Diary. In some such methods, the dose of amantadine hydrochloride is from 300 to 360 mg per day, particularly 330 to 350 mg per day, and in particular 340 mg per day. In some embodiments, the composition is administered at night.

In some embodiments, provided herein is a method of reducing OFF time in a subject with Parkinson's disease, wherein the subject is being treated with a Parkinson's medication, comprising administering to the subject an oral pharmaceutical composition as described herein. Also provided herein is an oral pharmaceutical composition for use in reducing OFF time in a subject with Parkinson's disease, wherein the subject is being treated with a Parkinson's medication. In some embodiments, the Parkinson's medication is levodopa. In some embodiments, the Parkinson's medication comprises levodopa. For example, in some embodiments, the Parkinson's medication comprises levodopa in combination with carboidopa. In certain embodiments, the Parkinson's medication comprises levodopa in combination with carbidopa and entacapone. In some embodiments, the oral pharmaceutical composition is administered to the subject once per day, 0 to 4 hours before bedtime. In some embodiments, the oral pharmaceutical composition is administered to the subject once per day, 0 to 3 hours before bedtime. In some embodiments of the method and oral pharmaceutical composition for use as provided herein, the oral pharmaceutical composition comprises 50 mg to 500 mg of amantadine or an equivalent amount of a pharmaceutically acceptable salt thereof, and at least one release modifying excipient. In some embodiments, the oral pharmaceutical composition comprises between 100 mg to 450 mg, or 120 to 150 mg, or 260 mg to 305 mg, or 137 mg, or 174 mg of amantadine, or an equivalent amount of a pharmaceutically acceptable salt thereof. In some embodiments, the oral pharmaceutical composition comprises between 245 mg to 305 mg amantadine. In some embodiments, the oral pharmaceutical composition comprises a pharmaceutically acceptable salt of amantadine in an amount equivalent to between 245 mg to 305 mg amantadine. In other embodiments, the oral pharmaceutical composition comprises between 120 mg to 150 mg amantadine. In some embodiments, the oral pharmaceutical composition comprises a pharmaceutically acceptable salt of amantadine in an amount equivalent to between 120 mg to 150 mg amantadine. In certain embodiments, the pharmaceutically acceptable salt is amantadine hydrochloride. In some embodiments, the extended release oral composition comprises about 68.5 mg, about 137 mg, about 205.5 mg, about 274 mg of amantadine, from about 60 mg to about 80 mg, from about 120 mg to about 155 mg, from about 185 mg to about 230 mg, or from about 245 mg to about 305 mg of amantadine, or an equivalent amount of a pharmaceutically acceptable salt thereof. In some embodiments, the extended release oral composition comprises about 85 mg, about 170 mg, about 255 mg, about 340 mg from about 75 mg to about 95 mg, from about 150 mg to about 190 mg, from about 230 mg to about 285 mg, or from about 305 to about 375 mg of amantadine hydrochloride.

In some embodiments, the total daily amount of OFF time is reduced by at least 10%, at least 20%, at least 30%, at least 40%, at least 50%, at least 60%, or at least 70%. In some embodiments, the total daily amount of OFF time is reduced by between 10% to 70%, between 10% to 60%, between 10% to 50%, between 10% to 40%, between 10% to 30%, between 10% to 20%, between 20% to 70%, between 20% to 60%, between 20% to 50%, between 20% to 40%, between 20% to 30%, between 30% to 70%, between 30% to 60%, between 30% to 50%, or between 30% to 40%. In some embodiments, the total daily amount of OFF time is reduced by at least 0.25 hours, 0.5 hours, by at least 0.75 hours, by at least 1.0 hours, by at least 1.25 hours, or by at least 1.5 hours.

In certain embodiments, the total daily amount of OFF time is reduced in an amount as described herein after at least 6 weeks of administering once daily to the subject the oral pharmaceutical composition, after at least 7 weeks of administering once daily to the subject the oral pharmaceutical composition, after at least 8 weeks of administering once daily to the subject the oral pharmaceutical composition, after at least 9 weeks of administering once daily to the subject the oral pharmaceutical composition, after at least 10 weeks of administering once daily to the subject the oral pharmaceutical composition, after at least 11 weeks of administering once daily to the subject the oral pharmaceutical composition, or after at least 12 weeks of administering once daily to the subject the oral pharmaceutical composition. In certain embodiments, wherein the subject is first administered a first composition comprising lower dose of amantadine or an equivalent amount of a pharmaceutically acceptable salt thereof during a lead-in, titration period, the total daily amount of OFF time is reduced in an amount as described herein after at least 6 weeks of administering once daily to the subject a second oral pharmaceutical composition, after at least 7 weeks of administering once daily to the subject a second oral pharmaceutical composition, after at least 8 weeks of administering once daily to the subject a second oral pharmaceutical composition, after at least 9 weeks of administering once daily to the subject a second oral pharmaceutical composition, after at least 10 weeks of administering once daily to the subject a second oral pharmaceutical composition, after at least 11 weeks of administering once daily to the subject a second oral pharmaceutical composition, or after at least 12 weeks of administering once daily to the subject a second oral pharmaceutical composition, wherein the second oral pharmaceutical composition has a higher dose of amantadine, or an equivalent amount of a pharmaceutically acceptable salt thereof. In some embodiments, OFF time is reduced relative to a placebo, as evaluated in a placebo-controlled clinical study. In other embodiments, OFF time is reduced relative to the OFF time of the subject before beginning administering of the oral pharmaceutical composition. In certain embodiments, OFF time is reduced relative to the OFF time of the subject before beginning administering of the first oral pharmaceutical composition, wherein the subject is administered a first oral pharmaceutical composition during a lead-in titration period (with a lower dose of amantadine or an equivalent amount of a pharmaceutically acceptable salt thereof) and then a second oral pharmaceutical composition (with a higher dose of amantadine or an equivalent amount of a pharmaceutically acceptable salt thereof).

In some embodiments, provided herein is a method of increasing ON time without troublesome dyskinesia in a subject with Parkinson's disease, wherein the subject is being treated with a Parkinson's medication, comprising administering to the subject an oral pharmaceutical composition as described herein. Also provided herein is an oral pharmaceutical composition for use in increasing ON time without troublesome dyskinesia in a subject with Parkinson's disease, wherein the subject is being treated with a Parkinson's medication. In some embodiments, the Parkinson's medication is levodopa. In some embodiments, the Parkinson's medication comprises levodopa. For example, in some embodiments, the Parkinson's medication comprises levodopa in combination with carboidopa. In certain embodiments, the Parkinson's medication comprises levodopa in combination with carbidopa and entacapone. In some embodiments, the oral pharmaceutical composition is administered to the subject once per day, 0 to 4 hours before bedtime. In some embodiments, the oral pharmaceutical composition is administered to the subject once per day, 0 to 3 hours before bedtime. In some embodiments of the method and oral pharmaceutical composition for use as provided herein, the oral pharmaceutical composition comprises 50 mg to 500 mg of amantadine or an equivalent amount of a pharmaceutically acceptable salt thereof, and at least one release modifying excipient. In some embodiments, the oral pharmaceutical composition comprises between 100 mg to 450 mg, or 120 to 150 mg, or 260 mg to 305 mg, or 137 mg, or 174 mg of amantadine, or an equivalent amount of a pharmaceutically acceptable salt thereof. In some embodiments, the oral pharmaceutical composition comprises between 245 mg to 305 mg amantadine. In some embodiments, the oral pharmaceutical composition comprises a pharmaceutically acceptable salt of amantadine in an amount equivalent to between 245 mg to 305 mg amantadine. In other embodiments, the oral pharmaceutical composition comprises between 120 mg to 150 mg amantadine. In some embodiments, the oral pharmaceutical composition comprises a pharmaceutically acceptable salt of amantadine in an amount equivalent to between 120 mg to 150 mg amantadine. In certain embodiments, the pharmaceutically acceptable salt is amantadine hydrochloride. In some embodiments, the extended release oral composition comprises about 68.5 mg, about 137 mg, about 205.5 mg, about 274 mg of amantadine, from about 60 mg to about 80 mg, from about 120 mg to about 155 mg, from about 185 mg to about 230 mg, or from about 245 mg to about 305 mg of amantadine, or an equivalent amount of a pharmaceutically acceptable salt thereof. In some embodiments, the extended release oral composition comprises about 85 mg, about 170 mg, about 255 mg, about 340 mg from about 75 mg to about 95 mg, from about 150 mg to about 190 mg, from about 230 mg to about 285 mg, or from about 305 to about 375 mg of amantadine hydrochloride.

In some embodiments, the total daily amount of ON time without troublesome dyskinesia is increased by at least 10%, at least 20%, at least 30%, at least 40%, at least 50%, at least 60%, or at least 70%. In some embodiments, the total daily amount of ON time without troublesome dyskinesia is increased by between 10% to 70%, between 10% to 60%, between 10% to 50%, between 10% to 40%, between 10% to 30%, between 10% to 20%, between 20% to 70%, between 20% to 60%, between 20% to 50%, between 20% to 40%, between 20% to 30%, between 30% to 70%, between 30% to 60%, between 30% to 50%, or between 30% to 40%. In some embodiments, the total daily amount of ON time without troublesome dyskinesia is increased by at least 0.25 hours, 0.5 hours, by at least 0.75 hours, by at least 1.0 hours, by at least 1.25 hours, or by at least 1.5 hours.

In certain embodiments, the total daily amount of ON time without troublesome dyskinesia is increased in an amount as described herein after at least 6 weeks of administering once daily to the subject the oral pharmaceutical composition, after at least 7 weeks of administering once daily to the subject the oral pharmaceutical composition, after at least 8 weeks of administering once daily to the subject the oral pharmaceutical composition, after at least 9 weeks of administering once daily to the subject the oral pharmaceutical composition, after at least 10 weeks of administering once daily to the subject the oral pharmaceutical composition, after at least 11 weeks of administering once daily to the subject the oral pharmaceutical composition, or after at least 12 weeks of administering once daily to the subject the oral pharmaceutical composition. In certain embodiments, wherein the subject is first administered a first composition comprising lower dose of amantadine or an equivalent amount of a pharmaceutically acceptable salt thereof during a lead-in, titration period, the total daily amount of ON time without troublesome dyskinesia is increased in an amount as described herein after at least 6 weeks of administering once daily to the subject a second oral pharmaceutical composition, after at least 7 weeks of administering once daily to the subject a second oral pharmaceutical composition, after at least 8 weeks of administering once daily to the subject a second oral pharmaceutical composition, after at least 9 weeks of administering once daily to the subject a second oral pharmaceutical composition, after at least 10 weeks of administering once daily to the subject a second oral pharmaceutical composition, after at least 11 weeks of administering once daily to the subject a second oral pharmaceutical composition, or after at least 12 weeks of administering once daily to the subject a second oral pharmaceutical composition, wherein the second oral pharmaceutical composition has a higher dose of amantadine, or an equivalent amount of a pharmaceutically acceptable salt thereof. In some embodiments, ON time without troublesome dyskinesia is increased relative to a placebo, as evaluated in a placebo-controlled clinical study. In other embodiments, ON time without troublesome dyskinesia is increased relative to the ON time without troublesome dyskinesia in the subject before beginning administering of the oral pharmaceutical composition. In certain embodiments, ON time without troublesome dyskinesia is increased relative to the ON time without troublesome dyskinesia of the subject before beginning administering of the first oral pharmaceutical composition, wherein the subject is administered a first oral pharmaceutical composition during a lead-in titration period (with a lower dose of amantadine or an equivalent amount of a pharmaceutically acceptable salt thereof) and then a second oral pharmaceutical composition (with a higher dose of amantadine or an equivalent amount of a pharmaceutically acceptable salt thereof).

In still further embodiments, provided herein is a method of treating a hypokinetic disorder in a subject with Multiple Sclerosis, comprising administering to the subject an oral pharmaceutical composition as described herein. Also provided herein is an oral pharmaceutical composition for use in treating a hypokinetic disorder in a subject with Multiple Sclerosis. In some embodiments, the oral pharmaceutical composition is administered to the subject once per day, 0 to 4 hours before bedtime. In some embodiments, the oral pharmaceutical composition is administered to the subject once per day, 0 to 3 hours before bedtime. In some embodiments of the method and oral pharmaceutical composition for use as provided herein, the oral pharmaceutical composition comprises 50 mg to 500 mg of amantadine or an equivalent amount of a pharmaceutically acceptable salt thereof, and at least one release modifying excipient. In some embodiments, the oral pharmaceutical composition comprises between 100 mg to 450 mg, or 120 to 150 mg, or 260 mg to 305 mg, or 137 mg, or 174 mg of amantadine, or an equivalent amount of a pharmaceutically acceptable salt thereof. In some embodiments, the oral pharmaceutical composition comprises between 245 mg to 305 mg amantadine. In some embodiments, the oral pharmaceutical composition comprises a pharmaceutically acceptable salt of amantadine in an amount equivalent to between 245 mg to 305 mg amantadine. In other embodiments, the oral pharmaceutical composition comprises between 120 mg to 150 mg amantadine. In some embodiments, the oral pharmaceutical composition comprises a pharmaceutically acceptable salt of amantadine in an amount equivalent to between 120 mg to 150 mg amantadine. In certain embodiments, the pharmaceutically acceptable salt is amantadine hydrochloride. In some embodiments, the extended release oral composition comprises about 68.5 mg, about 137 mg, about 205.5 mg, about 274 mg of amantadine, from about 60 mg to about 80 mg, from about 120 mg to about 155 mg, from about 185 mg to about 230 mg, or from about 245 mg to about 305 mg of amantadine, or an equivalent amount of a pharmaceutically acceptable salt thereof. In some embodiments, the extended release oral composition comprises about 85 mg, about 170 mg, about 255 mg, about 340 mg from about 75 mg to about 95 mg, from about 150 mg to about 190 mg, from about 230 mg to about 285 mg, or from about 305 to about 375 mg of amantadine hydrochloride.

In certain embodiments of the methods for, and oral pharmaceutical compositions for use in, treating a hypokinetic disorder in a subject with Multiple Sclerosis, walking speed is improved, walking ability is improved, overall mobility is improved, or the ability to get up is improved, after beginning administration of the oral pharmaceutical composition. In certain embodiments, a two or more, or three or more, or each of walking speed is improved, walking ability is improved, overall mobility is improved, or the ability to get up is improved, after beginning administration of the oral pharmaceutical composition. In some embodiments, administration of a composition as described herein to a subject with Multiple Sclerosis results in a 5%, 10%, 15%, 20%, 25%, 30%, 35%, 40%, 45%, 50%, 55%, or 60% improvement in one or more of walking speed, walking ability, overall mobility, or ability to get up. In certain embodiments, administration of a composition as described herein to a subject with Multiple Sclerosis results in between 10% to 60%, between 10% to 50%, between 10% to 40%, between 10% to 30%, between 10% to 20%, between 20% to 60%, between 20% to 50%, between 20% to 40%, between 20% to 30%, between 30% to 60%, between 30% to 50%, or between 30% to 40% improvement in one or more of walking speed, walking ability, overall mobility, or ability to get up. Overall mobility may include, for example, the total amount of walking over the course of a day, or ability to get up at one or more times over the course of a day, or combinations thereof. In some embodiments, walking speed, walking ability, overall mobility, or ability to get up is evaluated via at least one of the following or a combination thereof: Timed 25-Foot Walking test (T25FW), Timed Up and Go (TUG), 2 minute walk test, six minute timed walk test (6MTW), and/or, Twelve Item Multiple Sclerosis Walking Scale (MSWS-12). In some embodiments, the T25FW, TUG, 2 minute walk, 6MTW and/or MSWS-12 is significantly improved relative to placebo, as evaluated in a placebo-controlled clinical trial. In other embodiments, the T25FW, TUG, 2 minute walk, 6MTW and/or MSWS-12 is significantly improved in the subject relative to before beginning administration of the composition as described herein. In some embodiments, the reduction walking impairment is measured on a numeric scale that is used by or accepted by the FDA or other regulatory agencies to evaluate the effectiveness of and to approve for licensure drugs for the treatment of walking impairment. In some embodiments, administration of the composition results in about 5%, 10%, 15%, 20%, 25%, 30%, 35%, 40%, 45%, 50%, 55%, or 60% improvement in one or more of the assessment scores described herein (such as the T25FW, TUG, 2 minute walk, 6MTW and/or MSWS-12).

In certain embodiments of the methods for, and oral pharmaceutical compositions for use in, treating a hypokinetic disorder in a subject with Multiple Sclerosis, walking speed is improved, walking ability is improved, overall mobility is improved, or the ability to get up is improved in an amount as described herein after at least 6 weeks of administering once daily to the subject the oral pharmaceutical composition, after at least 7 weeks of administering once daily to the subject the oral pharmaceutical composition, after at least 8 weeks of administering once daily to the subject the oral pharmaceutical composition, after at least 9 weeks of administering once daily to the subject the oral pharmaceutical composition, after at least 10 weeks of administering once daily to the subject the oral pharmaceutical composition, after at least 11 weeks of administering once daily to the subject the oral pharmaceutical composition, or after at least 12 weeks of administering once daily to the subject the oral pharmaceutical composition. In certain embodiments, wherein the subject is first administered a first composition comprising lower dose of amantadine or an equivalent amount of a pharmaceutically acceptable salt thereof during a lead-in, titration period, walking speed is improved, walking ability is improved, overall mobility is improved, or the ability to get up is improved in an amount as described herein after at least 6 weeks of administering once daily to the subject a second oral pharmaceutical composition, after at least 7 weeks of administering once daily to the subject a second oral pharmaceutical composition, after at least 8 weeks of administering once daily to the subject a second oral pharmaceutical composition, after at least 9 weeks of administering once daily to the subject a second oral pharmaceutical composition, after at least 10 weeks of administering once daily to the subject a second oral pharmaceutical composition, after at least 11 weeks of administering once daily to the subject a second oral pharmaceutical composition, or after at least 12 weeks of administering once daily to the subject a second oral pharmaceutical composition, wherein the second oral pharmaceutical composition has a higher dose of amantadine, or an equivalent amount of a pharmaceutically acceptable salt thereof. In some embodiments, walking speed is improved, walking ability is improved, overall mobility is improved, or the ability to get up is improved relative to a placebo, as evaluated in a placebo-controlled clinical study. In other embodiments, walking speed is improved, walking ability is improved, overall mobility is improved, or the ability to get up is improved relative to the same metric in the subject before beginning administering of the oral pharmaceutical composition. In certain embodiments, walking speed is improved, walking ability is improved, overall mobility is improved, or the ability to get up is improved relative to the same metric in the subject before beginning administering of the first oral pharmaceutical composition, wherein the subject is administered a first oral pharmaceutical composition during a lead-in titration period (with a lower dose of amantadine or an equivalent amount of a pharmaceutically acceptable salt thereof) and then a second oral pharmaceutical composition (with a higher dose of amantadine or an equivalent amount of a pharmaceutically acceptable salt thereof).

Some embodiments described herein provide a method of increasing the ON time without troublesome dyskinesia without increasing sleep disturbances in a subject with Parkinson's disease comprising orally administering to said subject once per day, 0 to 4 hours before bedtime a composition comprising 260 to 420 mg amantadine, or an equivalent amount of a pharmaceutically acceptable salt thereof (e.g., amantadine hydrochloride), and at least one release modifying excipient. In some embodiments, the composition comprises 260 to 340 mg amantadine hydrochloride. In some such methods, the dose of amantadine hydrochloride is from 300 to 360 mg per day, particularly 330 to 350 mg per day, and in particular 340 mg per day. In some embodiments, the composition is administered at night.

Some embodiments described herein provide a method of improving Clinician's Global Impression without increasing sleep disturbances in a subject with Parkinson's disease comprising orally administering to said subject once per day, 0 to 4 hours before bedtime a composition comprising 260 to 420 mg amantadine, or an equivalent amount of a pharmaceutically acceptable salt thereof (e.g., amantadine hydrochloride), and at least one release modifying excipient. In some embodiments, the composition comprises 260 to 340 mg amantadine hydrochloride. In some such methods, the dose of amantadine hydrochloride is from 300 to 360 mg per day, particularly 330 to 350 mg per day, and in particular 340 mg per day. In some embodiments, the composition is administered at night.

Some embodiments described herein provide a method of increasing the ON time without dyskinesia in a subject with Parkinson's disease, comprising orally administering to the subject once daily, a composition comprising 260 to 420 mg amantadine, or an equivalent amount of a pharmaceutically acceptable salt thereof (e.g., amantadine hydrochloride) and at least one release modifying excipient. In some embodiments, the composition comprises 260 to 340 mg amantadine hydrochloride. In some such methods, the change in ON time without dyskinesia is determined in a placebo controlled, double blind clinical study using the PD Home Diary. In some such methods, the dose of amantadine hydrochloride is from 300 to 360 mg per day, particularly 330 to 350 mg per day, and in particular 340 mg per day. In some embodiments, the composition is administered at night. In some such methods, the C-ave-day is 1.2 to 1.7 times the C-ave-night; in some embodiments of the methods, the C-ave-day is measured between the hours of 6 am to 4 pm and the C-ave-night is measured between the hours of 8 pm to 5 am. In some such methods, administration of a single dose of the composition to a cohort of human healthy volunteer subjects in a fasted state provides an average maximum plasma concentration (Cmax) of 1.1 to 2.0 ng/ml per mg of amantadine or an $AUC_{0-inf}$ (Area under the concentration-curve curve from t=0 to t=infinity) of 42 to 56 ng*h/mL per mg of amantadine or both. In some such methods, the daily oral administration of a dose of the composition to a cohort of human subjects provides a steady state plasma concentration profile characterized by at least one of: (i) a mean Cmax of 2.2 to 3.1 ng/ml per mg of amantadine, (ii) a mean Cmin of 1.4 to 1.7 ng/ml per mg of amantadine, and (iii) a mean $AUC_{0-24}$ of 43 to 72 ng*h/mL per mg of amantadine; in more specific methods, all three criteria of (i), (ii) and (iii) are met.

Some embodiments described herein provide a method of reducing the ON time with dyskinesia in a subject with Parkinson's disease comprising orally administering to said subject once daily, a composition comprising 260 to 420 mg amantadine, or an equivalent amount of a pharmaceutically acceptable salt thereof (e.g., amantadine hydrochloride), and at least one release modifying excipient. In some embodiments, the composition comprises 260 to 340 mg amantadine hydrochloride. In some such methods, the change in ON time with dyskinesia is determined in a placebo controlled, double blind clinical study using the PD Home Diary. In some such methods, the dose of amantadine, or pharmaceutically acceptable salt thereof, is from 300 to 360 mg per day, particularly 330 to 350 mg per day, and in particular 340 mg per day. In some embodiments, the composition is orally administered at night. In some such methods, the C-ave-day is 1.2 to 1.7 times the C-ave-night; in some embodiments of the methods the C-ave-day is measured between the hours of 8 am to 4 pm and the C-ave-night is measured between the hours of 8 pm to 5 am. In some such methods, administration of a single dose of the composition to a cohort of human healthy volunteer subjects in a fasted state provides an average maximum plasma concentration (Cmax) of 1.1 to 2.0 ng/ml per mg of amantadine or an $AUC_{0-inf}$ (Area under the concentration-curve curve from t=0 to t=infinity) of 42 to 70 ng*h/mL per mg of amantadine or both. In some such methods, the daily oral administration of a dose of the composition to a cohort of human subjects provides a steady state plasma concentration profile characterized by at least one of: (i) a mean Cmax of 2.2 to 3.1 ng/ml per mg of amantadine, (ii) a mean Cmin of 1.4 to 1.7 ng/ml per mg of amantadine, and (iii) a mean $AUC_{0-24}$ of 43 to 70 ng*h/mL per mg of amantadine; in more specific methods, all three criteria of (i), (ii) and (iii) are met.

Some embodiments described herein provide a method of reducing the ON time with troublesome dyskinesia in a subject with Parkinson's disease, comprising orally administering to said subject once daily, a composition comprising 260 to 420 mg amantadine, or an equivalent amount of a pharmaceutically acceptable salt thereof (e.g., amantadine hydrochloride), and at least one release modifying excipient. In some embodiments, the composition comprises 260 to 340 mg amantadine hydrochloride. In some embodiments, the composition is orally administered at night. In some such methods, the change in ON time without troublesome dyskinesia is determined in a placebo controlled, double blind clinical study using the PD Home Diary. In some such methods, the dose of a pharmaceutically acceptable salt of amantadine is from 300 to 360 mg per day, particularly 330 to 350 mg per day, and in particular 340 mg per day. In some such methods, the C-ave-day is 1.2 to 1.7 times the C-ave-night; in some embodiments of the methods, the C-ave-day is measured between the hours of 8 am to 4 pm and the C-ave-night is measured between the hours of 8 pm to 5 am. In some such methods, administration of a single dose of the composition to a cohort of human healthy volunteer subjects in a fasted state provides an average maximum plasma concentration (Cmax) of 1.1 to 2.0 ng/ml per mg of amantadine or an $AUC_{0-inf}$ (Area under the concentration-curve curve from t=0 to t=infinity) of 42 to 70 ng*h/mL per mg of amantadine or both. In some such methods, the daily oral administration of a dose of the composition to a cohort of human subjects provides a steady state plasma concentration profile characterized by at least one of: (i) a mean Cmax of 2.2 to 3.0 ng/ml per mg of amantadine, (ii) a mean Cmin of 1.4 to 1.7 ng/ml per mg of amantadine, and (iii) a mean $AUC_{0-24}$ of 42 to 69 ng*h/mL per mg of amantadine; in more specific methods, all three criteria of (i), (ii) and (iii) are met.

Some embodiments described herein provide a method of reducing the OFF time in a subject with Parkinson's disease comprising orally administering to said subject once daily, a composition comprising 260 to 340 mg amantadine, or an equivalent amount of a pharmaceutically acceptable salt thereof (e.g., amantadine hydrochloride), and at least one release modifying excipient. In some embodiments, the composition comprises 260 to 340 mg amantadine hydrochloride. In some such methods, the change in OFF time is determined in a placebo controlled, double blind clinical study using the PD Home Diary. In some such methods, the dose of a pharmaceutically acceptable salt of amantadine, is from 300 to 360 mg per day, particularly 330 to 350 mg per day, and in particular 340 mg per day. In some such methods, the C-ave-day is 1.4 to 1.7 times the C-ave-night; in some embodiments of the methods, the C-ave-day is measured between the hours of 8 am to 8 pm and the C-ave-night is measured between the hours of 8 pm to 8 am. In some such methods, administration of a single dose of the composition to a cohort of human healthy volunteer subjects in a fasted state provides an average maximum plasma concentration (Cmax) of 1.1 to 1.7 ng/ml per mg of amantadine or an $AUC_{0-inf}$ (Area under the concentration-curve curve from t=0 to t=infinity) of 46 to 56 ng*h/mL per mg of amantadine or both. In some such methods, the daily oral administration of a dose of the composition to a cohort of human subjects provides a steady state plasma concentration profile characterized by at least one of: (i) a mean Cmax of 2.2 to 2.7 ng/ml per mg of amantadine, (ii) a mean Cmin of 1.4 to 1.7 ng/ml per mg of amantadine, and (iii) a mean $AUC_{0-24}$ of 46 to 56 ng*h/mL per mg of amantadine; in more specific methods, all three criteria of (i), (ii) and (iii) are met.

Some embodiments described herein provide a method of increasing the ON time without troublesome dyskinesia without increasing sleep disturbances in a subject with Parkinson's disease comprising orally administering to said subject once daily, a composition comprising 260 to 420 mg amantadine, or an equivalent amount of a pharmaceutically acceptable salt thereof (e.g., amantadine hydrochloride), and at least one release modifying excipient. In some embodiments, the composition comprises 260 to 340 mg amantadine hydrochloride. In some such methods, the dose of a pharmaceutically acceptable salt of amantadine, such as amantadine hydrochloride, is from 300 to 360 mg per day, particularly 330 to 350 mg per day, and in particular 340 mg per day. In some such methods, the C-ave-day is 1.2 to 1.7 times the C-ave-night; in some embodiments of the methods, the C-ave-day is measured between the hours of 8 am to 4 pm and the C-ave-night is measured between the hours of 8 pm to 5 am. In some such methods, administration of a single dose of the composition to a cohort of human healthy volunteer subjects in a fasted state provides an average maximum plasma concentration (Cmax) of 1.1 to 2.0 ng/ml per mg of amantadine or an $AUC_{0-inf}$ (Area under the concentration-curve curve from t=0 to t=infinity) of 42 to 69 ng*h/mL per mg of amantadine or both. In some such methods, the daily oral administration of a dose of the composition to a cohort of human subjects provides a steady state plasma concentration profile characterized by at least one of: (i) a mean Cmax of 2.2 to 3.1 ng/ml per mg of amantadine, (ii) a mean Cmin of 1.4 to 1.7 ng/ml per mg of amantadine, and (iii) a mean $AUC_{0-24}$ of 42 to 69 ng*h/mL per mg of amantadine; in more specific methods, all three criteria of (i), (ii) and (iii) are met.

Some embodiments described herein provide a method of improving Clinician's Global Impression without increasing sleep disturbances in a subject with Parkinson's disease comprising orally administering to said subject once daily, a composition comprising 260 to 420 mg amantadine, or an equivalent amount of a pharmaceutically acceptable salt thereof (e.g., amantadine hydrochloride), and at least one release modifying excipient. In some embodiments, the composition comprises 260 to 340 mg amantadine hydrochloride, or an equivalent amount of a pharmaceutically acceptable salt thereof. In some such methods, the dose of a pharmaceutically acceptable salt of amantadine, such as amantadine hydrochloride, is from 300 to 360 mg per day, particularly 330 to 350 mg per day, and in particular 340 mg per day. In some such methods, the C-ave-day is 1.2 to 1.7 times the C-ave-night; in some embodiments of the methods, the C-ave-day is measured between the hours of 8 am to 4 pm and the C-ave-night is measured between the hours of 8 pm to 5 am. In some such methods, administration of a single dose of the composition to a cohort of human healthy volunteer subjects in a fasted state provides an average maximum plasma concentration (Cmax) of 1.1 to 2.0 ng/ml per mg of amantadine or an $AUC_{0-inf}$ (Area under the concentration-curve curve from t=0 to t=infinity) of 42 to 69 ng*h/mL per mg of amantadine or both. In some such methods, the daily oral administration of a dose of the composition to a cohort of human subjects provides a steady state plasma concentration profile characterized by at least one of: (i) a mean Cmax of 2.2 to 3.1 ng/ml per mg of amantadine, (ii) a mean Cmin of 1.4 to 1.7 ng/ml per mg of amantadine, and (iii) a mean $AUC_{0-24}$ of 42 to 69 ng*h/mL per mg of amantadine; in more specific methods, all three criteria of (i), (ii) and (iii) are met.

The disclosure also provides a method of reducing gastrointestinal (GI) adverse events in a subject undergoing treatment with amantadine. The method comprises orally administering a composition comprising amantadine, or a pharmaceutically acceptable salt thereof, to a subject in need thereof, such that the frequency of GI adverse events (as determined from single dose, fasting human pharmacokinetic studies) is less than 19.5%; preferably less than 17.5%, and more preferably less than 12.5%. In some embodiments, a low incidence of gastrointestinal adverse events includes less than 12%, less than 10%, less than 8%, less than 7%, less than 6%, less than 5%, less than 4%, less than 3%, less than 2%, or less than 1% of the subjects of a fasted, single dose human pharmacokinetic study experiencing at least one gastrointestinal adverse event. In some embodiments, the gastrointestinal effects are selected from the group consisting of abdominal distension, constipation, diarrhea, dyspepsia, gingival pain, dry lip, lower abdominal pain, nausea, stomach discomfort, toothache, upper abdominal pain, and vomiting In some embodiments, the composition comprises less than 6000 ppm of organic solvent. In certain embodiment, the composition comprises less than 5500 ppm, less than 5000 ppm, less than 4500 ppm, less than 4000 ppm, less than 3500 ppm, less than 3000 ppm, less than 2500 ppm, less than 2000 ppm, less than 1500 ppm, or less than 1200 ppm organic solvent. In some embodiments, the composition comprises a plurality of coated core seeds, wherein each coated core seed comprises a core seed surrounded by a drug coating, and the plurality of coated core seeds comprises less than 6000 ppm, less than 5500 ppm, less than 5000 ppm, less than 4500 ppm, less than 4000 ppm, less than 3500 ppm, less than 3000 ppm, less than 2500 ppm, less than 2000 ppm, less than 1500 ppm, or less than 1200 ppm organic solvent. In some embodiments, the organic solvent is a linear or cyclic ketone (e.g., acetone, methyl ethyl ketone, etc.) In some embodiments, the organic solvent is a sulfoxide (e.g., dimethyl sulfoxide, etc). In some embodiments, the organic solvent is an amide (e.g., dimethyl formamide, N-methyl pyrrolidone, hexamethyl phosphorous triamide (HMPT), etc.). In some embodiments, the organic solvent is a linear or cyclic ether (e.g., tetrahydrofuran, diethyl ether, bis(2-methoxyethyl) ether (diglyme), dimethoxy ethane (glyme), 1,4-dioxane, etc.). In some embodiments, the organic solvent is a phosphoramide (e.g., hexamethyl phosphoramide (HPMA), etc.). In some embodiments, the organic solvent is a chlorinated hydrocarbon (e.g., chloroform, dichloromethane, dichloro ethane, carbon tetrachloride, etc.). In some embodiments, the organic solvent is a glycol (e.g., ethylene glycol, diethylene glycol, propylene glycol, etc.). In some embodiments, the organic solvent is a, nitrogen-containing solvent (e.g., pyridine, acetonitrile, etc.). In some embodiments, the organic solvent is an alcohol (e.g., a $C_1$-$C_6$ alcohol (e.g., ethanol, methanol, isopropanol, 1-butanol, 2-butanol, glycerol), such as isopropyl alcohol. In some embodiments, mixtures of two or more solvents can be used. In some embodiments of the levels of organic solvent described herein, the provided level refers to the total amount of two or more organic solvents. In some embodiments, the daily dose of amantadine is 170 mg to 340 mg, or an equivalent amount of a pharmaceutically acceptable salt thereof; preferably the daily dose comprises 170 mg to 340 mg of amantadine hydrochloride, or an equivalent amount of a pharmaceutically acceptable salt thereof. In some such methods, the C-ave-day is 1.2 to 1.7 times the C-ave-night; in some embodiments of the methods, the C-ave-day is measured between the hours of 8 am to 4 pm and the C-ave-night is measured between the hours of 8 pm to 5 am. In some such methods, administration of a single dose of the composition to a cohort of human healthy volunteer subjects in a fasted state provides an average maximum plasma concentration (Cmax) of 1.1 to 2.0 ng/ml per mg of amantadine or an $AUC_{0-inf}$ (Area under the concentration-curve curve from t=0 to t=infinity) of 42 to 69 ng*h/mL per mg of amantadine or both. In some such methods, the daily oral administration of a dose of the composition to a cohort of human subjects provides a steady state plasma concentration profile characterized by at least one of: (i) a mean Cmax of 2.2 to 3.0 ng/ml per mg of amantadine, (ii) a mean Cmin of 1.4 to 1.7 ng/ml per mg of amantadine, and (iii) a mean $AUC_{0-24}$ of 42 to 69 ng*h/mL per mg of amantadine; in more specific methods, all three criteria of (i), (ii) and (iii) are met.

The disclosure also provides a method of reducing sleep disturbances in a subject undergoing treatment with amantadine, or a pharmaceutically acceptable salt thereof. The method comprises orally administering amantadine, or a pharmaceutically acceptable salt thereof, to a subject in need thereof, such that the amantadine or pharmaceutically acceptable salt thereof does not interfere with sleep, yet provides maximum benefit in morning hours. Morning hours may include, for example, from the hour of 5 am, 6 am, 7 am, 8 am or 9 am to the hour of 11 am, 11:30 am, 12 pm, 12:30 pm or 1:00 pm. In some embodiments, the method provides nighttime coverage of symptoms of Parkinson's. Nighttime coverage may include providing benefit if the subject wakes up and wishes to return to sleep. In some such methods, the C-ave-day is 1.2 to 1.7 times the C-ave-night; in some embodiments of the methods, the C-ave-day is measured between the hours of 8 am to 4 pm and the C-ave-night is measured between the hours of 8 pm to 5 am. In some such methods, administration of a single dose of the composition to a cohort of human healthy volunteer subjects in a fasted state provides an average maximum plasma concentration (Cmax) of 1.1 to 2.0 ng/ml per mg of amantadine or an $AUC_{0-inf}$ (Area under the concentration-curve curve from t=0 to t=infinity) of 42 to 69 ng*h/mL per mg of amantadine or both. In some such methods, the daily oral administration of a dose of the composition to a cohort of human subjects provides a steady state plasma concentration profile characterized by at least one of: (i) a mean Cmax of 2.2 to 3.0 ng/ml per mg of amantadine, (ii) a mean Cmin of 1.4 to 1.7 ng/ml per mg of amantadine, and (iii) a mean $AUC_{0-24}$ of 42 to 69 ng*h/mL per mg of amantadine; in more specific methods, all three criteria of (i), (ii) and (iii) are met.

In some embodiments, the methods provided herein comprise orally administering to a subject an extended release (ER) composition comprising amantadine, or a pharmaceutically acceptable salt thereof, formulated for nighttime administration. The composition may be a less than three hours before bedtime, and preferably less than two and a half, less than two, less than one and a half, or less than one hour before bedtime. Most preferably the ER composition is taken less than half hour before bedtime (e.g., the time at which the subject wishes to go to sleep). Alternatively, the composition is administered less than about 4 hours before bedtime.

As used herein, "extended release" includes "controlled release", "modified release", "sustained release", "timed release", "delayed release", and also mixtures of delayed release, immediate release, enteric coated, etc. with each of the above.

The methods included herein include orally administering to a subject a pharmaceutical composition comprising amantadine or a pharmaceutically acceptable salt thereof. The subject may be diagnosed with any disease or disorder for which amantadine or a pharmaceutically acceptable salt thereof is prescribed, such as Parkinson's disease, multiple sclerosis, drug-induced extrapyramidal reactions, levodopa-induced dyskinesia, or a viral disease (e.g., influenza, HBV, or HCV). In a specific embodiment, the subject has Parkinson's disease, which, as used herein, also encompasses a diagnosis of parkinsonism. In some embodiments, the subject has early stage Parkinson's disease, and the pharmaceutical composition as described herein is used as a monotherapy or in combination with a monoamine oxidase type B (MAO-B) inhibitor without concomitant use of levodopa. In another embodiment, the subject has late stage Parkinson's disease and the subject takes levodopa in addition to a pharmaceutical composition as described herein. In another embodiment, the subject has multiple sclerosis and the pharmaceutical composition as described herein is used for the treatment of fatigue. In other embodiments, the subject has a brain injury, brain injury, brain trauma, dementia, Alzheimer's disease, stroke, Huntington's disease, ALS, Multiple Sclerosis, neurodegenerative diseases, dementias, cerebrovascular conditions, movement disorders, cranial nerve disorders, or a neuropsychiatric disorder.

The oral pharmaceutical compositions provided herein, and for use in the methods described herein, may be formulated for oral nighttime administration to provide a plasma concentration profile that does not interfere with the subject's sleep. The composition of the disclosure may, upon administration to a human subject, result in a gradual initial increase in plasma concentration of amantadine such that, at steady state conditions, administration of a dose of the composition results in an increase in plasma concentration of amantadine of less than 25% at three hours after the dose is administered. For example, if a subject's steady state plasma concentration of amantadine is 500 ng/ml at the time a dose of the composition is administered, three hours later the subject's plasma concentration of amantadine may be less than 625 ng/ml. Preferably, the increase in plasma concentration of amantadine three hours after administration of an oral pharmaceutical composition as described herein is less than 15%, and most preferably, less than 10%. In certain embodiments, the compositions have a plasma concentration profile further characterized by no increase in amantadine plasma concentration, or even a decrease (at steady state conditions), for at least one or, in some embodiments, two hours after the administration. The compositions provided herein, and for use in the methods provided herein, may be adapted for bedtime (e.g., the time at which the subject wishes to go to sleep) administration by providing a maximum concentration of amantadine (Cmax) in the morning hours. The time to reach Cmax (Tmax), as measured after single dose administration in the fasted state, may be at least 9 hours and up to 15, 16, 17, or 18 hours, or at least 10 hours and up to 14, 15, 16, 17, or 18 hours, or at least 12 hours, and up to 14, 15, 16, or 17 hours. In specific embodiments, the Tmax may be 9 to 18 hours, most preferably 12 to 18 hours. At steady state, with once nightly administration of the composition, the Tmax may be 7 to 13 hours, most preferably 8 to 12 hours. A suitable ER amantadine composition may have a steady-state Cmax/Cmin ratio of 1.3 to 1.8, and preferably 1.4 to 1.7, resulting in a composition with daily profile.

In other embodiments, the plasma concentration profile has an AUC profile after administration of a single dose of the composition wherein: the fractional AUC from 0 to 4 hours is less than 5%, and preferably less than 3% of $AUC_{0-inf}$; the fractional AUC from 0 to 8 hours is about 5 to 15%, and preferably about 8 to 12% of $AUC_{0-inf}$; the fractional AUC from 0 to 12 hours is about 10 to 40%, and preferably about 15 to 30% of $AUC_{0-inf}$; the fractional AUC from 0 to 18 hours is about 25 to 60%, and preferably about 30 to 50% of $AUC_{0-inf}$; and the fractional AUC from 0 to 24 hours is about 40 to 75%, and preferably about 50 to 70% of $AUC_{0-inf}$.

In further embodiments, the plasma concentration profile of the pharmaceutical composition has an AUC profile after once nightly dosing of the composition at steady state conditions wherein: the fractional AUC from 0 to 4 hours is about 2 to 25%, and preferably about 5 to 20% of $AUC_{0-24}$; the fractional AUC from 0 to 8 hours is about 15 to 50%, and preferably about 20 to 40% of $AUC_{0-24}$; the fractional AUC from 0 to 12 hours is about 30 to 70%, and preferably about 40 to 60% of $AUC_{0-24}$; and the fractional AUC from 0 to 18 hours is about 60 to 95%, and preferably about 75 to 90% of $AUC_{0-24}$.

In some embodiments of any of the aspects herein, the steady state plasma concentration profile following multiple oral administrations to a human subject of the composition at bedtime is characterized by an average plasma concentration during the day ("C-ave-day", defined as the average day time amantadine plasma concentration as measured in a human PK study) that is 1.1 to 2.0 times the average plasma concentration during the night ("C-ave-night", defined as the average night time amantadine plasma concentration as measured in a human PK study). In some embodiments, the ratio of C-ave-day/C-ave-night at steady state is within one of the ranges 1.3 to 1.9, 1.3 to 1.8, 1.3 to 1.7, 1.3 to 1.6, 1.4 to 1.9, 1.4 to 1.8, 1.4 to 1.7, 1.5 to 1.9, 1.5 to 1.8, 1.5 to 1.7, or 1.6 to 1.9. In some embodiments, the ratio of C-ave-day/C-ave-night at steady state is 1.3, 1.35, 1.4, 1.45, 1.5, 1.55, 1.6, 1.65, 1.7, 1.75, 1.8, 1.85, or 1.9. In some embodiments, the C-ave-day is the average amantadine plasma concentration as measured between the hours of 5 am, 6 am, 7 am, 8 am or 9 am to the hours of 4 pm, 5 pm, 6 pm, 7 pm or 8 pm and the C-ave-night is the average amantadine plasma concentration as measured between the hours of 4 pm, 5 pm, 6 pm, 7 pm, 8 pm, 9 pm, 10 pm or 11 pm to the hours of 4 am, 5 am, 6 am, 7 am, 8 am or 9 am. In some embodiments, the C-ave-day is the average amantadine plasma concentration as measured within any four to twelve hour period between the hours of 5 am and 8 pm; and the C-ave-night is the average amantadine plasma concentration as measured within any four to twelve hour period between the hours of 8 pm and 5 am. In some embodiments, the C-ave-day is the average amantadine plasma concentration as measured within any four, five, six, seven, eight, nine, ten, eleven or twelve hour period between the hours of 5 am and 8 pm; and the C-ave-night is the average amantadine plasma concentration as measured within any four, five, six, seven, eight, nine, ten, eleven or twelve hour period between the hours of 8 pm and 4 am.

In some embodiments described herein the pharmaceutical composition is administered to a subject from 0 to 4 hours prior to bedtime. In some embodiments, the pharmaceutical composition is administered to a subject from 0 to 3, 0 to 2, or 0 to 1 hours prior to bedtime. In some embodiments, the pharmaceutical composition is administered to a subject from 0 to 240 minutes, from 0 to 180 minutes, e.g., from 0 to 120 minutes, from 0 to 60 minutes, from 0 to 45 minutes, from 0 to 30 minutes, from 0 to 15 minutes or from 0 to 10 minutes prior to bedtime. In some embodiments, the pharmaceutical composition is administered to a subject from 60 to 240 minutes, from 60 to 180 minutes, from 60 to 120 minutes or from 60 to 90 minutes prior to bedtime.

It is to be understood that administration to a subject includes administration by a healthcare professional and self-administration by the subject.

Unless otherwise specified herein, the term "bedtime" described when a person retires for the primary sleep period during a twenty-four hour period of time. While for the general populace, bedtime occurs at night, there are subjects, such as those who work nights, for whom bedtime occurs during the day. Thus, in some embodiments, bedtime may be anytime during the day or night.

As used herein, unless otherwise indicated, reference to a plasma concentration profile or a specific pharmacokinetic property (e.g., Cmax, Cmin, AUC, Tmax, etc.) in a human subject refers to a mean value obtained from healthy adults determined in a typical phase I clinical trial designed to measure pharmacokinetic properties of a drug (see e.g., Example 4 below); and, unless indicated otherwise, a single dose, fasting human pharmacokinetic study is dosed in the morning following an overnight fast. References herein to Tmax and $T_{1/2}$ refer to median and mean values, respectively, obtained after administration of a single dose at fasted states, unless otherwise indicated.

As described herein, the unit doses of the amantadine or pharmaceutically acceptable salt thereof orally administered in accordance with the methods provided herein may be generally higher than the ranges normally prescribed for immediate release compositions comprising amantadine or a pharmaceutically acceptable salt thereof. For example, the recommended dose of amantadine for the treatment of Parkinson's disease is 100 mg immediate release amantadine administered twice daily, or an equivalent amount of a pharmaceutically acceptable salt thereof. In limited cases of the subject not deriving sufficient benefit at that dose, and subject to the subject being able to tolerate a higher dose, the daily dose may be increased to 300 mg or 400 mg, or an equivalent amount of a pharmaceutically acceptable salt thereof, which is always administered in divided doses. The most commonly prescribed dose of amantadine is 200 mg per day, or an equivalent amount of a pharmaceutically acceptable salt thereof, is always administered in divided doses. More than 200 mg (for example 300 mg) was always given in divided doses. In contrast, the present methods may include administration of 260 to 420 mg of amantadine, or an equivalent amount of a pharmaceutically acceptable salt, for treatment of a subject with Parkinson's disease, and the methods and compositions of the disclosure may comprise once-nightly administration of a dose as defined by any of these ranges, particularly at doses from 260 mg to 420 mg, and most preferably 340 mg of amantadine, or an equivalent amount of a pharmaceutically acceptable salt thereof, once per day. In some such embodiments the administration of such higher doses is at night, e.g., after 4 p.m. and/or within 4 hours of bedtime. In additional embodiments, the administration of such higher doses may be in the form of 1, 2 or 3 capsules of size 0, 1 or 2 in the normal or EL format administered once nightly.

In some embodiments of any of the aspects herein the amantadine is administered as a pharmaceutically acceptable salt. In a more specific embodiment, the amantadine is administered as amantadine hydrochloride or amantadine sulfate.

In some embodiments of any of the aspects herein, a total daily dose of 260 mg to 420 mg of amantadine or an equivalent amount of a pharmaceutically acceptable salt thereof is administered as a formulation after 4 p.m. and/or within 4 hours of bedtime. In some embodiments, the dose of amantadine or pharmaceutically acceptable salt thereof exceeds 300 mg per day. In various specific embodiments, the total dose of amantadine administered per day may be 260 to 275 mg, 270 to 285 mg, 280 to 295 mg, 290 to 305 mg, 300 to 315 mg, 310 to 325 mg, 320 to 335 mg, 330 to 345 mg, 340 to 355 mg, 350 to 365 mg, 360 to 375 mg, 370 to 385 mg, 380 to 395 mg, 390 to 405 mg, 400 to 415 mg, or 410 to 420 mg, or the dose may be an equivalent amount of a pharmaceutically acceptable salt thereof. In some embodiments, the total dose of amantadine administered per day is 260 mg to 360 mg, 300 to 360 mg, 330 to 350 mg or 340 mg, or an equivalent amount of a pharmaceutically acceptable salt thereof. In some embodiments, the dose of a pharmaceutically acceptable salt of amantadine, such as amantadine hydrochloride, is 300 to 360 mg, 330 to 350 mg or 340 mg. As described herein, the dose may be a single daily dose, and may be administered at night, for example after 4 pm.

In some embodiments of any of the aspects herein, the total once daily dose of amantadine administered is from about 260 mg, 265 mg, 270 mg, 275 mg, 280 mg, 285 mg, 290 mg, 295 mg, or 300 mg, or an equivalent amount of a pharmaceutically acceptable salt of amantadine; to about 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, or 420 mg, or an equivalent amount of a pharmaceutically acceptable salt of amantadine.

In still further embodiments of any of the aspects herein, such as methods of increasing the ON time without dyskinesia in a subject with Parkinson's disease; reducing the ON time with dyskinesia in a subject with Parkinson's disease; reducing the ON time with troublesome dyskinesia in a subject with Parkinson's disease; reducing the OFF time in a subject with Parkinson's disease; treating a hypokinetic disorder in a subject with Multiple Sclerosis; reducing gastrointestinal (GI) adverse events in a subject undergoing treatment with amantadine or a pharmaceutically acceptable salt thereof; or reducing sleep disturbances in a subject undergoing treatment with amantadine or a pharmaceutically acceptable salt thereof, the total once daily dose of amantadine administered is about 68.5 mg, about 137 mg, about 205.5 mg, about 274 mg of amantadine, from about 60 mg to about 80 mg, from about 120 mg to about 155 mg, from about 185 mg to about 230 mg, or from about 245 mg to about 305 mg of amantadine, or an equivalent amount of a pharmaceutically acceptable salt thereof. In some embodiments, the total once daily dose administered is about 85 mg, about 170 mg, about 255 mg, about 340 mg from about 75 mg to about 95 mg, from about 150 mg to about 190 mg, from about 230 mg to about 285 mg, or from about 305 to about 375 mg of amantadine hydrochloride. In some embodiments, the once daily dose is administered at night. In certain embodiments, the once daily dose is administered from 0 to 4 hours before bedtime, or from 0 to 3 hours before bedtime. In certain embodiments, the once daily dose is administered in the day. In some embodiments, the total daily dose is administered as 1, 2, or 3 separate dosage units, such as separate capsules. In certain embodiments, each dosage unit comprises about 68.5 mg, about 137 mg, from about 60 mg to about 155 mg, from about 60 mg to about 80 mg, or from about 120 mg to about 155 mg amantadine, or an equivalent amount of a pharmaceutically acceptable salt thereof. In certain embodiments, each dosage unit comprises about 85 mg, about 170 mg, from about 75 mg to about 190 mg, from about 75 mg to about 95 mg, or from about 150 mg to about 190 mg of amantadine hydrochloride. In certain embodiments, two or more dosage units comprising different amounts of amantadine or pharmaceutically acceptable salt thereof are administered, for example, one or more dosage units comprising about 68.5 mg, or from about 60 mg to about 155 mg amantadine or equivalent amount of a pharmaceutically acceptable salt thereof, and one or more dosage units comprising about 137 mg, or from about 120 mg to about 155 mg amantadine or an equivalent amount of a pharmaceutically acceptable salt thereof.

In specific embodiments described herein, a subject's entire daily dose of amantadine or a pharmaceutically acceptable salt thereof is administered once, during a period of less than about four, three, two or one hours before bedtime (e.g., after 4 p.m., or the time at which the subject wishes to go to sleep).

In some embodiments of any of the aspects herein, oral administration of the composition to a subject with Parkinson's disease results in a significant reduction in one or more Parkinson's disease symptoms or motor fluctuations. In some specific embodiments, administration of the composition results in about 5%, 10%, 15%, 20%, 25%, 30%, 35%, or 40% reduction in one or more Parkinson's disease symptoms or motor fluctuations. In further specific embodiments, the reduction in Parkinson's symptoms or motor fluctuations is measured on a numerical scale used by or accepted by the FDA or other regulatory agencies to evaluate the effectiveness of and to approve for licensure drugs for the treatment of Parkinson's symptoms or motor fluctuations. In further specific embodiments, the scale used in measuring the reduction in Parkinson's symptoms motor fluctuations could be the Unified Parkinson's Disease Rating Scale (UPDRS). Unified Parkinson's Disease Rating Scale (UPDRS, MDS revision)—Part I: non-motor aspects of experiences of daily living (13 items), —Part II: motor aspects of experiences of daily living (13 items)—Part III: motor examination (33 scored items), Hoehn and Yahr Staging Scale (Original or Modified), or PD Home Diary: total ON time or total OFF time.

In some embodiments of any of the aspects herein, oral administration of the composition to a subject with Parkinson's disease results in a significant reduction in levodopa induced dyskinesia. In a specific embodiment, administration of the composition results in about 5%, 10%, 15%, 20%, 25%, 30%, 35%, 40%, 45%, 50%, 55%, 60%, 65%, 70%, 75% or 80% reduction in levodopa induced dyskinesia. In further embodiments, the reduction in levodopa induced dyskinesia is measured on a numeric scale that is used by or accepted by the FDA or other regulatory agencies to evaluate effectiveness of and to approve for licensure drugs for the treatment of LID. In further specific embodiments, the scale used in measuring the reduction in LID could be UDysRS, UPDRS Part IV (subscores 32, 33), MDS-UPDRS Part IV, total and items 4.1 and 4.2, Dyskinesia Rating Scale (DRS), Abnormal Involuntary Movement Scale (AIMS), Rush Dyskinesia Rating Scale, Parkinson Disease Dyskinesia Scale (PDYS-26), Obeso Dyskinesia Rating Scale (CAPIT), Clinical Dyskinesia Rating Scale (CDRS), Lang-Fahn Activities of Daily Living Dyskinesia or other scales developed for this purpose. In other specific embodiments, the reduction in LID is measured relative to placebo in a controlled clinical trial. In other embodiments, the reduction in LID is measured relative to baseline in a controlled clinical trial.

In some embodiments of any of the aspects herein, oral administration of the composition to a subject with Parkinson's disease results in a significant reduction in Parkinson's disease fatigue. In a specific embodiment, administration of the composition results in about 5%, 10%, 15%, 20%, 25%, 30%, 35%, 40%, 45%, 50%, 55%, or 60% reduction in Parkinson's disease fatigue. In further specific embodiments, the reduction fatigue is measured on a numeric scale that is used by or accepted by the FDA or other regulatory agencies to evaluate the effectiveness of and to approve for licensure drugs for the treatment of fatigue. In further specific embodiments, the scale used in measuring the reduction in fatigue could be the Fatigue Severity Scale (FSS), Fatigue Assessment Inventory, Functional Assessment of Chronic Illness Therapy-Fatigue (FACIT Fatigue), Multidimensional Fatigue Inventory (MFI-20), Parkinson Fatigue Scale (PFS-16) and the Fatigue Severity Inventory. In other specific embodiments, the reduction in fatigue is measured relative to placebo in a controlled clinical trial. In other embodiments, the reduction in fatigue is measured relative to baseline in a controlled clinical trial.

In some embodiments of any of the aspects herein, oral administration of the composition to a subject results in a significant improvement in clinicians overall impression. In some specific embodiments, administration of the composition results in about a 0.5, 1.0, 1.5, 2.0, 2.5 or 3.0 point improvement in clinicians overall impression using a 7 point scale (or proportionate changes using a different scale). In further specific embodiments, the improvement in clinicians overall impression is measured on a numeric scale that is used by or accepted by the FDA or other regulatory agencies to evaluate the effectiveness of and to approve for licensure drugs indicated for subjects with Parkinson's disease. In further specific embodiments, the scale used in measuring the improvement in clinicians overall impression could be the Clinicians Global Impression of Change Rating Scale (CGIC). In other specific embodiments, the improvement in clinicians overall impression is measured relative to placebo in a controlled clinical trial. In other embodiments, the improvement in clinicians overall impression is measured relative to baseline in a controlled clinical trial.

II. Pharmaceutical Composition Formulations

As described herein, provided herein are oral pharmaceutical compositions comprising amantadine, or a pharmaceutically acceptable salt thereof, and a pharmaceutically acceptable excipient. For example, the pharmaceutical composition may be administered orally; may be suitable for, formulated for, or intended for oral delivery; or suitable for, formulated for, or intended for oral administration. In certain embodiments, the pharmaceutical composition is an extended release formulation.

Extended release oral pharmaceutical compositions suitable for use in the methods described herein can be made using a variety of extended release technologies, such as those described in the patent publications referenced in the above background section, which publications are incorporated herein by reference in their entireties. In some embodiments, the pharmaceutical composition comprises a pellet-in-capsule dosage form. In some embodiments, the pellets are a plurality of coated core seeds, wherein each coated core seed comprise a core seed, a drug coating surrounding the core seed, and an extended release coating surrounding the drug coating. In some embodiments, one or more additional coatings are present. For example, in some embodiments, the core seed further comprises a seal coating surrounding the drug coating, wherein the seal coating is surrounded by the extended release coating.

The drug coating may comprise amantadine, or a pharmaceutically acceptable salt thereof, and one or more pharmaceutically acceptable excipients. In some embodiments, the one or more pharmaceutically acceptable excipients comprise one or more binders, or one or more anti-tack agents, or any combinations thereof.

The extended release coating may comprise one or more release modifying excipients. In some embodiments, the extended release coating further comprises one or more plasticizers, or one or more pore-forming agents, or any combinations thereof. In certain embodiments, the one or more release modifying excipients comprise ethyl cellulose, and the one or more pore-forming agent comprise povidone, HPMC, or Eudragit, or combinations thereof.

The seal coating may comprise at one or more film-forming polymers. The seal coating may further comprise one or more anti-tack agents, one or more binders, or any combinations thereof. In some embodiments, the one or more film-forming polymers comprise HPMC, copovidone, or povidone, or combinations thereof.

In some embodiments, the coated core seed comprises more than one drug coating, or more than one extended release coating, or a combination thereof. For example the coated core seed may comprise a first drug coating surrounding the core seed, a seal coating surrounding the first drug coating, an additional drug coating surrounding the seal coating, and an extended release coating surrounding the seal coating. In another example, the coated core seed comprises a drug coating surrounding the core seed, a first extended release coating surrounding the drug coating, and an additional extended release coating surrounding the first extended release coating. The first and additional extended release coatings may, for example, comprise different components, or different ratios of components, or a combination thereof.

It should be understood that one or more of the coatings described herein, for example the drug coating, the seal coating, or the extended release coating, may in some embodiments fully surround the core seed, and in other embodiments surround almost all of the core seed, or the majority of the core seed, for example wherein at least 90%, at least 95%, at least 98%, at least 99%, or at least 99.9% of the surface area the core seed is surrounded by the coating. One or more of the coatings may be of uniform thickness, or may vary in thickness.

In some embodiments, the oral pharmaceutical composition comprises a plurality of coated core seeds. In some embodiments, the coated core seeds have an average diameter of, for example, 300 to 1700 microns, or 500 to 1200 microns. The core seeds of the coated core seeds may comprise for example, one or more inert compounds, such as sugar (e.g., sucrose), microcrystalline cellulose, or starch. In some embodiments, the core seed is generally spherical in shape. In some embodiments, the core seed is a sphere. In some embodiments, the core seed is generally ovoid in shape. In some embodiments, the core seed is an ovoid. In certain embodiments, the core seed comprises sugar (for example, sucrose), a microcrystalline cellulose (MCC), or a starch. In certain embodiments, the core seeds have an average diameter of 300 to 500 microns. In some embodiments, the coated core seeds can be prepared by processes such as pelletization, extrusion, spheronization, etc. or combinations thereof.

In some embodiments, the coated core seeds comprise less than 6000 ppm, less than 5500 ppm, less than 5000 ppm, less than 4500 ppm, less than 4000 ppm, less than 3500 ppm, less than 3000 ppm, less than 2500 ppm, less than 2000 ppm, less than 1500 ppm, or less than 1200 ppm organic solvent. In certain embodiments, the organic solvent is alcohol, such as isopropyl alcohol. Thus, in some embodiments, the coated core seeds comprise less than 6000 ppm of an organic solvent, such as alcohol, for example isopropyl alcohol. As described herein, in some embodiments the coated core seeds comprise one or more drug coatings, one or more extended release coatings, and one or more seal coatings. In some embodiments, the organic solvent is a linear or cyclic ketone (e.g., acetone, methyl ethyl ketone, etc.) In some embodiments, the organic solvent is a sulfoxide (e.g., dimethyl sulfoxide, etc). In some embodiments, the organic solvent is an amide (e.g., dimethyl formamide, N-methyl pyrrolidone, hexamethyl phosphorous triamide (HMPT), etc.). In some embodiments, the organic solvent is a linear or cyclic ether (e.g., tetrahydrofuran, diethyl ether, bis(2-methoxyethyl) ether (diglyme), dimethoxy ethane (glyme), 1,4-dioxane, etc.). In some embodiments, the organic solvent is a phosphoramide (e.g., hexamethyl phosphoramide (HPMA), etc.). In some embodiments, the organic solvent is a chlorinated hydrocarbon (e.g., chloroform, dichloromethane, dichloro ethane, carbon tetrachloride, etc.). In some embodiments, the organic solvent is a glycol (e.g., ethylene glycol, diethylene glycol, propylene glycol, etc.). In some embodiments, the organic solvent is a, nitrogen-containing solvent (e.g., pyridine, acetonitrile, etc.). In some embodiments, the organic solvent is an alcohol (e.g., a $C_1$-$C_6$ alcohol (e.g., ethanol, methanol, isopropanol, 1-butanol, 2-butanol, glycerol), such as isopropyl alcohol. In some embodiments, mixtures of two or more solvents can be used. In some embodiments of the levels of organic solvent described herein, the provided level refers to the total amount of two or more organic solvents.

It should be understood that while some embodiments of the compositions described herein comprise less than a certain level of organic solvent (such as less than 6,000 ppm, or less than 2,000 ppm), organic solvent may, in some embodiments, be used in one or more steps during manufacture of the composition. In certain embodiments, the solvent level present during one or more of the steps of manufacture may be higher than the solvent level present in the final composition.

A. Drug Coating

The coated core seeds comprise a core seed and a drug coating surrounding the core seed, wherein the drug coating comprises amantadine or a pharmaceutically acceptable salt thereof. The drug coating may further comprise one or more pharmaceutically acceptable excipients, such as one or more binders, or one or more anti-tack agents. In some embodiments, the drug coating comprises one or more binders selected from the group consisting of hydroxypropyl methyl cellulose, copovidone, povidone, hydroxypropyl cellulose, hydroxyethyl cellulose, methyl cellulose, and carboxymethyl cellulose. In some embodiments, the drug coating comprises one or more anti-tack agents. For example, the drug coating may comprise one or more anti-tack agents selected from the group consisting of magnesium stearate, calcium silicate, magnesium silicate, colloidal silicon dioxide, and talc. In some embodiments, the drug coating comprises one or more anti-tack agents selected from the group consisting of talc and magnesium stearate. In certain embodiments, the drug coating comprises one or more additional excipients.

In some embodiments, the drug coating comprises amantadine, or a pharmaceutically acceptable salt thereof, one or more pharmaceutically acceptable excipients; and one or more anti-tack agents. In some embodiments, the drug coating comprises amantadine, or a pharmaceutically acceptable salt thereof; at least two pharmaceutically acceptable excipients; and one or more anti-tack agents. In some embodiments, the one or more, or at least two, pharmaceutically acceptable excipients comprise one or more binders. In some embodiments, the one or more, or at least two pharmaceutically acceptable excipients are binders. In a certain embodiment, the drug coating comprises amantadine, or a pharmaceutically acceptable salt thereof; one or more binders; and one or more anti-tack agents. In some embodiments, the pharmaceutically acceptable salt of amantadine is amantadine hydrochloride. In another embodiment, the pharmaceutically acceptable salt of amantadine is amantadine sulfate.

In some embodiments, the drug coating comprises from 60 wt % to 85 wt %, from 65 wt % to 80 wt %, or from 70 wt % to 75 wt % of a pharmaceutically acceptable salt of amantadine; from 15 wt % to 35 wt %, or from 20 wt % to 30 wt % of one or more binders; and from 1 wt % to 5 wt %, or from 2 wt % to 4 wt % of one or more anti-tack agents. In some embodiments, the pharmaceutically acceptable salt of amantadine is amantadine hydrochloride; the one or more binders are hydroxypropyl methyl cellulose and copovidone; and the one or more anti-tack agents are talc. In some embodiments, the drug coating comprises amantadine, or a pharmaceutically acceptable salt thereof; hydroxypropyl methyl cellulose; copovidone; and talc. In some embodiments, the drug coating comprises from 60 wt % to 85 wt %, from 65 wt % to 80 wt %, or from 70 wt % to 75 wt % of a pharmaceutically acceptable salt of amantadine; from 15 wt % to 25 wt %, or from 18 wt % to 22 wt % of hydroxypropylmethyl cellulose; from 2 wt % to 7 wt %, or from 3 wt % to 6 wt % of copovidone; and from 1 wt % to 5 wt %, or from 2 wt % to 4 wt % of talc.

In certain embodiments, the drug coating comprises less than 6000 ppm, less than 5500 ppm, less than 5000 ppm, less than 4500 ppm, less than 4000 ppm, less than 3500 ppm, less than 3000 ppm, less than 2500 ppm, less than 2000 ppm, less than 1500 ppm, or less than 1200 ppm organic solvent. In certain embodiments, the organic solvent is alcohol, for example isopropyl alcohol. In some embodiments, the organic solvent is a linear or cyclic ketone (e.g., acetone, methyl ethyl ketone, etc.) In some embodiments, the organic solvent is a sulfoxide (e.g., dimethyl sulfoxide, etc). In some embodiments, the organic solvent is an amide (e.g., dimethyl formamide, N-methyl pyrrolidone, hexamethyl phosphorous triamide (HMPT), etc.). In some embodiments, the organic solvent is a linear or cyclic ether (e.g., tetrahydrofuran, diethyl ether, bis(2-methoxyethyl) ether (diglyme), dimethoxy ethane (glyme), 1,4-dioxane, etc.). In some embodiments, the organic solvent is a phosphoramide (e.g., hexamethyl phosphoramide (HPMA), etc.). In some embodiments, the organic solvent is a chlorinated hydrocarbon (e.g., chloroform, dichloromethane, dichloro ethane, carbon tetrachloride, etc.). In some embodiments, the organic solvent is a glycol (e.g., ethylene glycol, diethylene glycol, propylene glycol, etc.). In some embodiments, the organic solvent is a, nitrogen-containing solvent (e.g., pyridine, acetonitrile, etc.). In some embodiments, the organic solvent is an alcohol (e.g., a $C_1$-$C_6$ alcohol (e.g., ethanol, methanol, isopropanol, 1-butanol, 2-butanol, glycerol), such as isopropyl alcohol. In some embodiments, mixtures of two or more solvents can be used. In some embodiments of the levels of organic solvent described herein, the provided level refers to the total amount of two or more organic solvents.

In some embodiments, the core seeds are coated with a drug coat comprising amantadine or a pharmaceutically acceptable salt thereof, and optionally one or more binders, anti-tack agents and/or solvents by conventional coating techniques such as fluidized bed coating, pan coating. In some embodiments, the solvents exclude organic solvents. In other embodiments, the solvent for the drug coating composition consists of water.

B. Extended Release Coating

The coated core seeds further comprise an extended release coating, wherein the extended release coating surround the drug coating. The extended release coating may be formulated to delay release of the drug from the coated core seeds for a period of time after introduction of the dosage form into the use environment. The extended release coating comprises one or more release modifying excipients. For example, the extended release coating may comprise one or more pH-dependent or non-pH-dependent release modifying excipients, or a combination thereof. Examples of non-pH-dependent extended release polymers include ethyl cellulose, hydroxypropylmethyl cellulose, hydroxyethyl cellulose, hydroxypropyl cellulose, carboxymethyl cellulose, copolymer of ethyl acrylate, and methyl methacrylate (e.g., Eudragit RS). Examples of pH-dependent release modifying excipients include methacrylic acid copolymers, hydroxypropylmethyl cellulose acetate succinate, hydroxypropylmethyl cellulose phthalate, and cellulose acetate phthalate. The extended release coating may further comprise one or more pore-forming agents. Example of pore-forming agents include povidone; polyethylene glycol; hydroxypropyl cellulose; hydroxypropylmethyl cellulose; sugars, such as sucrose, mannitol, and lactose; and salts, such as sodium chloride and sodium citrate. The extended release coating may further comprise one or more plasticizers, such as acetylated citrated esters, acetylated glycerides, castor oil, citrate esters, dibutylsebacate, glyceryl monostearate, diethyl phthalate, glycerol, medium chain triglycerides, propylene glycol, or polyethylene glycol. The extended release coating may also include one or more additional excipients, for example one or more lubricants, one or more anti-tack agents. For example, in some embodiments, the extended release coating comprises one or more excipients selected from the group consisting of magnesium stearate, calcium silicate, magnesium silicate, colloidal silicon dioxide and talc. In some embodiments, the extended release coating comprises one or more lubricants such as magnesium stearate or talc.

As described herein, the extended release coating comprising one or more release modifying excipients. Release modifying excipients may include, but are not limited to, insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkyl celluloses such as hydroxypropyl cellulose, hydroxypropylmethyl cellulose, sodium carboxymethyl cellulose, and cross-linked acrylic acid polymers like Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof. In certain embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers. In certain other embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups. In still other embodiments, the acrylic polymer is an acrylic resin lacquer such as that which is commercially available from Rohm Pharma under the trade name Eudragit®. In further embodiments, the acrylic polymer comprises a mixture of two acrylic resin lacquers commercially available from Rohm Pharma under the trade names Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit RL30D and 1:40 in Eudragit® RS30D. The mean molecular weight is about 150,000. Eudragit® S-100 and Eudragit® L-100 are also suitable for use herein. The code designations RL (high permeability) and RS (low permeability) refer to the permeability properties of these agents. Eudragit® RL/RS mixtures are insoluble in water and in digestive fluids. However, multiparticulate systems formed to include the same are swellable and permeable in aqueous solutions and digestive fluids. The polymers described above such as Eudragit® RL/RS may be mixed together in any desired ratio in order to ultimately obtain an extended release formulation having a desirable dissolution profile. One skilled in the art will recognize that other acrylic polymers may also be used, such as, for example, Eudragit® L.

As described herein, in some embodiments the extended release coating comprises one or more pore-forming agents (e.g., pore formers). Pore-forming agents suitable for use in the extended release coating can be organic or inorganic agents, and may include materials that can be dissolved, extracted or leached from the coating in the environment of use. Examples of pore-forming agents include but are not limited to organic compounds such as mono-, oligo-, and polysaccharides including sucrose, glucose, fructose, mannitol, mannose, galactose, lactose, sorbitol, pullulan, dextran; polymers soluble in the environment of use such as water-soluble hydrophilic polymers, such as povidone, crospovidone, polyethylene glycol, hydroxypropyl cellulose, hydroxypropylmethyl cellulose, hydroxyalkyl celluloses, carboxyalkyl celluloses, cellulose ethers, acrylic resins, polyvinylpyrrolidone, cross-linked polyvinylpyrrolidone, polyethylene oxide, carbowaxes, Carbopol®, and the like, diols, polyols, polyhydric alcohols, polyalkylene glycols, polyethylene glycols, polypropylene glycols, or block polymers thereof, polyglycols, poly($\alpha$-$\Omega$) alkylenediols; inorganic compounds such as alkali metal salts, lithium carbonate, sodium chloride, sodium bromide, potassium chloride, potassium sulfate, potassium phosphate, sodium acetate, sodium citrate, suitable calcium salts, and the like. In certain embodiments, plasticizers can also be used as a pore forming agent. In some embodiments, the release modifying excipient is ethyl cellulose. In certain embodiments, the pore forming agent is povidone, HPMC, or Eudragit®, or any combinations thereof.

In some embodiments, the extended release coating comprises one or more release modifying excipients; one or more pore forming agents, and one or more plasticizers. In some embodiments, the extended release coating comprises between 65 wt % to 95 wt %, or between 70 wt % to 90 wt %, or between 75 wt % to 85 wt % of one or more release modifying excipients; between 5 wt % to 15 wt %, or between 8 wt % to 12 wt % of one or more pore forming agents; and between 5 wt % to 15 wt %, or between 8 wt % to 12 wt % of one or more plasticizers. In some embodiments, the one or more release modifying excipients is ethyl cellulose; the one or more pore forming agents is povidone, HPMC, or Eudragit®, or a mixture thereof, and the one or more plasticizers is medium chain triglycerides. Thus, in some embodiments, the extended release coating comprises between 65 wt % to 95 wt %, or between 70 wt % to 90 wt %, or between 75 wt % to 85 wt % of ethyl cellulose; between 5 wt % to 15 wt %, or between 8 wt % to 12 wt % of povidone; and between 5 wt % to 15 wt %, or between 8 wt % to 12 wt % of medium chain triglycerides.

In certain embodiments, the extended release coating comprises less than 6000 ppm, less than 5500 ppm, less than 5000 ppm, less than 4500 ppm, less than 4000 ppm, less than 3500 ppm, less than 3000 ppm, less than 2500 ppm, less than 2000 ppm, less than 1500 ppm, or less than 1200 ppm organic solvent. In certain embodiments, the organic solvent is alcohol, for example isopropyl alcohol. In some embodiments, the organic solvent is a linear or cyclic ketone (e.g., acetone, methyl ethyl ketone, etc.) In some embodiments, the organic solvent is a sulfoxide (e.g., dimethyl sulfoxide, etc). In some embodiments, the organic solvent is an amide (e.g., dimethyl formamide, N-methyl pyrrolidone, hexamethyl phosphorous triamide (HMPT), etc.). In some embodiments, the organic solvent is a linear or cyclic ether (e.g., tetrahydrofuran, diethyl ether, bis(2-methoxyethyl) ether (diglyme), dimethoxy ethane (glyme), 1,4-dioxane, etc.). In some embodiments, the organic solvent is a phosphoramide (e.g., hexamethyl phosphoramide (HPMA), etc.). In some embodiments, the organic solvent is a chlorinated hydrocarbon (e.g., chloroform, dichloromethane, dichloro ethane, carbon tetrachloride, etc.). In some embodiments, the organic solvent is a glycol (e.g., ethylene glycol, diethylene glycol, propylene glycol, etc.). In some embodiments, the organic solvent is a, nitrogen-containing solvent (e.g., pyridine, acetonitrile, etc.). In some embodiments, the organic solvent is an alcohol (e.g., a $C_1$-$C_6$ alcohol (e.g., ethanol, methanol, isopropanol, 1-butanol, 2-butanol, glycerol), such as isopropyl alcohol. In some embodiments, mixtures of two or more solvents can be used. In some embodiments of the levels of organic solvent described herein, the provided level refers to the total amount of two or more organic solvents.

Extended release coating can be applied using conventional coating techniques such as fluidized bed coating, pan coating etc. The drug coated core seeds, which optionally comprise a seal coat, may be coated with the extended release coating by fluidized bed coating.

C. Additional Coatings

In some embodiments, the coated core seeds comprise one or more additional coatings, for example a seal coat. In some embodiments, the seal coat is formulated to prevent one or more components of the extended release coating from interacting with one or more components of the core seed, or to prevent migration of one or more components of the core seed and/or drug coating from diffusing into the extended release coating. The seal coating may comprise one or more film forming polymers including but not limited to hydroxypropylmethyl cellulose (HPMC), copovidone, povidone, polyvinyl pyrrolidone, hydroxypropyl cellulose, hydroxyethyl cellulose, methyl cellulose, carboxymethyl cellulose or any combinations thereof, and the like.

The seal coating may further comprise one or more additional pharmaceutically acceptable excipients. For example, the seal coating may comprise one or more plasticizers, such as propylene glycol, triacetin, polyethylene glycol, or tributyl citrate, or any combination thereof; or one or more anti-tack agents, such as magnesium stearate, calcium silicate, magnesium silicate, colloidal silicon dioxide or talc, or any combinations thereof. In some embodiments, the film forming polymer is HPMC, copovidone, povidone, or a combination thereof. In some embodiments, the film forming polymer is HPMC.

The seal coating may further comprise one or more buffers, colorants, opacifiers, surfactants or bases, which are known to those skilled in the art.

In certain embodiments, the seal coating comprises one or more film forming polymers and one or more anti-tack agents. In some embodiments, the seal coating comprises from 80 wt % to 100 wt %, or from 85 wt % to 95 wt % of one or more film forming polymers; and from 0 wt % to 20 wt %, or from 5 wt % to 15 wt % or from 7 wt % to 13 wt % of one or more anti-tack agents. In certain embodiments, the seal coating comprises hydroxpropyl methyl cellulose and talc. In some embodiments, the seal coating comprises from 80 wt % to 100 wt %, or from 85 wt % to 95 wt % hydroxypropyl methyl cellulose; and from 0 wt % to 20 wt %, or from 5 wt % to 15 wt % or from 7 wt % to 13 wt % talc.

In certain embodiments, the seal coating comprises less than 6000 ppm, less than 5500 ppm, less than 5000 ppm, less than 4500 ppm, less than 4000 ppm, less than 3500 ppm, less than 3000 ppm, less than 2500 ppm, less than 2000 ppm, less than 1500 ppm, or less than 1200 ppm organic solvent. In certain embodiments, the organic solvent is alcohol, for example isopropyl alcohol. In some embodiments, the organic solvent is a linear or cyclic ketone (e.g., acetone, methyl ethyl ketone, etc.) In some embodiments, the organic solvent is a sulfoxide (e.g., dimethyl sulfoxide, etc.). In some embodiments, the organic solvent is an amide (e.g., dimethyl formamide, N-methyl pyrrolidone, hexamethyl phosphorous triamide (HMPT), etc.). In some embodiments, the organic solvent is a linear or cyclic ether (e.g., tetrahydrofuran, diethyl ether, bis(2-methoxyethyl) ether (diglyme), dimethoxy ethane (glyme), 1,4-dioxane, etc.). In some embodiments, the organic solvent is a phosphoramide (e.g., hexamethyl phosphoramide (HPMA), etc.). In some embodiments, the organic solvent is a chlorinated hydrocarbon (e.g., chloroform, dichloromethane, dichloroethane, carbon tetrachloride, etc.). In some embodiments, the organic solvent is a glycol (e.g., ethylene glycol, diethylene glycol, propylene glycol, etc.). In some embodiments, the organic solvent is a, nitrogen-containing solvent (e.g., pyridine, acetonitrile, etc.). In some embodiments, the organic solvent is an alcohol (e.g., a $C_1$-$C_6$ alcohol (e.g., ethanol, methanol, isopropanol, 1-butanol, 2-butanol, glycerol)), such as isopropyl alcohol. In some embodiments, mixtures of two or more solvents can be used. In some embodiments of the levels of organic solvent described herein, the provided level refers to the total amount of two or more organic solvents.

Seal coating can be applied to the core seeds using conventional coating techniques such as fluidized bed coating, pan coating etc. In some embodiments, the drug coated core seeds are coated with a seal coat coating that optionally comprises one or more binders, anti-tack agents and/or solvents by fluidized bed coating or pan coating. In certain embodiments, the solvents exclude organic solvents. In some embodiments, the solvent for the seal coating composition consists of water.

D. Binders

In some embodiments, the drug coating, or the additional coating, if present, or any combinations thereof, comprise one or more binders (e.g., film forming polymers). For example, as described herein the drug coating comprises one or more pharmaceutically acceptable excipients, wherein the one or more pharmaceutically acceptable excipients may comprise a binder. Suitable binders for use herein may include alginic acid and salts thereof; cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinylpyrrolidone/vinyl acetate copolymer; crospovidone; povidone; starch; pregelatinized starch; dextrin; a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isapol husks, polyvinylpyrrolidone (e.g., Polyvidone® CL, Kollidon® CL, Polyplasdone® XL-10), larch arabogalactan, Veegum®, polyethylene glycol, waxes, sodium alginate, and the like.

E. Capsules

In some embodiments, the oral pharmaceutical compositions herein further comprise a capsule shell, wherein the plurality of coated core seeds is encapsulated within the capsule shell. The coated core seeds may be introduced into a suitable capsule shell by using an encapsulator equipped with pellet dosing chamber. The capsule sizes may be 00, 0, 0EL, 1, 1EL, 2, 2EL, 3, 4 or 5. In some embodiments, a unit dose of an oral pharmaceutical composition is encapsulated within one capsule shell. In other variations, a unit dose of an oral pharmaceutical composition as described herein is encapsulated within a plurality of separate capsule shells, for example split between two capsule shells.

In some embodiments, the composition that provides pharmacokinetic properties and plasma concentration profiles is a pellet-in-capsule composition wherein the pellets are a plurality of coated core seeds that have a diameter of about 500 µm to 1.2 mm, and preferably about 700 µm to 1000 µm, where each coated core seed comprises a core seed; a drug coating surrounding the core seed and comprising amantadine or a pharmaceutically acceptable salt thereof and a pharmaceutically acceptable excipient; and an extended release coating surrounding the drug coating, and comprising a release modifying excipient. In some embodiments, the extended release coating extends release of the amantadine or a pharmaceutically acceptable salt thereof so as to provide the desired pharmacokinetic properties and amantadine plasma concentration profiles described herein.

In some embodiments, the plurality of coated core seeds in the pellet-in-capsule formulation are in a size 0 or smaller, preferably a size 1 or smaller capsule. Mean coated core seed diameters in some embodiments may be in a range of 500 µm to 1200 µm, e.g., from 500 µm to 1100 µm, from 500 µm to 1000 µm, from 500 µm to 900 µm, from 500 µm to 800 µm, from 500 µm to 700 µm, from 600 µm to 1100 µm, from 600 µm to 1000 µm, from 600 µm to 900 µm, from 600 µm to 800 µm, from 600 µm to 700 µm, from 700 µm to 1100 µm, from 700 µm to 1000 µm, from 700 µm to 900 µm, or from 700 µm to 800 µm. In some embodiments the mean particle diameters are, ±10%, e.g.: 500 µm, 550 µm, 600 µm, 650 µm, 700 µm, 750 µm, 800 µm, 850 µm, 900 µm, 950 µm, 1000 µm, 1050 µm, 1100 µm, 1150 µm or 1200 µm.

In some embodiments, the composition of the disclosure is an oral pharmaceutical composition, comprising a plurality of coated core seeds encapsulated within a capsule shell, wherein each coated core seed comprises a core seed; a drug coating amantadine, or a pharmaceutically acceptable salt thereof, and one or more pharmaceutically acceptable excipients, wherein the one or more pharmaceutically acceptable excipients is one or more binders, and wherein the drug coating surrounds the core seed; and an extended release coating surrounding the drug coating, wherein the extended release coating comprising a release modifying excipient (such as ethyl cellulose), a pore forming agent (such as hydroxypropyl methyl cellulose or povidone), and a plasticizer. In some embodiments, the coated core seeds may further comprise a seal coating surrounding the drug coating, wherein the extended release coating surrounds the seal coating. The coated core seeds may be prepared using methods known in the art, such as those described in Example 2 below.

In a specific embodiment, based on the combined weight of the plurality of coated core seeds, amantadine or a pharmaceutically acceptable salt thereof is present in amounts from 20-80 wt %, 45-70 wt %, 40-50 wt %, 45-55 wt %, 50-60 wt %, 55-65 wt %, 60-70 wt %, 65-75 wt %, 70-80 wt %, or 40 to 60 wt %; the one or more pharmaceutically acceptable excipients (such as one or more binders, for example hydroxypropyl methyl cellulose, copovidone, or mixtures thereof) is present in amounts from 1 to 25 wt %; the core seed, for example a sugar sphere (nonpareil) or microcrystalline cellulose seed (e.g., Celphere®), is present in amounts from 8 to 25 wt %; the extended release coating comprises one or more release modifying excipients, one or more pore forming agents, and one or more plasticizers, wherein the release modifying excipient comprises ethyl cellulose present in amounts from 10 to 20 wt %, the pore forming agent, preferably povidone, is present in amounts from 1 to 4 wt %, and the plasticizer is present in amounts from 1 to 4 wt %. In another specific embodiment, based on the combined weight of the plurality of coated core seeds, the amantadine or pharmaceutically acceptable salt thereof is present in amounts from 50 to 70 wt %; the one or more pharmaceutically acceptable excipients (such as one or more binders, for example hydroxypropyl methyl cellulose, copovidone, or mixtures thereof) is present in amounts from 1 to 25 wt %; the core seed, for example a sugar sphere (nonpareil) or microcrystalline cellulose seed (e.g., Celphere®), is present in amounts from 5 to 15 wt %; the one or more release modifying excipients in the extended release coating is ethyl cellulose and is present in amounts from 1 to 15 wt %; the extended release coating comprises pore forming agent (such as povidone) which is present in amounts from 0.25 to 4 wt %; and the extended release coating comprises a plasticizer, which is present in amounts from 0.25 to 4 wt %.

In some embodiments, provided herein is an oral pharmaceutical composition, comprising a plurality of coated core seeds and at least one capsule shell, wherein at least a portion of the core seeds are encapsulated within the capsule shell. In some embodiments, the plurality of the coated core seeds are encapsulated in two separate capsule shells. In some embodiments, the plurality of coated core seeds comprise core seeds, wherein the core seeds comprise microcrystalline cellulose from 5 wt % to 20 wt %, or from 10 wt % to 15 wt %, or about 12.44 wt % of the composition. In some embodiments, the coated core seeds comprise a drug coating surrounding each core seed, wherein the drug coating comprises amantadine, or a pharmaceutically acceptable salt thereof from 20 wt % to 60 wt %, or from 30 wt % to 50 wt %, or from 40 wt % to 50 wt %, or about 43.54 wt % of the composition; the pharmaceutically acceptable excipients hydroxypropyl methyl cellulose from 5 wt % to 18 wt %, or from 8 wt % to 15 wt %, or about 11.61 wt %, and copovidone at from 1 wt % to 5 wt %, or from 2 wt % to 4 wt %, or about 2.9 wt % of the composition; and the anti-tack agent talc at from 1 wt % to 3 wt %, or from 1.5 wt % to 2.5 wt %, or about 2.17 wt % of the composition. In certain embodiment, the amantadine or a salt thereof is amantadine hydrochloride. In other embodiments, the coated core seeds comprise an extended release coating surrounding the drug coating, wherein the extended release coating comprises the release modifying excipient ethyl cellulose from 5 wt % to 25 wt %, or 10 wt % to 20 wt %, or about 15.91 wt % of the composition; the pore forming agent povidone at from 1 wt % to 3 wt %, or from 1.5 wt % go 2.5 wt %, or about 2.15 wt % of the composition; and the plasticizer medium chain triglycerides from 1 wt % to 3 wt %, or from 1.5 wt % go 2.5 wt %, or about 2.15 wt % of the composition. In certain embodiments, which may be combined with any of the previous embodiments, the coated core seeds comprise a seal coating surrounding the drug coating, wherein the extended release coating surrounds the seal coating, and the seal coating comprises the film-forming polymer hydroxpropyl methyl cellulose from 3 wt % to 10 wt %, or 5 wt % to 8 wt %, or about 6.6 wt % of the composition; and the anti-tack agent talc at from 0.25 wt % to 1 wt %, or from 0.5 wt % to 0.75 wt %, or about 0.66 wt % of the composition. In certain embodiments, the pharmaceutical composition further comprises magnesium stearate from 0.01 wt % to 0.2 wt %, or 0.08 wt % to 0.12 wt %, or about 0.1 wt % of the composition.

In some embodiments, the pharmaceutically acceptable salt of amantadine is amantadine hydrochloride. In another embodiment, the pharmaceutically acceptable salt of amantadine is amantadine sulfate. In some embodiments, which may be combined with any other embodiments, the oral pharmaceutical composition comprises amantadine in a unit dosage from 40 mg to 500 mg, 45 mg to 400 mg, from 50 mg to 350 mg, from 55 mg to 300 mg, from 60 mg to 290 mg, from 68.5 mg to 274 mg, from 50 mg to 80 mg, from 55 mg to 75 mg, from 60 mg to 70 mg, from 120 mg to 150 mg, from 135 mg to 145 mg, from 130 mg to 140 mg, from 250 mg to 300 mg, from 260 mg to 290 mg, from 270 mg to 280 mg, about 68.5 mg, about 137 mg, or about 274 mg, or comprises an equivalent amount of a pharmaceutically acceptable salt of amantadine. In some embodiments, the pharmaceutically acceptable salt of amantadine is amantadine hydrochloride. In another embodiment, the pharmaceutically acceptable salt of amantadine is amantadine sulfate. It should be clear to one of skill in the art how to calculate an "equivalent amount" of the salt of a compound, taking into account that the salt has an increased molecular weight. For example, in some embodiments, the composition comprises about 68.5 mg of amantadine, or an equivalent amount of the amantadine hydrochloride salt. Thus, in some embodiments, the composition comprises about 85 mg of amantadine hydrochloride. The unit dosage may be in a single capsule, or it may be across multiple capsules.

As described herein, in some embodiments, the pharmaceutical composition has a lower level of organic solvent than other compositions. In some embodiments, the pharmaceutical composition comprise a plurality of coated core seeds, wherein the plurality of coated core seeds has a lower level or organic solvent than other compositions. For example, in some embodiments, the pharmaceutical compositions provided herein, such as any of the embodiments disclosed herein, comprise a plurality of coated core seeds with less than 6000 ppm, less than 5500 ppm, less than 5000 ppm, less than 4500 ppm, less than 4000 ppm, less than 3500 ppm, less than 3000 ppm, less than 2500 ppm, less than 2000 ppm, less than 1500 ppm, or less than 1200 ppm organic solvent. In some embodiments, the pharmaceutical composition as described herein comprises less than 6000 ppm, less than 5500 ppm, less than 5000 ppm, less than 4500 ppm, less than 4000 ppm, less than 3500 ppm, less than 3000 ppm, less than 2500 ppm, less than 2000 ppm, less than 1500 ppm, or less than 1200 ppm organic solvent. In certain embodiments the organic solvent is alcohol. In some embodiments, the organic solvent is isopropyl alcohol. In other embodiments, the organic solvent comprises one or more compounds. For example, in some embodiments, the organic solvent comprises isopropyl alcohol and another alcohol. In some embodiments, the organic solvent is a linear or cyclic ketone (e.g., acetone, methyl ethyl ketone, etc.) In some embodiments, the organic solvent is a sulfoxide (e.g., dimethyl sulfoxide, etc.). In some embodiments, the organic solvent is an amide (e.g., dimethyl formamide, N-methyl pyrrolidone, hexamethyl phosphorous triamide (HMPT), etc.). In some embodiments, the organic solvent is a linear or cyclic ether (e.g., tetrahydrofuran, diethyl ether, bis(2-methoxyethyl) ether (diglyme), dimethoxy ethane (glyme), 1,4-dioxane, etc.). In some embodiments, the organic solvent is a phosphoramide (e.g., hexamethyl phosphoramide (HPMA), etc.). In some embodiments, the organic solvent is a chlorinated hydrocarbon (e.g., chloroform, dichloromethane, dichloroethane, carbon tetrachloride, etc.). In some embodiments, the organic solvent is a glycol (e.g., ethylene glycol, diethylene glycol, propylene glycol, etc.). In some embodiments, the organic solvent is a, nitrogen-containing solvent (e.g., pyridine, acetonitrile, etc.). In some embodiments, the organic solvent is an alcohol (e.g., a $C_1$-$C_6$ alcohol (e.g., ethanol, methanol, isopropanol, 1-butanol, 2-butanol, glycerol)), such as isopropyl alcohol. In some embodiments, mixtures of two or more solvents can be used. In some embodiments of the levels of organic solvent described herein, the provided level refers to the total amount of two or more organic solvents.

Additional embodiments of the disclosure are illustrated in the Table A, below, entitled "Various Amantadine ER Capsule Size 1 Formulations". By means of methods and compositions described herein, formulations can be made that achieve the desired dissolution characteristics and target pharmacokinetic profiles described herein. More specifically, therapeutically effective doses of amantadine or a pharmaceutically acceptable salt thereof can be administered once nightly in no more than two size 1 (or smaller, e.g., size 2 or 3) capsules using the manufacturing methods and compositions that have been described herein to achieve these results. In particular, higher drug loading can be achieved using compositions and manufacturing methods described herein. In some embodiments, higher drug loading may be achieved, with the required dissolution profile, using smaller coated core seed sizes and concomitantly increased thickness of the drug coating or multiple drug coatings on smaller core seeds, but with no change in the extended release coat. In some embodiments, using alternative manufacturing approaches described herein, e.g., extrusion and spheronization, even higher drug loads can be achieved to realize the desired dissolution profile, enabling high amantadine drug loads with suitable pharmacokinetic profiles, resulting in compositions that are therapeutically more effective, and at least as well tolerated, and can be filled in relatively small sized capsules (e.g., size 1, 2 or 3), enabling ease of administration to subjects.

TABLE A

Various Amantadine ER Capsule Size 1 Formulations

| AMT* Strength (mg) | Manufacture Method | Inert Core Pellet Size (mm) | Active Drug % w/w | Extended Release Coating % w/w | Bulk Density (g/cm$^3$) | % Fill in Size 1 Capsule |
|---|---|---|---|---|---|---|
| 85 mg | Fluid bed coating | 0.3-0.5 | 40-50% | 10-30% | 0.6-1.0 | 60-70% |
| 110 mg | Fluid bed coating | 0.3-0.5 | 40-50% | 10-30% | 0.6-1.0 | 60-70% |
| 140 mg | Fluid bed coating | 0.3-0.5 | 45-50% | 10-30% | 0.6-1.0 | 80-90% |
| 150 mg | Fluid bed coating | 0.3-0.5 | 50-55% | 10-30% | 0.6-1.0 | 80-90% |
| 170 mg | Fluid bed coating | 0.2-0.3 | 50-55% | 10-30% | 0.6-1.0 | 80-90% |
| 170 mg | Extrusion spheronization, pan or fluidized bed coating | N/A | 55-75% | 10-30% | 0.6-1.0 | 65-75% |
| 190 mg | Extrusion spheronization, pan or fluidized bed coating | N/A | 55-75% | 10-30% | 0.6-1.0 | 75-85% |
| 210 mg | Extrusion spheronization, pan or fluidized bed coating | N/A | 55-75% | 10-30% | 0.6-1.0 | 80-90% |
| 230 mg | Extrusion spheronization, pan or fluidized bed coating | N/A | 55-75% | 10-30% | 0.6-1.0 | 85-95% |

*"AMT" refers to amantadine hydrochloride

Suitable plasticizers include medium chain triglycerides, diethyl phthalate, citrate esters, polyethylene glycol, glycerol, acetylated glycerides, castor oil, and the like. The coated core seeds are filled into capsules to provide the desired strength of amantadine. An advantage of this composition is it provides the desired release properties that make the composition suitable for administration during said period before bedtime. A further advantage is that the extended release coating is sufficiently durable so that the capsule can be opened and the pellets sprinkled onto food for administration to subjects who have difficulty swallowing pills, without adversely affecting the release properties of the composition. When the composition is administered by sprinkling onto food, it is preferred to use a soft food such as applesauce or chocolate pudding, which is consumed within 30 minutes, and preferably within 15 minutes. In some embodiments, a yet further advantage of the composition described herein is that it has very good batch-to-batch reproducibility and shelf-life stability.

In some embodiments of the pellet-in-capsule composition of the disclosure, in addition to having the in vitro dissolution properties described herein and any of the pharmacokinetic properties provided herein (e.g., in vivo release profile, Tmax, Cmax/Cmin ratio, etc) that make the composition suitable for administration in said period before bedtime. The composition is further characterized by providing a Cmax of 1.3-2.4 ng/ml per mg of amantadine and an $AUC_{0\text{-}inf}$ of 42-75 ng*h/mL per mg of amantadine after oral administration of a single dose of the capsule to a human subject in a fasted state. In some embodiments, the pellet-in-capsule composition is further characterized by a steady state plasma concentration in which once nightly oral administration of the capsule to a human subject provides a Cmax of 2.4 to 4.2 ng/ml per mg of amantadine, a Cmin of 1.1 to 2.6 ng/ml per mg of amantadine, and an $AUC_{0\text{-}24}$ of 43-73 ng*h/mL per mg of amantadine.

The pellet-in-capsule compositions provided herein may be provided at a strength suitable for amantadine therapy. Typical strengths range from at least about 50 mg to about 250 mg. In a specific embodiment, the capsule strength of amantadine is 70 mg, 80 mg, 85 mg, 90 mg, 110 mg, 120 mg, 125 mg, 130 mg, 140 mg, 150 mg, 160 mg, 160 mg, 170 mg, 180 mg, 190 mg, 210 mg, or 220 mg, or an equivalent amount of a pharmaceutically acceptable salt thereof, that provides a single dose $AUC_{0\text{-}inf}$ per mg that is equivalent to a 100 mg tablet of an immediate release formulation of amantadine HCl (e.g., Symmetrel®, or other FDA Orange Book reference listed drug). In some embodiments, the capsule strength is 68.5 mg, 70 mg, 80 mg, 85 mg, 90 mg, 110 mg, 120 mg, 125 mg, 130 mg, 137 mg, 140 mg, 150 mg, 160 mg, 160 mg, 170 mg, 180 mg, 190 mg, 205.5 mg, 210 mg, or 220 mg of amantadine, or an equivalent amount of a pharmaceutically acceptable salt thereof, that provides a single dose $AUC_{0\text{-}inf}$ per mg that is equivalent to a 100 mg tablet of an immediate release formulation of amantadine HCl (e.g., Symmetrel®, or other FDA Orange Book reference listed drug). For example, in some embodiments, the capsule strength comprises 85 mg of amantadine hydrochloride or 170 mg of amantadine hydrochloride. One, two, or three, of such capsules can be administered to a subject in the period before bedtime. In some embodiments, between 220 mg and 650 mg of amantadine hydrochloride is administered using 2 capsules of a suitable ER formulations once nightly. In still further embodiments, the capsule strength is from about 60 mg to about 155 mg, about 60 mg to about 80 mg, or about 120 mg to about 155 mg of amantadine, or an equivalent amount of a pharmaceutically acceptable salt thereof. In certain embodiments, the capsule strength is from about 75 mg to about 190 mg, about 75 mg to about 95 mg, or about 150 mg to about 190 mg of amantadine, or an equivalent amount of a pharmaceutically acceptable salt thereof. One, two, or three, of such capsules can be administered to a subject in the period before bedtime.

III. Methods of Preparing

Also provided herein are methods of preparing the pharmaceutical compositions described herein. As discussed herein, in some embodiments, certain steps of the methods do not include an organic solvent. Avoiding the use of organic solvent in certain steps of the preparation may result in pharmaceutical compositions with a lower residual organic solvent level, and lower incidence of one or more gastrointestinal effects when administered to a subject. In some embodiments, the gastrointestinal effects are selected from the group consisting of abdominal distension, constipation, diarrhea, dyspepsia, gingival pain, dry lip, lower abdominal pain, nausea, stomach discomfort, toothache, upper abdominal pain, and vomiting.

As described herein, in some embodiments, the pharmaceutical compositions provided herein comprise a plurality of coated core seeds comprising core seeds and one or more coatings surrounding the core seeds, such as a drug coating, extended release coating, or seal coating, or mixtures thereof. These coatings may be applied, for example, by combining one or more of the coating components with a solvent to form a coating mixture, and applying the coating mixture to the core seeds through, for example, spraying the coating mixture on the core seeds. This may be done, for example, in a fluidized bed. The sprayed core seeds may then optionally be dried, and an additional coating be applying (for example, a drug coating followed by an extended release coating). The process parameters for applying a coating to a plurality of core seeds, such as temperature air speed, inlet air temperature, spray rate, drying time, nozzle configuration, and others would be understood by a person of skill in the art.

In some embodiments, the coated core seeds comprise a drug coating surrounding the core seeds. This drug coating may be prepared by combining one or more drug coating components (e.g., amantadine or a pharmaceutically acceptable salt thereof and one or more pharmaceutically acceptable excipients) with a solvent to produce a drug mixture, and coating a plurality of core seeds with the drug mixture. In some embodiments, using a solvent that is not an organic solvent, or that comprises, e.g., less than 1 wt % organic solvent, may result in a pharmaceutical composition with a lower level of residual organic solvent. Similarly, the seal coating, if present, may be prepared combining one or more seal coating components (such as a film-coating polymer) with a solvent to produce a seal coat mixture, and coating a plurality of core seeds with the seal coat mixture. In some embodiments, using a solvent that is not an organic solvent, or that comprises, e.g., less than 1 wt % organic solvent, may result in a pharmaceutical composition with a lower level of residual organic solvent. As discussed herein, reducing the level of organic solvent in the pharmaceutical composition compared to a composition prepared with organic solvents in the drug coating and/or seal coating steps may result in reduced gastrointestinal effects in a subject. In certain embodiments, one or more of the components is a suspension when combined with the solvent. For, example, in certain embodiments, the release modifying excipient is prepared as a suspension in water, then combined with other components and a solvent to produce the extended release coating mixture.

Thus, in some aspects, provided herein is a process of preparing an oral pharmaceutical composition comprising amantadine, or a pharmaceutically acceptable salt thereof, comprising:

a) coating a plurality of core seeds with a drug mixture to form a plurality of drug-coated core seeds; wherein the drug mixture comprises amantadine or a pharmaceutically acceptable salt thereof, one or more pharmaceutically acceptable excipients, and solvent; and wherein the drug mixture comprises less than 1 wt % organic solvent;

b) coating the plurality of drug-coated core seeds with an extended release mixture to form extended-release coated core seeds; wherein the extended release mixture comprises one or more release modifying excipients and solvent;

c) drying the plurality of extended release-coated core seeds; and d) encapsulating the plurality of extended release-coated core seeds in a capsule shell to produce the oral pharmaceutical composition; wherein the oral pharmaceutical composition comprises a core seed, a drug coating layer comprising amantadine, or a pharmaceutically acceptable salt thereof, an extended release coating layer;

and wherein the plurality of extended release-coated core seeds comprises less than 6000 ppm organic solvent.

In some embodiments, the process further comprises coating the plurality of drug-coated core seeds with a seal coat mixture prior to forming the extended release-coated core seeds; wherein the seal coat mixture comprises one or more film-forming polymers and solvent, and wherein the seal coat mixture comprises less than 1 wt % organic solvent; and wherein the oral pharmaceutical composition comprises a core seed; a drug coating layer comprising amantadine, or a pharmaceutically acceptable salt thereof, a seal coating layer, an extended release coating layer; and wherein the plurality of extended release-coated core seeds comprises less than 6000 ppm organic solvent. In some embodiments, the process includes a plurality of drying steps, for example a drying step between each coating application. In some embodiments, the pharmaceutical composition comprises less than 6000 ppm organic solvent.

The coating steps of the process, for example coating of the core seeds or the drug-core seeds, may involve applying a mixture as described herein (for example, a drug mixture, an extended release mixture, or a seal coat mixture) by any suitable means. The coating may include spraying or otherwise applying the mixture to the core seeds, or coated core seeds, such that at least a portion of the seeds are surrounded by a portion of the mixture. In some embodiments, coating a core seed (or a coated core seed) includes fully surrounding the core seed by a mixture as described herein. In other embodiments, coating the seed comprises surrounding almost all of the core seed, or the majority of the core seed, for example wherein at least 90%, at least 95%, at least 98%, at least 99%, or at least 99.9% of the surface area the core seed is surrounded by the coating. The mixture may be applied in uniform thickness, or may vary in thickness.

In some embodiments, the organic solvent is a linear or cyclic ketone (e.g., acetone, methyl ethyl ketone, etc.) In some embodiments, the organic solvent is a sulfoxide (e.g., dimethyl sulfoxide, etc.). In some embodiments, the organic solvent is an amide (e.g., dimethyl formamide, N-methyl pyrrolidone, hexamethyl phosphorous triamide (HMPT), etc.). In some embodiments, the organic solvent is a linear or cyclic ether (e.g., tetrahydrofuran, diethyl ether, bis(2-methoxyethyl) ether (diglyme), dimethoxy ethane (glyme), 1,4-dioxane, etc.). In some embodiments, the organic solvent is a phosphoramide (e.g., hexamethyl phosphoramide (HPMA), etc.). In some embodiments, the organic solvent is a chlorinated hydrocarbon (e.g., chloroform, dichloromethane, dichloroethane, carbon tetrachloride, etc.). In some embodiments, the organic solvent is a glycol (e.g., ethylene glycol, diethylene glycol, propylene glycol, etc.). In some embodiments, the organic solvent is a, nitrogen-containing solvent (e.g., pyridine, acetonitrile, etc.). In some embodiments, the organic solvent is an alcohol (e.g., a $C_1$-$C_6$ alcohol (e.g., ethanol, methanol, isopropanol, 1-butanol, 2-butanol, glycerol), such as isopropyl alcohol. In some embodiments, mixtures of two or more solvents can be used. In some embodiments, reducing or avoiding the use of organic solvent in the drug coating mixture and the optional seal coating mixture, while still using organic solvent in the extended release coating mixture can produce a pharmaceutical composition as described herein comprising a plurality of coated core seeds, for example extended-release coated core seeds as described herein, with less than 6000 ppm, less than 5500 ppm, less than 5000 ppm, less than 4500 ppm, less than 4000 ppm, less than 3500 ppm, less than 3000 ppm, less than 2500 ppm, less than 2000 ppm, less than 1500 ppm, or less than 1200 ppm organic solvent. In some embodiments of the levels of organic solvent described herein, the provided level refers to the total amount of two or more organic solvents.

The components of each coating mixture may be any of the components described herein for the coatings of the pharmaceutical composition. For example, in some embodiments, the one or more pharmaceutically acceptable excipients comprise one or more binders and one or more anti-tack agents; and the extended release mixture further comprises a plasticizer, and a pore-forming agent. In other embodiments, the drug mixture comprises hydroxypropyl methyl cellulose, copovidone, talc, and solvent; and the extended release mixture comprises ethyl cellulose, povidone, medium chain triglycerides, and solvent. In still further embodiments, the seal coat mixture comprises hydroxypropyl methyl cellulose, talc, and solvent. In some embodiments, the solvent in the seal coat mixture is water. In other embodiments, the solvent in the extended release mixture comprises alcohol and water. In still further embodiments, the solvent in the drug mixture is water.

The processes provided herein may produce an oral pharmaceutical composition comprising a plurality of coated core seeds, wherein the plurality of coated core seeds comprises less than 6000 ppm, less than 5500 ppm, less than 5000 ppm, less than 4500 ppm, less than 4000 ppm, less than 3500 ppm, less than 3000 ppm, less than 2500 ppm, less than 2000 ppm, less than 1500 ppm, or less than 1200 ppm organic solvent. In some embodiments, the coated core seeds are extended-release coated core seeds.

The process provided herein may produce a pharmaceutical composition comprising any components, in any weights, ratios, or weight percent, as described herein. For example, in some embodiments of the process provided herein, the oral pharmaceutical composition comprises:

between 30 wt % to 60 wt % amantadine, or a pharmaceutically acceptable salt thereof, between 1 wt % to 25 wt % hydroxypropyl methyl cellulose;
between 1 wt % and 4 wt % copovidone;
between 10 wt % to 20 wt % ethyl cellulose;
between 0.25 wt % to 4 wt % medium triglycerides;
between 0.25 wt % to 4 wt % povidone; and
the plurality of coated core seeds comprise less than 2000 ppm of alcohol.

In some embodiments, the pharmaceutical composition comprises less than 2000 ppm organic solvent, such as alcohol. In certain embodiments, the pharmaceutical composition comprises a plurality of coated core seeds, wherein the plurality of coated core seeds comprise less than 2000 ppm organic solvent, such as alcohol. In some embodiments of the process as provided herein, the oral pharmaceutical composition comprises core seeds comprising microcrystalline cellulose from 5 wt % to 20 wt %, or from 10 wt % to 15 wt %, or about 12.44 wt % of the composition; a drug coating surrounding each core seed, wherein the drug coating comprises amantadine, or a pharmaceutically acceptable salt thereof from 20 wt % to 60 wt %, or from 30 wt % to 50 wt %, or from 40 wt % to 50 wt %, or about 43.54 wt % of the composition; the pharmaceutically acceptable excipients hydroxypropyl methyl cellulose from 5 wt % to 18 wt %, or from 8 wt % to 15 wt %, or about 11.61 wt %, and copovidone at from 1 wt % to 5 wt %, or from 2 wt % to 4 wt %, or about 2.9 wt % of the composition; and the anti-tack agent talc at from 1 wt % to 3 wt %, or from 1.5 wt % to 2.5 wt %, or about 2.17 wt % of the composition; an extended release coating surrounding the drug coating, wherein the extended release coating comprises the release modifying excipient ethyl cellulose from 5 wt % to 25 wt %, or 10 wt % to 20 wt %, or about 15.91 wt % of the composition; the pore forming agent povidone at from 1 wt % to 3 wt %, or from 1.5 wt % go 2.5 wt %, or about 2.15 wt % of the composition; and the plasticizer medium chain triglycerides from 1 wt % to 3 wt %, or from 1.5 wt % go 2.5 wt %, or about 2.15 wt % of the composition; and a seal coating surrounding the drug coating, wherein the extended release coating surrounds the seal coating, and the seal coating comprises the film-forming polymer hydroxypropyl methyl cellulose from 3 wt % to 10 wt %, or 5 wt % to 8 wt %, or about 6.6 wt % of the composition; and the anti-tack agent talc at from 0.25 wt % to 1 wt %, or from 0.5 wt % to 0.75 wt %, or about 0.66 wt % of the composition. In some embodiment, the amantadine or a pharmaceutically acceptable salt thereof is amantadine hydrochloride. In certain embodiments, the oral pharmaceutical composition further comprises magnesium stearate from 0.01 wt % to 0.2 wt %, or 0.08 wt % to 0.12 wt %, or about 0.1 wt % of the composition. In some embodiments, the pharmaceutically acceptable salt of amantadine is amantadine hydrochloride. In another embodiment, the pharmaceutically acceptable salt of amantadine is amantadine sulfate.

In some embodiments, the plurality of core seeds surrounded by a drug coating and optionally a seal coating comprises between 70 wt % to 90 wt %, between 75 wt % to 85 wt %, or about 80.57 wt % of the final composition, and an extended release coating is applied to increase the total weight by about 24%. In other embodiments, the plurality of core seeds surrounded by a drug coating and optionally a seal coating comprises between 70 wt % to 90 wt %, between 75 wt % to 85 wt %, or about 79.92 wt % of the final composition, and an extended release coating is applied to increase the total weight by about 25%. In certain embodiments, an oral pharmaceutical composition with an increased wt % of extended release coating (for example, increased about 2 wt %, about 1.5 wt %, about 1 wt %, or about 0.5 wt %), results in a lower incidence of gastrointestinal effects compared to a composition with a lower wt % of extended release coating.

Further provided herein is an oral pharmaceutical composition formed by any of the processes described herein. Also provided herein is an oral pharmaceutical composition capable of being formed by any of the processed provided herein.

IV. Other Extended Release Dosage Forms

The person of skill in the art will recognize that other embodiments of extended release oral compositions may be envisioned, in addition to the capsule formulation described herein. Such other embodiments include extended release solid dosage forms, such as tablets, capsules, gel caps, powders, pellets, beadlets, etc. Included in such extended release compositions are those that have the release characteristics and in vivo pharmacokinetic profile to be employed in the methods of the disclosure. In some embodiments, the person skilled in the art may employ, with appropriate adjustment of design characteristics to achieve the necessary pharmacokinetic profile described herein, the extended release technology described in U.S. Pat. No. 5,358,721, to Guittard et al., or U.S. Pat. No. 6,217,905, to Edgren et al., each of which disclose an oral osmotic dosage form of amantadine, and each of which is incorporated herein by reference in its entirety. In other embodiments, the person of skill in the art may employ, again with appropriate adjustment of design characteristics, the technology described in U.S. Pat. No. 6,194,000, to Smith et al. or U.S. Patent Appl. Publication Nos. US 2006/0252788, US 2006/0189694, US 2006/0142398, US 2008/0227743, US2011/0189273 and US20150087721, all to Went et al., each of which disclose the administration of an NMDA receptor antagonist, such as amantadine, optionally in controlled release form, and each of which is incorporated herein by reference in its entirety.

Some embodiments herein provide a method of once nightly orally administering amantadine (or a pharmaceutically acceptable salt thereof, such as amantadine hydrochloride) to a subject in need thereof, said method comprising orally administering an extended release (ER) composition comprising amantadine, or a pharmaceutically acceptable salt thereof, less than four hours before bedtime (and/or after 4 p.m.). In some embodiments, administration occurs less than four hours before bedtime. In some such methods, the method increases the ON time without dyskinesia experienced by the Parkinson's disease subject. In some such methods, the method reduces the ON time with dyskinesia experienced by the Parkinson's disease subject. In some such methods, the method reduces the ON time with troublesome dyskinesia experienced by the Parkinson's disease subject. In some embodiments, the method reduces the OFF time experienced by the Parkinson's disease subject. In some embodiments, the method increases ON time without troublesome dyskinesia, and does so without inducing or increasing sleep disturbances in the Parkinson's disease subject. In some embodiments, the method improves clinician global impression, and does so without inducing or increasing sleep disturbances in the subject. In some embodiments, the composition is added to food prior to administration. In some embodiments, there is no increase in plasma concentration of amantadine for at least one hour after the administration. In some embodiments, there is no increase in plasma concentration of amantadine for at least two hours after the administration. In some embodiments, the amantadine has a single dose Tmax of 9 to 18 hours, and/or a steady state Tmax of 7 to 13 hours. In some embodiments, the amantadine has a single dose Tmax of 12 to 18 hours after administration, and/or a steady state Tmax of 8 to 12 hours. In some embodiments, the amantadine has a single dose Tmax of 12 to 16 hours after administration, and/or a steady state Tmax of 9 to 12 hours. In some embodiments, a once nightly oral administration of the composition to a human subject provides a steady state plasma concentration profile characterized by a concentration increase of amantadine of less than 25% at three hours after the administration. In some embodiments, the PK curve has a Cmax/Cmin ratio of 1.4 to 1.9. In some embodiments, the ratio of C-ave-day/C-ave night at steady state is 1.2 to 1.7. In some embodiments, the average amantadine plasma concentration during the day (C-ave-day) at steady state is 500-2000 ng/ml. In some embodiments, the amantadine is amantadine hydrochloride or amantadine sulfate. In some embodiments, the composition comprises 260 to 420 mg of amantadine hydrochloride. In some embodiments, the composition is administered as two, or three or four unit dosage forms each comprising 85 to 175 mg amantadine hydrochloride. In some embodiments, the composition is administered as two unit dosage forms each comprising 130 to 210 mg of extended release amantadine hydrochloride. In some embodiments, the composition is within a capsule of capsule size #1. In some embodiments, the composition comprises 260 mg to 340 mg of amantadine or an equivalent amount of a pharmaceutically acceptable salt thereof. In some embodiments, the composition comprises 340 mg of a pharmaceutically acceptable salt of amantadine, such as amantadine hydrochloride. In some embodiments, the composition comprises 170 mg amantadine hydrochloride. In some embodiments, oral administration of a single dose of the composition to a human subject in a fasted state provides a maximum plasma concentration (Cmax) of 1.1 to 2.1 ng/ml per mg of amantadine, and an $AUC_{0-inf}$ of 42 to 72 ng*h/mL per mg of amantadine. In some embodiments, once nightly oral administration of a dose of the composition to a human subject provides a steady state plasma concentration profile characterized by: (a) a Cmax of 2.0 to 3.1 ng/ml per mg of amantadine; (b) a Cmin of 1.3 to 2.0 ng/ml per mg of amantadine, and (c) an $AUC_{0-24}$ of 42 to 68 ng*h/mL per mg of amantadine. In some embodiments, the steady state plasma concentration profile is further characterized by: (d) no increase in plasma concentration of amantadine for at least one hour after the administration; and (e) a Cmax/Cmin ratio of 1.4 to 1.9. In some embodiments, the steady state plasma concentration profile is further characterized by: (f) no increase in concentration of amantadine for at least two hours after the administration; and (g) a Cmax/Cmin ratio of 1.4 to 1.9.

In some embodiments, the composition has an AUC profile after administration of a single dose of the composition characterized by: a fractional AUC from 0 to 4 hours that is less than 0.25% of $AUC_{0-inf}$; a fractional AUC from 0 to 8 hours that is less than 3.5% of $AUC_{0-inf}$; a fractional AUC from 0 to 12 hours that is about 5 to 12% of $AUC_{0-inf}$; a fractional AUC from 0 to 18 hours that is about 25 to 60% of $AUC_{0-inf}$; and a fractional AUC from 0 to 24 hours that is about 20 to 27% of $AUC_{0-inf}$. In some embodiments, the composition has an AUC profile after once nightly dosing of the composition at steady state conditions characterized by: a fractional AUC from 0 to 4 hours that is about 2 to 25% of $AUC_{0-24}$; a fractional AUC from 0 to 8 hours that is about 15 to 50% of $AUC_{0-24}$; a fractional AUC from 0 to 12 hours that is about 30 to 70% of $AUC_{0-24}$; and a fractional AUC from 0 to 18 hours that is about 60 to 95% of $AUC_{0-24}$. In some such embodiments, the method increases ON time without troublesome dyskinesia. In some such embodiments, the method decreases OFF time experienced by a Parkinson's subject.

Some embodiments herein provide a method of reducing sleep disturbance in a human subject undergoing treatment with amantadine, said method comprising once nightly orally administering an extended release (ER) composition comprising amantadine, or a pharmaceutically acceptable salt thereof, less than four hours before bedtime (and/or after 4 p.m.). In some such methods, the method reduces the ON time the Parkinson's disease subject experiences with dyskinesia. In some such methods, the method reduces the ON time with troublesome dyskinesia experienced by the Parkinson's disease subject. In some embodiments, the method reduces the OFF time the Parkinson's disease subject experiences. In some embodiments, the method increases ON time without troublesome dyskinesia, and does so without inducing or increasing sleep disturbances or gastrointestinal adverse events in the Parkinson's disease subject. In some embodiments, the composition is added to food prior to administration. In some embodiments, there is no increase in plasma concentration of amantadine for at least one hour after the administration. In some embodiments, the composition is added to food prior to administration. In some embodiments, there is no increase in plasma concentration of amantadine for at least one hour after the administration. In some embodiments, there is no increase in plasma concentration of amantadine for at least two hours after the administration.

In some embodiments of the methods described herein, for example methods of administration, or reducing one or more side effects, or treating one more symptoms, the unit dosage of amantadine is from 40 mg to 500 mg, 45 mg to 400 mg, from 50 mg to 350 mg, from 55 mg to 300 mg, from 60 mg to 290 mg, from 68.5 mg to 274 mg, from 50 mg to 80 mg, from 55 mg to 75 mg, from 60 mg to 70 mg, from 120 mg to 150 mg, from 135 mg to 145 mg, from 130 mg to 140 mg, from 250 mg to 300 mg, from 260 mg to 290 mg, from 270 mg to 280 mg, about 68.5 mg, about 137 mg, or about 274 mg, or an equivalent amount of a pharmaceutically acceptable salt of amantadine. In some embodiments, the pharmaceutically acceptable salt of amantadine is amantadine hydrochloride. In another embodiment, the pharmaceutically acceptable salt of amantadine is amantadine sulfate. It should be clear to one of skill in the art how to calculate an "equivalent amount" of the salt of a compound, taking into account that the salt has an increased molecular weight. For example, in some embodiments, the methods comprise administering about 68.5 mg of amantadine, or an equivalent amount of the amantadine hydrochloride salt. Thus, in some embodiments, the method comprises administering about 85 mg of amantadine hydrochloride. The unit dosage may be in a single capsule, or it may be across multiple capsules.

Pharmacokinetic parameters that are recited herein on a "per mg of drug" basis may be calculated using the mg of the form of amantadine in the composition. Thus, for example, if the composition comprises amantadine, the calculation could use the weight of amantadine present. If the composition comprises a pharmaceutically acceptable salt of amantadine, the calculation could use the weight of the pharmaceutically acceptable salt. Furthermore, a person of skill in the art know how to convert the value of a pharmacokinetic parameter that was calculated using the weight of one form (e.g., amantadine or a pharmaceutically acceptable salt of amantadine) to the value that corresponds the use of another form. Thus, for example, parameters reciting or based on the weight of amantadine could be converted to parameters reciting or based on the weight of a pharmaceutically acceptable salt of amantadine, for example amantadine hydrochloride. Examples of such parameters may include $AUC_{inf}$ with units of ng*hr/ml per mg; $pAUC_{0-6}$ with units of ng*hr/ml per mg; $pAUC_{0-8}$ with units of ng*hr/ml per mg; mean Cmax with units of ng/ml per mg; mean Cmin with units of ng/ml per mg; or mean $AUC_{0-24}$ with units of ng*h/mL per mg.

ENUMERATED EMBODIMENTS

Embodiment I-1. An oral pharmaceutical composition, comprising:
from 137 mg to 500 mg of amantadine or a pharmaceutically acceptable salt thereof, and
at least one excipient that modifies the release of said drug,
wherein said pharmaceutical composition has (i) a Tmax for amantadine of 11 to 19 hours, (ii) an $AUC_{0-inf}$ for amantadine of 44 to 72 ng*hr/ml per mg of said drug, and (iii) a $pAUC_{0-8}$ for amantadine of 1.0 to 2.0 ng*hr/ml per mg of said drug, when said pharmaceutical composition is dosed in healthy subjects of a single dose, fasting human pharmacokinetic study.

Embodiment I-2. An oral pharmaceutical composition, comprising:
from 137 mg to 500 mg of amantadine or a pharmaceutically acceptable salt thereof, and
at least one excipient that modifies the release of the amantadine or the pharmaceutically acceptable salt thereof;
wherein said pharmaceutical composition has (i) a Tmax for amantadine of 11 to 19 hours, (ii) an $AUC_{0-inf}$ for amantadine of 44 to 72 ng*hr/ml per mg of said drug, and (iii) a $pAUC_{0-6}$ for amantadine of 0.3 to 0.9 ng*hr/ml per mg of said drug, when said pharmaceutical composition is dosed in healthy subjects of a single dose, fasting human pharmacokinetic study.

Embodiment I-3. The oral pharmaceutical composition of embodiment I-1, wherein the oral pharmaceutical composition has a $pAUC_{0-6}$ for amantadine of 0.3 to 0.9 ng*hr/ml per mg of said drug when dosed in healthy subjects of a single dose, fasting human pharmacokinetic study.

Embodiment I-4. An oral pharmaceutical composition, comprising:
from 137 mg to 500 mg of amantadine or a pharmaceutically acceptable salt thereof, and
at least one excipient that modifies the release of the amantadine or the pharmaceutically acceptable salt thereof,
wherein said oral pharmaceutical composition has a dissolution profile of amantadine which shows at least 3 of (i) 0% to 10% in 2 hours, (ii) 3% to 14% in 4 hours, (iii) 23% to 40% in 6 hours, (iv) 50% to 70% in 8 hours, and (v) not less than 80% in 12 hours as determined in a USP Type 2 apparatus (paddles) at 50 rpm at 37.0±0.5° C. with 500 ml water as the dissolution medium, and
wherein said oral pharmaceutical composition has (i) a Tmax for amantadine of 11 to 19 hours, and (ii) an $AUC_{0-inf}$ for amantadine of 44 to 72 ng*hr/ml per mg of said drug, when said oral pharmaceutical composition is dosed in healthy subjects of a single dose, fasting human pharmacokinetic study.

Embodiment I-5. The oral pharmaceutical composition of embodiment I-4, wherein said dissolution profile is (i)

0% to 9% in 2 hours, (ii) 3% to 14% in 4 hours, (iii) 24% to 40% in 6 hours, (iv) 45% to 70% in 8 hours, and (v) not less than 82% in 12 hours.

Embodiment I-6. A method for administering an oral pharmaceutical composition to a subject in need thereof, comprising:
orally administering to said patient once daily, 0 to 4 hours before bedtime, an oral pharmaceutical composition,
wherein the oral pharmaceutical composition comprises from 137 mg to 500 mg of amantadine or a pharmaceutically acceptable salt thereof, and
at least one excipient that modifies the release of the amantadine or pharmaceutically acceptable salt thereof, and
wherein said oral pharmaceutical composition has (i) a Tmax for amantadine of 11 to 19 hours, (ii) an $AUC_{0-inf}$ for amantadine of 44 to 72 ng*hr/ml per mg of said drug, and (iii) a $pAUC_{0-8}$ for amantadine of 1.0 to 2.0 ng*hr/ml per mg of said drug, when said pharmaceutical composition is dosed in healthy subjects of a single dose, fasting human pharmacokinetic study.

Embodiment I-7. A method for administering an oral an oral pharmaceutical composition to a subject in need thereof, comprising:
orally administering to a subject once daily, 0 to 4 hours before bedtime, a pharmaceutical composition,
wherein the oral pharmaceutical composition comprises from 137 mg to 500 mg of amantadine or a pharmaceutically acceptable salt thereof, and
at least one excipient that modifies the release of the amantadine or the pharmaceutically acceptable salt thereof, and
wherein said oral pharmaceutical composition has (i) a Tmax for amantadine of 11 to 19 hours, (ii) an $AUC_{0-inf}$ for amantadine of 44 to 72 ng*hr/ml per mg of said drug, and (iii) a $pAUC_{0-6}$ for amantadine of 0.3 to 0.9 ng*hr/ml per mg of said drug, when said oral pharmaceutical composition is dosed in healthy subjects of a single dose, fasting human pharmacokinetic study.

Embodiment I-8. The method of embodiment I-6, wherein the oral pharmaceutical composition has a $pAUC_{0-6}$ for amantadine of 0.3 to 0.9 ng*hr/ml per mg of said drug when dosed in healthy subjects of a single dose, fasting human pharmacokinetic study.

Embodiment I-9. A method for administering an oral pharmaceutical composition to a subject in need thereof, comprising:
orally administering to a subject once daily, 0 to 4 hours before bedtime, a oral pharmaceutical composition,
wherein the oral pharmaceutical composition comprises from 137 mg to 500 mg amantadine or a pharmaceutically acceptable salt thereof, and
at least one excipient that modifies the release of the amantadine or the pharmaceutically acceptable salt thereof;
wherein the oral pharmaceutical composition has a dissolution profile of amantadine which shows at least 3 of (i) 0% to 10% in 2 hours, (ii) 3% to 14% in 4 hours, (iii) 23% to 40% in 6 hours, (iv) 50% to 70% in 8 hours, and (v) not less than 80% in 12 hours as determined in a USP Type 2 apparatus (paddles) at 50 rpm at 37.0±0.5° C. with 500 ml water as the dissolution medium, and
wherein the oral pharmaceutical composition has a Tmax for amantadine of 11 to 19 hours, and (ii) an $AUC_{0-inf}$ for amantadine of 44 to 72 ng*hr/ml per mg of said drug, when said oral pharmaceutical composition is dosed in healthy subjects of a single dose, fasting human pharmacokinetic study.

Embodiment I-10. The method of embodiment I-9, wherein said dissolution profile is (i) 0% to 9% in 2 hours, (ii) 3% to 14% in 4 hours, (iii) 24% to 40% in 6 hours, (iv) 45% to 70% in 8 hours, and (v) not less than 82% in 12 hours.

Embodiment I-11. A method for reducing gastrointestinal adverse events in a subject orally administered a pharmaceutical composition comprising amantadine or a pharmaceutically acceptable salt thereof, comprising:
orally administering to a subject an oral pharmaceutical composition comprising from 137 mg to 500 mg of amantadine or a pharmaceutically acceptable salt thereof, and
at least one excipient that modifies the release of the amantadine or the pharmaceutically acceptable salt thereof,
wherein the oral pharmaceutical composition has (i) a Tmax for amantadine of 11 to 19 hours, (ii) an $AUC_{0-inf}$ for amantadine of 44 to 72 ng*hr/ml per mg of said drug, and (iii) a $pAUC_{0-8}$ for amantadine of 1.0 to 2.0 ng*hr/ml per mg of said drug, when the oral pharmaceutical composition is dosed in healthy subjects of a single dose, fasting human pharmacokinetic study.

Embodiment I-12. A method for reducing gastrointestinal adverse events in a subject orally administered an oral pharmaceutical composition comprising amantadine or a pharmaceutically acceptable salt thereof, comprising:
orally administering to a subject an oral pharmaceutical composition comprising from 137 mg to 500 mg of amantadine or a pharmaceutically acceptable salt thereof, and
at least one excipient that modifies the release of the amantadine or the pharmaceutically acceptable salt thereof,
wherein the oral pharmaceutical composition has (i) a Tmax for amantadine of 11 to 19 hours, (ii) an $AUC_{0-inf}$ for amantadine of 44 to 72 ng*hr/ml per mg of said drug, and (iii) a $pAUC_{0-6}$ for amantadine of 0.3 to 0.9 ng*hr/ml per mg of said drug, when the oral pharmaceutical composition is dosed in healthy subjects of a single dose, fasting human pharmacokinetic study.

Embodiment I-13. The method of embodiment I-11, wherein the oral pharmaceutical composition has a $pAUC_{0-6}$ for amantadine of 0.3 to 0.9 ng*hr/ml per mg of said drug when dosed in healthy subjects of a single dose, fasting human pharmacokinetic study.

Embodiment I-14. A method for reducing gastrointestinal adverse events in a subject orally administered a pharmaceutical composition comprising amantadine or a pharmaceutically acceptable salt thereof, comprising:
orally administering to a subject an oral pharmaceutical composition comprising from 137 mg to 500 mg of amantadine or a pharmaceutically acceptable salt thereof, and
at least one excipient that modifies the release of the amantadine or the pharmaceutically acceptable salt thereof,
wherein the oral pharmaceutical composition has a dissolution profile of amantadine which shows at least 3 of (i) 0% to 10% in 2 hours, (ii) 3% to 14% in 4 hours, (iii) 23% to 40% in 6 hours, (iv) 50% to 70% in 8 hours, and (v) not less than 80% in 12 hours as determined in a USP Type 2 apparatus (paddles) at 50 rpm at 37.0±0.5° C. with 500 ml water as the dissolution medium, and wherein said oral pharmaceutical composition has (i) a Tmax for amantadine of 11 to 19 hours, and (ii) an $AUC_{0\text{-}inf}$ for amantadine of 44 to 72 ng*hr/ml per mg of said drug, when said pharmaceutical composition is dosed in healthy subjects of a single dose, fasting human pharmacokinetic study.

Embodiment I-15. The method of embodiment I-14, wherein said dissolution profile is (i) 0% to 9% in 2 hours, (ii) 3% to 14% in 4 hours, (iii) 24% to 40% in 6 hours, (iv) 45% to 70% in 8 hours, and (v) not less than 82% in 12 hours.

Embodiment I-16. A process of preparing an oral pharmaceutical composition comprising amantadine, or a pharmaceutically acceptable salt thereof, comprising:

a) coating a plurality of core seeds with a drug mixture to form a drug-coated core seed,
 wherein the drug mixture comprises amantadine or a pharmaceutically acceptable salt thereof, one or more pharmaceutically acceptable excipients, and solvent, and
 wherein the drug mixture comprises less than 1 wt % organic solvent;

b) coating the plurality of drug-coated core seeds with an extended release mixture to form extended-release coated core seeds,
 wherein the extended release mixture comprises one or more release modifying excipients and solvent;

c) drying the plurality of extended release-coated core seeds; and d) encapsulating the plurality of extended release-coated core seeds in a capsule shell to produce the oral pharmaceutical composition,
 wherein the oral pharmaceutical composition comprises a core seed, a drug
 coating comprising amantadine, or a pharmaceutically acceptable salt thereof, an extended release coating, and
 the plurality of extended release-coated core seeds comprise less than 6000 ppm organic solvent.

Embodiment I-17. The process of embodiment I-16, further comprising:
coating the plurality of drug-coated core seeds with a seal coat mixture prior to forming the extended release-coated core seeds,
wherein the seal coat mixture comprises one or more film-forming polymers and solvent, and
wherein the seal coat mixture comprises less than 1 wt % organic solvent; and
 wherein the oral pharmaceutical composition comprises a core seed; a drug coating comprising amantadine, or a pharmaceutically acceptable salt thereof, a seal coating, an extended release coating;
 the plurality of extended release-coated core seeds comprise less than 6000 ppm organic solvent.

Embodiment I-18. The process of embodiment I-16 or I-17, wherein the organic solvent is an alcohol.

Embodiment I-19. The process of any one of embodiments I-16 to I-18, wherein the organic solvent is isopropyl alcohol.

Embodiment I-20. The process of any one of embodiments I-16 to I-19, wherein the one or more pharmaceutically acceptable excipients comprise one or more binders and one or more anti-tack agents; and the extended release mixture further comprises a plasticizer and a pore-forming agent.

Embodiment I-21. The process of any one of embodiments I-16 to I-20, wherein the drug mixture comprises hydroxpropyl methyl cellulose, copovidone, talc, and solvent; and the extended release mixture comprises ethyl cellulose, povidone, medium chain triglycerides, and solvent.

Embodiment I-22. The process of any one of embodiments I-17 to I-21, wherein the seal coat mixture comprises hydroxypropyl methyl cellulose, talc, and solvent.

Embodiment I-23. The process of any one of embodiments I-16 to I-22, wherein the plurality of extended-release coated core seeds comprises less than 2000 ppm of organic solvent.

Embodiment I-24. The process of any one of embodiments I-16 to I-23, wherein the oral pharmaceutical composition comprises:
between 30 wt % to 60 wt % amantadine, or a pharmaceutically acceptable salt thereof,
between 1 wt % to 25 wt % hydroxypropyl methyl cellulose;
between 1 wt % and 4 wt % copovidone;
between 10 wt % to 20 wt % ethyl cellulose;
between 0.25 wt % to 4 wt % medium triglycerides;
between 0.25 wt % to 4 wt % povidone; and
wherein the plurality extended-release coated core seeds comprises than 2000 ppm of alcohol.

Embodiment I-25. The process of any one of embodiments I-16 to I-24, wherein the solvent in the drug mixture comprises water.

Embodiment I-26. The process of embodiment I-25, wherein the solvent in the drug mixture comprises greater than 99 wt % water.

Embodiment I-27. The process of embodiment I-25 or claim I-26, wherein the solvent in the drug mixture is water.

Embodiment I-28. The process of any one of embodiments I-17 to I-27, wherein the solvent in the seal coat mixture comprises water.

Embodiment I-29. The process of embodiment I-28, wherein the solvent in the seal mixture comprises greater than 99 wt % water.

Embodiment I-30. The process of embodiment I-28 or I-29, wherein the solvent in the seal mixture is water.

Embodiment I-31. The process of any one of embodiments I-16 to I-30, wherein the solvent in the extended release mixture comprises water.

Embodiment I-32. The process of any one of embodiments I-16 to I-30, wherein the solvent in the extended release mixture comprises an organic solvent.

Embodiment I-33. The process of any one of embodiments I-16 to I-32, wherein the solvent in the extended release mixture comprises water and an organic solvent.

Embodiment I-34. The process of embodiment I-33, wherein the solvent in the extended release mixture comprises water and up to 50 wt % of an organic solvent.

Embodiment I-35. An oral pharmaceutical composition formed by the process of any one of embodiments I-16 to I-34.

Embodiment I-36. An oral pharmaceutical composition capable of being formed by the process of any one of embodiments I-16 to I-35.

Embodiment I-37. An oral pharmaceutical composition comprising amantadine, or a pharmaceutically acceptable salt thereof, comprising:
a plurality of coated core seeds, wherein each coated core seed comprises:

a core seed,
a drug coating surrounding the core seed, wherein the drug coating comprises amantadine, or a pharmaceutically acceptable salt thereof and one or more pharmaceutically acceptable excipients; and an extended release coating surrounding the drug coating, wherein the extended release coating comprises one or more release modifying excipients; and
a capsule shell, wherein the plurality of coated core seeds is encapsulated within the capsule shell; and,
wherein the plurality of coated core seeds comprises less than 6000 ppm organic solvent.

Embodiment I-38. The oral pharmaceutical composition of embodiment I-37, wherein the organic solvent is an alcohol.

Embodiment I-39. The oral pharmaceutical composition of embodiment I-37 or I-38, wherein the organic solvent is isopropyl alcohol.

Embodiment I-40. The oral pharmaceutical composition of any one of embodiments I-37 to I-39, further comprising a seal coating surrounding the drug coating, wherein the seal coating comprises one or more film-forming polymers and is surrounded by the extended release coating.

Embodiment I-41. The oral pharmaceutical composition of any one of embodiments I-37 to I-40, wherein the one or more pharmaceutically acceptable excipients comprise one or more binders and one or more anti-tack agents, and the extended release coating further comprises a plasticizer and a pore-forming agent.

Embodiment I-42. The oral pharmaceutical composition of any one of embodiments I-37 to I-41, wherein:
the one or more pharmaceutically acceptable excipients comprise one or more binders and one or more anti-tack agents, wherein the one or more binders comprise hydroxpropyl methyl cellulose and copovidone, and the one or more anti-tack agents comprise talc; and
the extended release coating comprises a release modifying excipient, a plasticizer, a pore-forming agent,
  wherein the release modifying excipient comprises ethyl cellulose, the pore forming agent comprises povidone, and the plasticizer comprises medium chain triglycerides.

Embodiment I-43. The oral pharmaceutical composition of any one of embodiments I-40 to I-42, wherein the film-forming polymer comprises hydroxypropyl methyl cellulose, and the seal coating further comprises talc.

Embodiment I-44. The oral pharmaceutical composition of any one of embodiments I-37 to I-43, wherein plurality of coated core seeds comprise less than 2000 ppm of organic solvent.

Embodiment I-45. The oral pharmaceutical composition of any one of embodiments I-37 to I-44, wherein the pharmaceutical composition comprises:
between 30 wt % to 60 wt % amantadine or a pharmaceutically acceptable salt thereof;
between 1 wt % to 25 wt % hydroxypropyl methyl cellulose;
between 1 wt % and 4 wt % copovidone;
between 10 wt % to 20 wt % ethyl cellulose;
between 0.25 wt % to 4 wt % medium triglycerides;
between 0.25 wt % to 4 wt % povidone; and the plurality of coated core seeds comprises than 2000 ppm of alcohol.

Embodiment I-46. The oral pharmaceutical composition of any one of embodiments I-37 to I-45, wherein:
the drug coating comprises:
between 40 wt % to 50 wt % of amantadine or a pharmaceutically acceptable salt thereof;
between 10 wt % to 15 wt % of hydroxypropyl methyl cellulose;
between 2 wt % to 3.5 wt % of copovidone; and
between 1.8 wt % to 2.5 wt % of talc; and
the extended release coating comprises:
between 10 wt % to 20 wt % of ethyl cellulose;
between 1.5 wt % to 2.5 wt % povidone; and
between 1.5 wt % to 2.5 wt % medium chain triglycerides.

Embodiment I-47. The oral pharmaceutical composition of any one of embodiments I-37 to I-46, wherein the seal coating comprises between 5 wt % to 10 wt % hydroxypropyl methyl cellulose and between 0.25 wt % to 1 wt % talc.

Embodiment I-48. The oral pharmaceutical composition of any one of embodiments I-37 to I-47, wherein the unit dose of amantadine is between 40 mg to 500 mg, or an equivalent amount of a pharmaceutically acceptable salt thereof.

Embodiment I-49. The oral pharmaceutical composition of any one of embodiments I-37 to I-48, wherein the unit dose of amantadine is between 60 mg to 300 mg, or an equivalent amount of a pharmaceutically acceptable salt thereof.

Embodiment I-50. The oral pharmaceutical composition of any one of embodiments I-37 to I-49, wherein the oral pharmaceutical composition is formulated for once-daily administration.

Embodiment II-1. An oral pharmaceutical composition, comprising:
a drug, wherein the drug is amantadine or a pharmaceutically acceptable salt thereof, and wherein said oral pharmaceutical composition comprises from 50 mg to 500 mg of the amantadine or an equivalent amount of the pharmaceutically acceptable salt thereof; and
at least one excipient that modifies the release of at least a portion of said drug;
wherein said oral pharmaceutical composition has a dissolution profile of said drug which shows at least four of:
(i) 0% to 10% in 2 hours,
(ii) 3% to 14% in 4 hours,
(iii) 23% to 40% in 6 hours,
(iv) 50% to 70% in 8 hours, and
(v) not less than 80% in 12 hours;
  wherein the dissolution profile is determined with a USP Type 2 apparatus (paddles) at 50 rpm at 37.0±0.5° C. with 500 ml water as the dissolution medium; and
wherein said oral pharmaceutical composition provides (i) a Tmax for amantadine of 11 to 19 hours, and (ii) an $AUC_{0\text{-}inf}$ for amantadine of 44 to 72 ng*hr/ml per mg of said drug, when said oral pharmaceutical composition is dosed in healthy subjects of a single dose, human pharmacokinetic study, wherein the subjects are dosed in the morning after an overnight fast.

Embodiment II-2. The oral pharmaceutical composition of embodiment 11-1, wherein said dissolution profile is (i) 0% to 9% in 2 hours, (ii) 3% to 14% in 4 hours, (iii) 24% to 40% in 6 hours, (iv) 45% to 70% in 8 hours, and (v) not less than 82% in 12 hours.

Embodiment II-3. An oral pharmaceutical composition, comprising:
a drug, wherein the drug is amantadine or a pharmaceutically acceptable salt thereof, and wherein said oral pharmaceutical composition comprises from 50 mg to 500 mg of the amantadine or an equivalent amount of the pharmaceutically acceptable salt thereof; and at least one excipient that modifies the release of at least a portion of said drug;

wherein said oral pharmaceutical composition has a dissolution profile of said drug which shows at least four of:
(i) not more than 10% dissolution at 2 hours;
(ii) 5% to 13% dissolution at 4 hours;
(iii) 20% to 43% dissolution at 6 hours;
(iv) 50% to 70% dissolution at 8 hours; and
(v) at least 80% dissolution at 12 hours;

wherein the dissolution profile is determined with a USP Type 2 apparatus (paddles) at 50 rpm at 37.0±0.5° C. with 500 ml water as the dissolution medium; and wherein said oral pharmaceutical composition provides (i) a Tmax for amantadine of 11 to 19 hours, and (ii) an $AUC_{0-inf}$ for amantadine of 44 to 72 ng*hr/ml per mg of said drug, when said oral pharmaceutical composition is dosed in healthy subjects of a single dose, human pharmacokinetic study, wherein the subjects are dosed in the morning after an overnight fast.

Embodiment II-4. An oral pharmaceutical composition, comprising:

a drug, wherein the drug is amantadine or a pharmaceutically acceptable salt thereof, and wherein said oral pharmaceutical composition comprises from 50 mg to 500 mg of the amantadine or an equivalent amount of the pharmaceutically acceptable salt thereof; and at least one excipient that modifies the release of at least a portion of said drug;

wherein said oral pharmaceutical composition has a dissolution profile of said drug which shows at least four of:
(i) not more than 9% dissolution at 2 hours,
(ii) 3% to 14% dissolution at 4 hours,
(iii) 20% to 43% dissolution at 6 hours,
(iv) 45% to 70% dissolution at 8 hours; and
(v) at least 82% dissolution at 12 hours, using a USP Apparatus II (Paddles) at 50 rpm with 500 ml water at 37.0±0.5° C. as the dissolution medium;

wherein the dissolution profile is determined with a USP Type 2 apparatus (paddles) at 50 rpm at 37.0±0.5° C. with 500 ml water as the dissolution medium; and wherein said oral pharmaceutical composition provides (i) a Tmax for amantadine of 11 to 19 hours, and (ii) an $AUC_{0-inf}$ for amantadine of 44 to 72 ng*hr/ml per mg of said drug, when said oral pharmaceutical composition is dosed in healthy subjects of a single dose, human pharmacokinetic study, wherein the subjects are dosed in the morning after an overnight fast.

Embodiment II-5. The oral pharmaceutical composition of any one of embodiments II-1 to II-4, wherein the Tmax for amantadine is 12 to 18 hours.

Embodiment II-6. The oral pharmaceutical composition of any one of embodiments II-1 to II-5, wherein the oral pharmaceutical composition shows each of (i) to (v).

Embodiment II-7. The oral pharmaceutical composition of any one of embodiments II-1 to II-6, wherein the oral pharmaceutical composition has a dissolution of 9% at 4 hours.

Embodiment II-8. The oral pharmaceutical composition of any one of embodiments II-1 to II-7, wherein the oral pharmaceutical composition has a dissolution of 31% at 6 hours.

Embodiment II-9. The oral pharmaceutical composition of any one of embodiments II-1 to II-8, wherein the oral pharmaceutical composition has a dissolution of 61% at 8 hours.

Embodiment II-10. The oral pharmaceutical composition of any one of embodiments II-1 to II-9, wherein the oral pharmaceutical composition has a dissolution of 94% at 12 hours.

Embodiment II-11. An oral pharmaceutical composition, comprising:

a drug, wherein the drug is amantadine or a pharmaceutically acceptable salt thereof, and wherein said oral pharmaceutical composition comprises from 50 mg to 500 mg of the amantadine or an equivalent amount of the pharmaceutically acceptable salt thereof; and at least one excipient that modifies the release of at least a portion of said drug;

wherein when dosed to healthy subjects of a single dose, human pharmacokinetic study, wherein the subjects are dosed in the morning after an overnight fast, said oral pharmaceutical composition provides:

a Tmax for amantadine of 11 to 19 hours;

an $AUC_{0-inf}$ for amantadine of 44 to 72 ng*hr/ml per mg of said drug; and a $pAUC_{0-8}$ for amantadine of 1.0 to 2.0 ng*hr/ml per mg of said drug.

Embodiment II-12. The oral pharmaceutical composition of embodiment II-11, wherein the oral pharmaceutical composition provides a $pAUC_{0-6}$ for amantadine that is 0.3 to 0.9 ng*hr/ml per mg of said drug when dosed to healthy subjects of a single dose, human pharmacokinetic study, wherein the subjects are dosed in the morning after an overnight fast.

Embodiment II-13. An oral pharmaceutical composition, comprising:

a drug, wherein the drug is amantadine or a pharmaceutically acceptable salt thereof, and wherein said oral pharmaceutical composition comprises from 50 mg to 500 mg of the amantadine or an equivalent amount of the pharmaceutically acceptable salt thereof; and at least one excipient that modifies the release of at least a portion of said drug;

wherein when dosed to healthy subjects of a single dose, human pharmacokinetic study, wherein the subjects are dosed in the morning after an overnight fast, said oral pharmaceutical composition provides:
(i) a fractional AUC from 0 to 4 hours that is less than 1% of $AUC_{0-inf}$;
(ii) a fractional AUC from 0 to 8 hours that is not more than 4.5% of $AUC_{0-inf}$;
(iii) a fractional AUC from 0 to 12 hours that is about 5% to 15% of $AUC_{0-inf}$;
(iv) a fractional AUC from 0 to 18 hours that is about 20% to 35% of $AUC_{0-inf}$;
(v) and a fractional AUC from 0 to 24 hours that is about 34% to 48% of $AUC_{0-inf}$.

Embodiment II-14. The oral pharmaceutical composition of embodiment II-13, wherein the fractional AUC from 0 to 4 is less than 0.2% of $AUC_{0-inf}$.

Embodiment II-15. The oral pharmaceutical composition of embodiment II-13 or II-14, wherein the fractional AUC from 0 to 8 hours is 1.0% to 4.0% of $AUC_{0-inf}$.

Embodiment II-16. The oral pharmaceutical composition of any one of embodiments II-13 to II-15, wherein the fractional AUC from 0 to 8 hours is 1.5% to 3.75% of $AUC_{0-inf}$.

Embodiment II-17. The oral pharmaceutical composition of any one of embodiments II-13 to II-16, wherein the fractional AUC from 0 to 8 hours is 1.75% to 3.5% of $AUC_{0-inf}$.

Embodiment II-18. The oral pharmaceutical composition of any one of embodiments II-13 to II-17, wherein the fractional AUC from 0 to 12 hours that is about 7.0% to 12.0% of $AUC_{0-inf}$.

Embodiment II-19. The oral pharmaceutical composition of any one of embodiments II-13 to 11-18, wherein the fractional AUC from 0 to 18 hours is about 22.5% to 27.5% of $AUC_{0-inf}$.

Embodiment II-20. An oral pharmaceutical composition, comprising:

a drug, wherein the drug is amantadine or a pharmaceutically acceptable salt thereof, and wherein said oral pharmaceutical composition comprises from 50 mg to 500 mg of the amantadine or an equivalent amount of the pharmaceutically acceptable salt thereof; and at least one excipient that modifies the release of at least a portion of said drug;

wherein when dosed to healthy subjects of a single dose, human pharmacokinetic study, wherein the subjects are dosed in the morning after an overnight fast, said oral pharmaceutical composition provides:

a fractional AUC from 0 to 4 hours that is less than 0.25% of $AUC_{0-inf}$;

a fractional AUC from 0 to 8 hours that is less than 3.5% of $AUC_{0-inf}$;

a fractional AUC from 0 to 12 hours that is about 5 to 12% of $AUC_{0-inf}$; and a fractional AUC from 0 to 18 hours that is about 25 to 60% of $AUC_{0-inf}$.

Embodiment II-21. The oral pharmaceutical composition of any one of embodiments II-1 to II-20, comprising from 100 mg to 450 mg of amantadine, or an equivalent amount of a pharmaceutically acceptable salt thereof.

Embodiment II-22. The oral pharmaceutical composition of any one of embodiments II-1 to II-21, comprising from 120 mg to 150 mg of amantadine, or an equivalent amount of a pharmaceutically acceptable salt thereof.

Embodiment II-23. The oral pharmaceutical composition of any one of embodiments II-1 to II-22, comprising 137 mg of amantadine, or an equivalent amount of a pharmaceutically acceptable salt thereof.

Embodiment II-24. The oral pharmaceutical composition of any one of embodiments II-1 to II-21, comprising from 260 mg to 305 mg of amantadine, or an equivalent amount of a pharmaceutically acceptable salt thereof.

Embodiment II-25. The oral pharmaceutical composition of any one of embodiments II-1 to II-21, or II-24, comprising 274 mg of amantadine, or an equivalent amount of a pharmaceutically acceptable salt thereof.

Embodiment II-26. The oral pharmaceutical composition of any one of embodiments II-1 to II-25, comprising one, two, three, or four unit dosage forms.

Embodiment II-27. The oral pharmaceutical composition of any one of embodiments II-1 to II-26, comprising one or two unit dosage forms.

Embodiment II-28. The oral pharmaceutical composition of any one of embodiments II-1 to II-27, wherein the drug is a pharmaceutically acceptable salt of amantadine.

Embodiment II-29. The oral pharmaceutical composition of any one of embodiments II-1 to II-28, wherein the drug is amantadine hydrochloride.

Embodiment II-30. The oral pharmaceutical composition of any one of embodiments II-1 to II-29, comprising less than 6000 ppm of organic solvent.

Embodiment II-31. The oral pharmaceutical composition of any one of embodiments II-1 to II-30, comprising less than 2000 ppm of organic solvent.

Embodiment II-32. The oral pharmaceutical composition of any one of embodiments II-1 to II-31, comprising:

a plurality of coated core seeds, wherein each coated core seed comprises:

a core seed;

a drug coating surrounding the core seed, wherein the drug coating comprises amantadine or a pharmaceutically acceptable salt thereof and one or more pharmaceutically acceptable excipients;

an extended release coating surrounding the drug coating, wherein the extended release coating comprises one or more release modifying excipients; and a capsule shell, wherein the plurality of coated core seeds is encapsulated within the capsule shell.

Embodiment II-33. The oral pharmaceutical composition of embodiment II-32, wherein the plurality of coated core seeds comprises less than 6000 ppm organic solvent.

Embodiment II-34. The oral pharmaceutical composition of embodiment II-32, wherein the plurality of coated core seeds comprises less than 2000 ppm organic solvent.

Embodiment II-35. A method of reducing levodopa-induced dyskinesia (LID) in a subject with Parkinson's disease in need thereof, comprising orally administering once daily to the subject an oral pharmaceutical composition according to any one of embodiments II-1 to II-34, wherein LID is reduced in the subject.

Embodiment II-36. The method of embodiment II-35, wherein reducing LID comprises reducing the severity of dyskinesia.

Embodiment II-37. The method of embodiment II-35 or II-36, wherein the reduction of LID is evaluated with the Unified Dyskinesia Rating Scale (UDysRS).

Embodiment II-38. A method of increasing ON time without troublesome dyskinesia in a subject with Parkinson's disease in need thereof, wherein the subject has levodopa-induced dyskinesia (LID), the method comprising orally administering once daily to the subject an oral pharmaceutical composition according to any one of embodiments II-1 to II-34.

Embodiment II-39. The method of embodiment II-38, wherein the increase in ON time without troublesome dyskinesia is determined in a placebo controlled, double blind clinical study.

Embodiment II-40. A method of reducing OFF time in a subject with Parkinson's disease in need thereof, wherein the subject has levodopa-induced dyskinesia (LID), the method comprising orally administering once daily to the subject an oral pharmaceutical composition according to any one of embodiments II-1 to II-34, wherein OFF time is reduced in the subject.

Embodiment II-41. The method of embodiment II-40, wherein the increase in OFF time is determined in a placebo controlled, double blind clinical study.

Embodiment II-42. A method of treating a hypokinetic disorder in a subject with Multiple Sclerosis in need thereof, comprising orally administering once daily to the subject an oral pharmaceutical composition according to any one of embodiments II-1 to II-34.

Embodiment II-43. The method of embodiment II-42, wherein the hypokinetic disorder is walking impairment.

Embodiment II-44. The method of any one of embodiments II-35 to II-43, wherein the oral pharmaceutical composition is administered to the subject once nightly.

Embodiment II-45. The method of any one of embodiments II-35 to II-44, wherein the oral pharmaceutical composition is administered to the subject 0 to 4 hours before bedtime.

Embodiment II-46. The method of any one of embodiments II-35 to II-45, wherein the daily dose administered to the subject is 100 mg to 450 mg of amantadine, or an equivalent amount of a pharmaceutically acceptable salt thereof.

Embodiment II-47. The method of any one of embodiments II-35 to II-46, wherein the once daily dose administered to the subject is 120 mg to 150 mg of amantadine, or an equivalent amount of a pharmaceutically acceptable salt thereof.

Embodiment II-48. The method of any one of embodiments II-35 to II-47, wherein the once daily dose administered to the subject is 137 mg of amantadine, or an equivalent amount of a pharmaceutically acceptable salt thereof.

Embodiment II-49. The method of any one of embodiments II-35 to II-46, wherein the once daily dose administered to the subject is 260 mg to 305 mg of amantadine, or an equivalent amount of a pharmaceutically acceptable salt thereof.

Embodiment II-50. The method of any one of embodiments II-35 to II-46, or II-49, wherein the once daily dose administered to the subject is 274 mg of amantadine, or an equivalent amount of a pharmaceutically acceptable salt thereof.

Embodiment II-51. The method of any one of embodiments II-35 to II-50, wherein the oral pharmaceutical composition is administered as one, two, three, or four unit dosage forms.

Embodiment II-52. The method of any one of embodiments II-35 to II-51, wherein the oral pharmaceutical composition is administered as one or two unit dosage forms.

Embodiment II-53. The method of any one of embodiments II-35 to II-52, wherein the oral pharmaceutical composition is administered as two or three unit dosage forms each comprising 68.5 to 175 mg amantadine, or an equivalent amount of a pharmaceutically acceptable salt thereof.

Embodiment II-54. The method of any one of embodiments II-35 to II-52, wherein the drug is a pharmaceutically acceptable salt of amantadine.

Embodiment II-55. The method of any one of embodiments II-35 to II-53, wherein the drug is amantadine hydrochloride.

Embodiment II-56. An oral pharmaceutical composition according to any one of embodiments II-1 to II-34 for use in a method of reducing levodopa-induced dyskinesia (LID) in a subject with Parkinson's disease in need thereof, wherein the method comprises orally administering once daily to the subject the oral pharmaceutical composition.

Embodiment II-57. The oral pharmaceutical composition for use of embodiment II-56, wherein reducing LID comprises reducing the severity of dyskinesia.

Embodiment II-58. The oral pharmaceutical composition for use of embodiment II-56 or II-57, wherein the reduction of LID is evaluated with the Unified Dyskinesia Rating Scale (UDysRS).

Embodiment II-59. An oral pharmaceutical composition according to any one of embodiments II-1 to II-34 for use in a method of increasing ON time without troublesome dyskinesia in a subject with Parkinson's disease in need thereof, wherein the subject has levodopa-induced dyskinesia (LID), the method comprising orally administering once daily to the subject the oral pharmaceutical composition.

Embodiment II-60. The oral pharmaceutical composition for use of embodiment II-59, wherein the increase in ON time without troublesome dyskinesia is determined in a placebo controlled, double blind clinical study.

Embodiment II-61. An oral pharmaceutical composition according to any one of embodiments II-1 to II-34 for use in a method of reducing OFF time in a subject with Parkinson's disease in need thereof, wherein the subject has levodopa-induced dyskinesia (LID), the method comprising orally administering once daily to the subject the oral pharmaceutical composition.

Embodiment II-62. The oral pharmaceutical composition for use of embodiment II-61, wherein the increase in OFF time is determined in a placebo controlled, double blind clinical study.

Embodiment II-63. An oral pharmaceutical composition according to any one of embodiments II-1 to II-34 for use in a method of treating a hypokinetic disorder in a subject with Multiple Sclerosis in need thereof, the method comprising orally administering once daily to the subject the oral pharmaceutical composition.

Embodiment II-64. The oral pharmaceutical composition for use of embodiment II-63, wherein the hypokinetic disorder is walking impairment.

Embodiment II-65. The oral pharmaceutical composition for use of any one of embodiments II-56 to II-64, wherein the oral pharmaceutical composition is administered to the subject once nightly.

Embodiment II-66. The oral pharmaceutical composition for use of any one of embodiments II-56 to II-65, wherein the oral pharmaceutical composition is administered to the subject 0 to 4 hours before bedtime.

Embodiment II-67. The oral pharmaceutical composition for use of any one of embodiments II-56 to II-66, wherein the daily dose administered to the subject is 100 mg to 450 mg of amantadine, or an equivalent amount of a pharmaceutically acceptable salt thereof.

Embodiment II-68. The oral pharmaceutical composition for use of any one of embodiments II-56 to II-67, wherein the once daily dose administered to the subject is 120 mg to 150 mg of amantadine, or an equivalent amount of a pharmaceutically acceptable salt thereof.

Embodiment II-69. The oral pharmaceutical composition for use of any one of embodiments II-56 to II-68, wherein the once daily dose administered to the subject is 137 mg of amantadine, or an equivalent amount of a pharmaceutically acceptable salt thereof.

Embodiment II-70. The oral pharmaceutical composition for use of any one of embodiments II-56 to II-67, wherein the once daily dose administered to the subject is 260 mg to 305 mg of amantadine, or an equivalent amount of a pharmaceutically acceptable salt thereof.

Embodiment II-71. The oral pharmaceutical composition for use of any one of embodiments II-56 to II-67, or II-70, wherein the once daily dose administered to the subject is 274 mg of amantadine, or an equivalent amount of a pharmaceutically acceptable salt thereof.

Embodiment II-72. The oral pharmaceutical composition for use of any one of embodiments II-56 to II-71, wherein the oral pharmaceutical composition is administered as one, two, three, or four unit dosage forms.

Embodiment II-73. The oral pharmaceutical composition for use of any one of embodiments II-56 to II-72, wherein the oral pharmaceutical composition is administered as one or two unit dosage forms.

Embodiment II-74. The oral pharmaceutical composition for use of any one of embodiments II-56 to II-73, wherein the oral pharmaceutical composition is administered as two or three unit dosage forms each comprising 68.5 to 175 mg amantadine, or an equivalent amount of a pharmaceutically acceptable salt thereof.

Embodiment II-75. The oral pharmaceutical composition for use of any one of claims 56 to 74, wherein the drug is a pharmaceutically acceptable salt of amantadine.

Embodiment II-76. The oral pharmaceutical composition for use of any one of embodiments II-56 to II-75, wherein the drug is amantadine hydrochloride.

EXAMPLES

The present disclosure may be better understood by reference to the following examples, which are illustrative and not intended to limit the scope of the disclosure in any way.

Example 1: Amantadine Extended Release Coated Pellet Formulation of Type C

Amantadine HCl extended release coated pellet compositions designed for oral administration were prepared using the components and relative amounts shown in Table 1 below.

The drug coating dispersion was prepared by adding HPMC 5 cps and Copovidone to isopropyl alcohol with continuous stirring. Purified water was added to this dispersion and stirring continued until a clear solution is formed. Drug (Amantadine HCl) was then added to this clear solution and stirring continued until the drug was completely dissolved. Finally, talc was added and dispersed uniformly by stirring.

The seed pellets, Celphere beads (screen sizes #35 to #50 i.e., 300 to 500 micron), were loaded in a Wurster coating unit. The drug coating dispersion was sprayed onto the seed pellets to the desired increase in coat weight, providing a drug coating of amantadine and excipients on the seed pellets, followed by a period of drying to remove residual organic solvent and water in the drug coated pellets. The resulting drug coated pellets were sieved to retain the fraction between screens #18 and #24 (approximately 700 μm to 1 mm diameter).

The seal coating dispersion was prepared by adding HPMC 5 cps to isopropyl alcohol with continuous stirring. Purified water was added to this dispersion and stirring continued until a clear solution was formed. Talc was added and dispersed uniformly by stirring. The sieved drug coated pellets were loaded in a Wurster coating unit. The seal coating dispersion was sprayed over the drug coated pellets followed by a period of drying to remove residual organic solvent and water in the pellets. The resulting seal coated pellets were sieved to retain the fraction between screens #18 and #24.

The ER coating solution was prepared by dissolving ethyl cellulose (viscosity 7 cps) in isopropyl alcohol and purified water and stirring until a clear solution was formed. Povidone K-90 was then dissolved in this clear solution followed by addition of plasticizer Miglyol 812N with continuous stirring to form a clear solution. The sieved seal coated pellets were loaded in a Wurster coating unit. The ER coating solution was sprayed over the seal coated pellets followed by a period of drying to affect the ER coat and remove residual organic solvent and water in the pellets. After drying, magnesium stearate was spread on the top bed of the coated pellets in the annulus region followed by recirculation of the pellets in the Wurster unit to blend the magnesium stearate with the coated pellets. The resulting ER coated pellets were sieved to retain the fraction between screens #18 and #24.

The ER coated pellets containing the unit dose of amantadine hydrochloride were filled into empty hard gelatin capsule shells using an encapsulator equipped with pellet dosing chamber. For 48.4 mg amantadine (60 mg amantadine HCl) and 112.8 mg amantadine (140 mg amantadine HCl) size 1 capsule shells were used. The 48.4 mg capsules had a water content of 2.0% by Karl Fischer and a residual isopropyl alcohol level of 6464 ppm; the 112.8 mg capsules had a water content of 1.8% by Karl Fischer and a residual isopropyl alcohol level of 6709 ppm.

TABLE 1

Composition of Type C amantadine HCl ER capsules

| Component | Function | combined w/w of capsule |
|---|---|---|
| Seed Pellet | | |
| Microcrystalline cellulose spheres (Celphere ®), NF | Core seeds | 12.54% |
| Drug Coating Dispersion | | |
| Amantadine Hydrochloride, USP | Active | 43.89% |
| Hydroxypropyl methyl cellulose, 5 cps, USP | Binder | 11.70% |
| Copovidone, NF | Binder | 2.92% |
| Talc, NF | Anti-tack | 2.19% |
| Isopropyl alcohol, USP | Solvent | Trace[1] |
| Purified Water, USP | Solvent | Trace[1] |
| Seal Coating Dispersion | | |
| Hydroxypropyl methyl cellulose, 5 cps, USP | Coating polymer | 6.66% |
| Talc, NF | Anti-tack | 0.67% |
| Isopropyl alcohol, USP | Solvent | Trace[1] |
| Purified Water, USP | Solvent | Trace[1] |
| Extended Release Coating | | |
| Ethyl cellulose, 7 cps, NF | Coating polymer | 15.39% |
| Povidone K-90, USP | Pore former | 2.08% |
| Medium chain triglycerides (Miglyol 812N), NF | Plasticizer | 1.86% |
| Isopropyl alcohol, USP | Solvent | Trace[1] |
| Purified Water, USP | Solvent | Trace[1] |
| Lubricant | | |
| Magnesium Stearate NF | Lubricant | 0.10% |

Notes:
USP,—United States Pharmacopeia,
NF = National Formulary,
All ingredient quantities are % w/w
[1]Purified water and isopropyl alcohol are removed during processing.

Example 2: Amantadine Extended Release Coated Pellet Formulation of Type D

Amantadine HCl extended release coated pellet compositions designed for oral administration were prepared using the components and relative amounts shown in Table 2 below.

The drug coating dispersion was prepared by combining the coating dispersion components of Table 2 in purified water without an organic solvent.

The seed pellets, Celphere beads (screen sizes #35 to #50 i.e., 300 to 500 micron), were loaded in a Wurster coating unit. The drug coating dispersion was sprayed onto the seed pellets to the desired increase in coat weight, providing a drug coating of amantadine and excipients on the seed pellets, followed by a period of drying to remove residual water. The resulting drug coated pellets were sieved to retain the fraction between screens #18 and #24 (approximately 700 μm to 1 mm diameter).

The seal coating dispersion was prepared by combining the components of the seal coating dispersion of Table 2 in purified water without organic solvent. The sieved drug coated pellets were loaded in a Wurster coating unit. The seal coating dispersion was sprayed over the drug coated pellets followed by a period of drying to remove residual water in the pellets. The resulting seal coated pellets were sieved to retain the fraction between screens #18 and #24.

The ER coating solution was prepared by dissolving ethyl cellulose (viscosity 7 cps) in isopropyl alcohol and purified water and stirring until a clear solution was formed. Povidone K-90 was then dissolved in this clear solution followed by addition of plasticizer Miglyol 812N with continuous stirring to form a clear solution. The sieved seal coated pellets were loaded in a Wurster coating unit. The ER coating solution was sprayed over the seal coated pellets followed by a period of drying to affect the ER coat and remove residual organic solvent and water in the pellets. After drying, magnesium stearate was spread on the top bed of the coated pellets in the annulus region followed by recirculation of the pellets in the Wurster unit to blend the magnesium stearate with the coated pellets. The resulting ER coated pellets were sieved to retain the fraction between screens #18 and #24.

The ER coated pellets containing the unit dose of amantadine hydrochloride were filled into empty hard gelatin capsule shells using an encapsulator equipped with pellet dosing chamber. For 68.5 mg amantadine (85 mg amantadine HCl), size 2 capsule shells were used. For 137 mg amantadine (170 mg amantadine HCl), size 0 capsule shells were used. The capsules had a water content of 2% by Karl Fischer and a residual isopropyl alcohol level of 1051 ppm.

TABLE 2

Composition of Type D amantadine HCl ER capsules

| Component | Function | combined w/w of capsule |
|---|---|---|
| Seed Pellet | | |
| Microcrystalline cellulose spheres (Celphere ®), NF | Core seeds | 12.44% |
| Drug Coating Dispersion | | |
| Amantadine Hydrochloride, USP | Active | 43.54% |
| Hydroxypropyl methyl cellulose, USP | Binder | 11.61% |
| Copovidone, NF | Binder | 2.90% |
| Talc, NF | Anti-tack | 2.17% |
| Purified Water, USP | Solvent | Trace[1] |
| Seal Coating Dispersion | | |
| Hydroxypropyl methyl cellulose, USP | Coating polymer | 6.60% |
| Talc, NF | Anti-tack | 0.66% |
| Purified Water, USP | Solvent | Trace[1] |

TABLE 2-continued

Composition of Type D amantadine HCl ER capsules

| Component | Function | combined w/w of capsule |
|---|---|---|
| Extended Release Coating | | |
| Ethyl cellulose, 7 cps, NF | Coating polymer | 15.91% |
| Povidone K-90, USP | Pore former | 2.15% |
| Medium chain triglycerides (Miglyol 812N), NF | Plasticizer | 1.92% |
| Isopropyl alcohol, USP | Solvent | Trace[1] |
| Purified Water, USP | Solvent | Trace[1] |
| Lubricant | | |
| Magnesium Stearate, NF | Lubricant | 0.10% |

Notes:
USP,—United States Pharmacopeia,
NF = National Formulary,
All ingredient quantities are % w/w
[1] Purified water and isopropyl alcohol are removed during processing.

Example 3: Dissolution of Amantadine Extended Release Coated Pellet Formulations Dissolution of the capsules of Examples 1 and 2 were performed using a USP Apparatus II (Paddles) at 50 rpm with 500 ml water at 37.0±0.5° C. as the dissolution medium. The mean results are shown in Table 3 below and FIG. 1.

The in vitro dissolution shows a decreased release of amantadine from the compositions over the first 4, 6 and 8 hours.

TABLE 3

Dissolution profiles

| | Percent Released | |
|---|---|---|
| Time (hr) | Type C (Ex. 1) | Type D (Ex. 2) |
| 2 | 2 | 1 |
| 4 | 18 | 9 |
| 6 | 44 | 31 |
| 8 | 68 | 61 |
| 10 | 83 | 82 |
| 12 | 93 | 94 |
| 16 | N/A | 102 |

Example 4: Pharmacokinetic Study of Two Amantadine ER Coated Pellet Formulations Objective: The primary objective of the study was to evaluate the pharmacokinetic profiles of the two formulations of ER amantadine HCl of Examples 1 and 2. The secondary objective was to evaluate the safety and tolerability of a single 340 mg dose of the two formulations of ER amantadine HCl of Examples 1 and 2.

Study design: This was a Phase 1, randomized, single dose, open-label, two-period, two-treatment crossover, fasting pharmacokinetic study in which single 340 mg doses of formulations of Example 1 (Type C) and Example 2 (Type D) Amantadine ER capsules, i.e. study drugs, were compared to each other. The study included 42 healthy subjects who were randomly assigned in a 1:1 ratio to 1 of 2 treatment sequences (Type C→Type D or Type D→Type C). For type C, 340 mg amantadine hydrochloride consisted of two 140 mg capsules and one 60 mg capsule. For type D, 340 mg amantadine hydrochloride consisted of two 170 mg capsules.

Methods: Subjects were screened for inclusion and exclusion criteria within 21 days of study screening. On the day prior to the first period of dosing, subjects were admitted to the unit and remained there until after the 48 hour blood sample was taken. In each study period, subjects were dosed on the day after checking into the unit and discharged after the 48 hour post-dose blood sample was taken. Subjects returned to the unit for subsequent blood draws (72 hours and 96 hours). There was a 7 to 14 day washout period between the first and second dose. Safety monitoring was conducted during and after administration of each study drug.

For each study period, after an overnight fast, the study drug was administered to the subjects while in a sitting position with 240 mL of water. Subjects were required to remain in a sitting position for at least 2 hours after administration. No food was permitted until 4 hours after administration of study drug. Blood samples were collected at 0 (pre-dose), 1, 2, 3, 4, 6, 8, 10, 12, 13, 14, 15, 16, 18, 20, 24, 30, 36, 48, 72 and 96 hours following each dose. Plasma samples were assayed for amantadine by a validated liquid chromatography/tandem mass spectroscopy (LC/MS/MS) method. Pharmacokinetic parameters were calculated using a non-compartmental analysis with WinNonlin software (version 6.2.1; Pharsight Corporation).

Adverse events were monitored throughout the study. Vital signs (pulse rate, blood pressure and body temperature), clinical laboratory measures (biochemistry, hematology, and urinalysis) and ECGs were collected at various times during the study.

Results: A total of 42 subjects comprising healthy male and female adults were screened and randomly assigned to the treatment arms described above, and 39 subjects completed the study. All 42 subjects were included in the safety population and 39 subjects were included in the primary analysis population.

Figure 2:
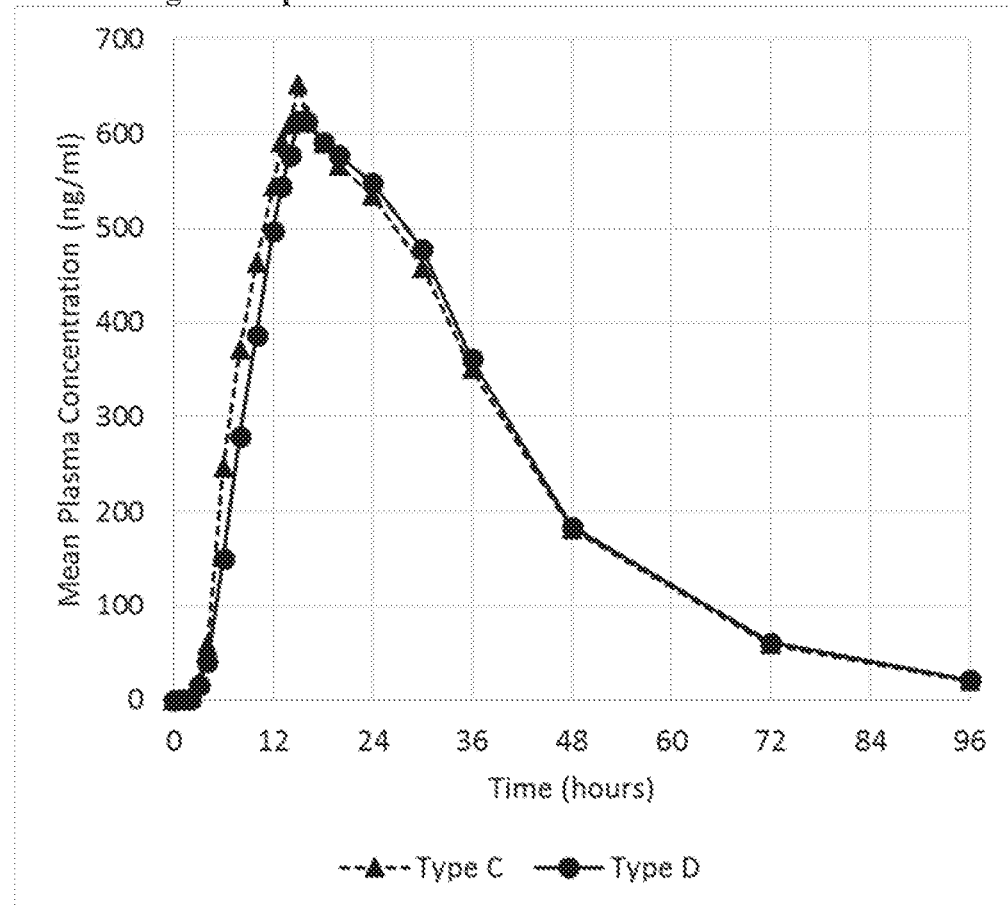
FIG. 2 and FIG. 3 show the mean concentrations over time after administration of two formulations of Examples 1 and 2 in the single dose fasting human pharmacokinetic study described in Example 4.

The pharmacokinetic results from this study shown in Table 4 below and FIG. 2 demonstrate that these formulations provide similar Cmax, Tmax, $AUC_{0-inf}$, $AUC_{0-24}$ and $t_{1/2}$.

TABLE 4

Pharmacokinetic data for single dose PK study
(Mean ± SD except as noted)

| Parameter | Type C (n = 39) | Type D (n = 39) |
|---|---|---|
| $AUC_{0-inf}$ (ng*hr/ml) | 22687.6 ± 7747.79 | 22442.2 ± 8291.63 |
| $AUC_{0-24}$ (ng*hr/ml) | 9805.6 ± 2361.02 | 9111.0 ± 2236.41 |
| Cmax (ng/ml) | 670.9 ± 180.76 | 660.2 ± 183.05 |
| Tmax (hr)$^a$ | 15.0 [12.0, 24.02] | 16.0 [12.0, 30.13] |
| $t_{1/2}$ (hr) | 13.614 ± 3.1252 | 13.752 ± 3.6535 |

$^a$Tmax is the median value data within square brackets are min and max values.

Figure 3:
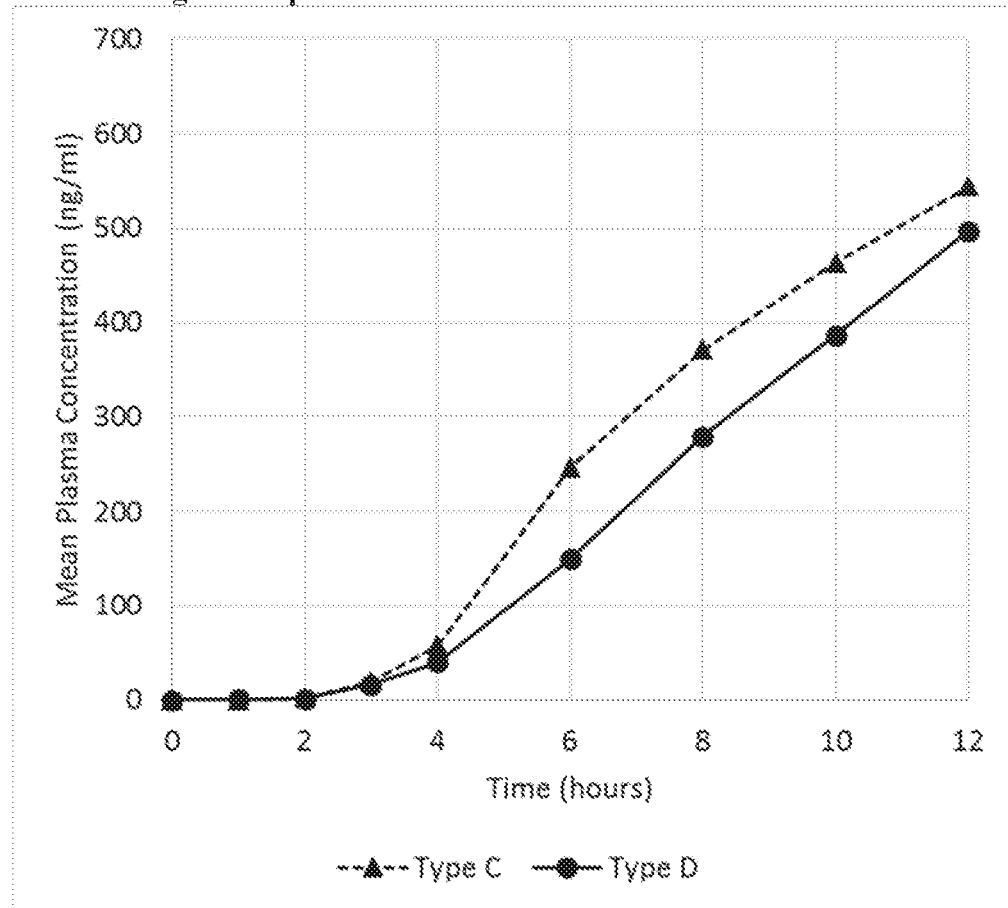

From partial AUC values for the two formulations over the first 4, 6, 8, 10, 12, 14 and 16 hours, the exposure in the early hours after administration for type D compositions is less than for the Type C composition, see Table 5 below. This is also shown in FIG. 3.

TABLE 5 pAUC values (ng * hr/ml per mg amantadine HCl) for single dose PK study

| Time (hr) | Type C | Type D |
|---|---|---|
| 4 | 0.15 | 0.11 |
| 6 | 1.04 | 0.67 |

TABLE 5-continued pAUC values (ng * hr/ml per mg amantadine HCl) for single dose PK study

| Time (hr) | Type C | Type D |
|---|---|---|
| 8 | 2.85 | 1.93 |
| 10 | 5.31 | 3.89 |
| 12 | 8.27 | 6.49 |
| 14 | 11.71 | 9.67 |
| 16 | 15.43 | 13.23 |
| 18 | 18.98 | 16.77 |

Safety results: within the 42 subjects randomized to the study, adverse events were recorded and coded using MedDRA Version 17.0. The number and percentage of the population reporting at least one adverse event within the system organ class are shown in Table 6 below. The gastrointestinal disorder frequencies for the Type C and Type D compositions were compared with a logistic models fit using generalized estimating equations (GEE, Exchangeable Correlation Structure). The analysis provided an odds ratio of 3.407 and a p-value of 0.0685, indicating that the odds of a gastrointestinal adverse event is 3.4 times greater for the Type C formulation than for the Type D formulation.

TABLE 6

Adverse events observed

| MedDRA System Organ Class | Number (%) of subjects with Adverse Events | |
|---|---|---|
| | Type C (n = 40) | Type D (n = 41) |
| Subjects with at least 1 AE | 7 (17.5%) | 3 (7.3%) |
| Gastrointestinal disorders | 4 (10.0%) | 1 (2.4%) |
| Nervous system disorders | 1 (2.5%) | 1 (2.4%) |
| General disorders and administration site conditions | 0 | 1 (2.4%) |
| Infections and infestations | 1 (2.5%) | 0 |
| Injury, poisoning and procedural complications | 1 (2.5%) | 0 |
| Metabolism and nutrition disorders | 0 | 1 (2.4%) |
| Psychiatric disorders | 1 (2.5%) | 1 (2.4%) |

Example 5: Statistical Analysis of GI Adverse Events Across Multiple Studies

Objective: to compare the incidence of gastrointestinal adverse events from single dose, fasting human pharmacokinetic studies for Type C and Type D formulations.

This post hoc analysis combined the gastrointestinal adverse events (based on MedDRA coding) across 5 single dose, fasting human pharmacokinetic studies to determine if the gastrointestinal adverse event difference observed in Example 4 is statistically significant. For studies with treatments other than Type C or Type D formulations, only the Type C and Type D arms were included. Furthermore, only single dose, fasting arms were included. Combining the results provided both a greater number of subjects and a greater number of adverse events. The studies included are detailed in Table 7 below. Statistical analysis of the data was performed using a logistic models fit using generalized estimating equations (GEE, Exchangeable Correlation Structure).

TABLE 7

Number of subjects and number of GI adverse events in studies for analysis

|  | Type C | | Type D | |
| --- | --- | --- | --- | --- |
| Study Description, dose of amantadine HCl | N | GI AEs | N | GI AEs |
| A: formulation selection study, 100 mg | 18 | 5 | — | — |
| B: dose proportionality study, 85/170/340 mg[a] | — | — | 30 | 1 |
| C: bioequivalence study, 340 mg | 40 | 4 | 41 | 1 |
| D: food effect study, 170 mg (fasted only) | — | — | 36 | 0 |
| E: bioequivalence study, 170 mg[b] | — | — | 21 | 0 |

[a]this study compared three strengths of one Type D formulation, the GI AE observed was at the lowest strength
[b]two preparations of Type D formulations The studies included 147 different subjects and statistical results for the gastrointestinal adverse effects in the pooled data showed an odds ratio for Type C vs. Type D of 16.247 and a p-value of <0.0001. The smaller p-value as compared to the previous example may be partially explained by the increase in sample size and partially explained by the increase in magnitude of the effect (9 of 58 for Type C vs 2 of 128 for Type D).

Example 6: A Randomized, Double-Blind, Placebo-Controlled Study of the Efficacy and Safety of Amantadine Extended Release Oral Capsules for the Treatment of Levodopa-Induced Dyskinesia in Parkinson's Disease This study was performed using a formulation of amantadine hydrochloride prepared according the processes of Example 1 above, for Type C. Study Objectives: This study was designed to evaluate the efficacy of three dose levels of Amantadine Extended Release (ER) oral capsules dosed once nightly at nighttime for the treatment of levodopa-induced dyskinesia (LID) in subjects with Parkinson's Disease (PD). In addition, the study was designed to demonstrate the safety and tolerability of Amantadine ER oral capsules dosed once nightly for the treatment of LID in subjects with PD. Study design: This was a multi-center, randomized, double-blind, placebo-controlled, 4-arm parallel group study of Amantadine ER in subjects with PD who have LID. Consenting subjects who met eligibility criteria were randomized 1:1:1:1 to receive one of the following 4 treatments, each administered as once nightly, dosed at night:

Treatment A: Placebo,
Treatment B: 260 mg Amantadine ER (ADS-5102) (prepared according the process of Example 1 for Type C),
Treatment C: 340 mg Amantadine ER (ADS-5102) (prepared according the process of Example 1 for Type C)
Treatment D: 420 mg Amantadine ER (ADS-5102) (prepared according the process of Example 1 for Type C)

Subjects who were randomized to Treatment C received, in double-blind fashion, 260 mg Amantadine ER once nightly during week 1, with an increase to 340 mg once nightly at the beginning of week 2. Subjects who were randomized to Treatment D, in double-blind fashion, 260 mg Amantadine ER once nightly during week 1, with an increase to 340 mg Amantadine ER once nightly during week 2, with a further increase to 420 mg once nightly at the beginning of week 3. Dosing for all groups continued at the nominal dose through week 8.

Following completion of the baseline visit and randomization, subjects returned to the clinic after 1, 2, 4, 6, and 8 weeks of dosing, with a follow-up visit 14 days following the last dose of study drug. Study visits and assessments were scheduled during the hours between 10 am through 4 pm. A set of two 24-hour diaries were be completed during 48 hours prior to randomization and 48 hours prior to selected study visits. The diary was used to score five different conditions in 30-minute intervals: Sleep, OFF, ON without dyskinesias, ON with nontroublesome dyskinesias, ON with troublesome dyskinesias.

Blood samples were collected at selected study visits for determination of amantadine plasma concentrations, and evaluation of steady-state population pharmacokinetics. Subject participation during the study was up to 12 weeks including a 2-week (maximum) screening period, 8-week (maximum) treatment period, and a 2-week follow-up period. Subjects unable to tolerate their assigned study drug assignment permanently discontinued study drug and continued to be followed for safety through 2 weeks following the last dose of study drug.

Patient Eligibility Criteria: Subjects were eligible to take part in the study if they met the inclusion and did not meet the exclusion criteria. Selected key criteria were as follows:

Inclusion Criteria:
  Male or female adults
  Between 30 and 85 years of age, inclusive
  Ambulatory or ambulatory-aided (e.g. walker or cane) ability while ON, such that the subject can could complete study assessments
  Knowledgeable and reliable caregiver/study partner, if appropriate, to accompany the subject to study visits and assist in completion of study instruments, as needed and allowed
  Signed a current IRB/IEC-approved informed consent form
  Following diary training, the subject was willing and able to understand and complete the 24-hour PD home diary (caregiver/study partner assistance allowed)
  Parkinson's Disease, complicated per UK Parkinson's Disease Society (UKPDS) Brain Bank Clinical Diagnostic Criteria
  On a stable regimen of antiparkinson's medications, including levodopa, for at least 30 days prior to screening, with any levodopa administered not less than three times daily, and willing to continue the same doses and regimens during study participation
  A score of at least 2 on part IV, item 4.2 (functional impact of dyskinesias) of the Unified Parkinson's Disease Rating Scale (MDS-UPDRS), at screening and at Day 1 (baseline)
  Using the 48-hour PD home diaries completed just prior to Day 1 (baseline), at least 2 half-hour time periods between 10 am and 4 pm of each 24-hour period are indicated as "ON with troublesome dyskinesia"

Key Exclusion Criteria:
  History of deep brain simulation; history of exclusively diphasic, off state, myoclonic or akathetic dyskinesia without peak dose dyskinesia
  History of other neurological disease that, in the opinion of the investigator, would affect cognition or motor function, including, but not limited to Alzheimer's dementia, Huntington's disease, Lewy body dementia, frontotemporal dementia, corticobasal degeneration, progressive supranuclear palsy, multiple system atrophy, motor or sensory dysfunction secondary to stroke or brain trauma, or multi-infarct dementia with lacunae.
  Presence of cognitive impairment, as evidenced by a Mini-mental State Examination (MMSE) score of less than 24 during screening.

Presence of an acute or chronic major psychiatric disorder (e.g., Major Depressive Disorder) or symptom (e.g., hallucinations, agitation, paranoia) that, in the opinion of the investigator, would affect the subject's ability to complete study assessments History of sensory impairments (e.g., hearing, vision) that, in the opinion of the investigator, would impair the subject's ability to complete study assessments History of alcohol or drug dependence or abuse within 2 years prior to screening History of seizures within 2 years prior to screening History of stroke or TIA within 2 years prior to screening History of myocardial infarction, or NYHA Functional Classification of Heart Failure Class 3 or 4 within 2 years prior to screening History of cancer within 5 years prior to screening, with the following exceptions: adequately treated non-melanomatous skin cancers, localized bladder cancer, non-metastatic prostate cancer or in situ cervical cancer Any of the following laboratory test results at screening: Hemoglobin<10 g/dL, WBC<$3.0\times10^9$/L, Neutrophils<$1.5\times10^9$/L, Lymphocytes<$0.5\times10^9$/L, Platelets<$100\times10^9$/L, Hemoglobin A1C>9%, or Aspartate aminotransferase (AST) and/or alanine aminotransferase (ALT)>2 times the upper limit of normal Estimated GFR<50 mL/min/1.73 $m^2$ by Modification of Diet in Renal Disease (MDRD) equation Any clinically significant ECG abnormalities, including any findings of abnormal ventricular conduction of rhythm other than isolated PVCs or first degree AV block Inability to swallow oral capsules, or a history of gastrointestinal malabsorption that would preclude the use of oral medication Study Endpoints: The primary efficacy endpoint is the change from baseline to week 8 in the Unified Dyskinesia Rating Scale (UDysRS) total score. Key secondary endpoints include change from baseline to week 8:

Total Objective Score (III, IV) of the UDysRS

ON time without troublesome dyskinesia (ON without dyskinesia plus ON with non-troublesome dyskinesia), based on the PD home diary ON time with troublesome dyskinesia, based on a standardized PD home diary Total ON time with dyskinesia (non-troublesome and troublesome)

Total OFF time

Unified Parkinson's Disease Rating Scale (MDS-UPDRS), combined score (Parts I, II and III)

Unified Parkinson's Disease Rating Scale (MDS-UPDRS), part IV, items 4.1 (time spent with dyskinesias) and 4.2 (functional impact of dyskinesias)

Unified Parkinson's Disease Rating Scale (MDS-UPDRS), individual part scores (I, II, III, and IV)

Clinician's Global Impression of Change in overall PD symptoms, determined by a question completed by the investigator Health-related Quality of Life as measured by a PD-specific HRQoL instrument, the PDQ-39

Fatigue as measured by the Fatigue Severity Scale (FSS). This scale includes 9 questions that are completed by the patient using a rating scale from 1 (strongly disagree) to 7 (strongly agree). Safety, including adverse events, safety-related study drug discontinuations, vital signs, and laboratory tests.

The following mixture of traditional and new scales have been selected for this study:

Unified Dyskinesia Rating Scale (UDysRS) was used for primary outcome measure. This scale has four parts, and a total possible score of 104:

I: Historical Disability (patient perceptions) of On-Dyskinesia impact

II: Historical Disability (patient perceptions) of Off-Dystonia impact

III: Objective Impairment (dyskinesia severity, anatomic distribution, and type, based on 4 observed activities)

IV: Objective Disability based on Part III activities

ON time without troublesome dyskinesia, based on a standardized Parkinson's disease home diary.

MDS-Unified Parkinson's Disease Rating Scale (MDS-UPDRS), part IV, items 4.1 (duration of dyskinesias: 0=none, 4=76-100% of the waking day) and 4.2 (disability of dyskinesias: 0=not disabling, 4=completely disabling) was a secondary outcome measure.

Statistical Methods

Efficacy Analyses: The efficacy analysis population included all randomized and dosed subjects who provided at least one post-baseline efficacy assessment, and met pre-specified entry criteria. Unless specified otherwise, all efficacy endpoints were analyzed using analysis of covariance (ANCOVA) models with the change from baseline to Week 8 as the dependent variable, treatment group as a factor, and the baseline value of the corresponding endpoint as a covariate. These models will be used for both pair-wise comparisons between each amantadine ER dose group versus placebo and for testing for a linear dose-response relationship. The dose-response test will be carried out using the scores 0, 260, 340, and 420 and additionally using equally spaced scores for the treatment groups. For the efficacy endpoint of UDysRS score, the primary analysis compared the 340 mg amantadine ER group to the placebo group using a two-sided test at the 5% level of significance.

The secondary endpoints were analyzed using the same types of ANCOVA models as described for the primary endpoint, except for CGIC which was a CMH analysis. All secondary comparisons between treatment groups were performed using two-sided tests at the 5% level of significance. A last observation carried forward (LOCF) approach was utilized for missing data. The primary efficacy analysis was repeated for the per-protocol population, a subset of the efficacy analysis population who provided week 8 efficacy assessments. The CGI was a CMH analysis.

Results: selected study results are shown in the table below.

TABLE 8

| Instruments | Mean values and LS Mean changes (by Group) | | | | Effect | |
|---|---|---|---|---|---|---|
| | Placebo | 260 mg | 340 mg | 420 mg | | |
| Unified Dyskinesia Rating Scale | 39.2 | 40.2 | 44.1 | 41.2 | Baseline | Reduction in total UDysRS greater for the treatment |
| | −6.7 | −12.3 | −17.9 | −16.7 | LS change | |

TABLE 8-continued

| Instruments | Mean values and LS Mean changes (by Group) | | | | Effect | |
|---|---|---|---|---|---|---|
| | Placebo | 260 mg | 340 mg | 420 mg | | |
| (UDysRS) total score | — | −14% | −25% | −24% | (Active-Placebo)/Baseline | groups than placebo |
| Unified Dyskinesia Rating Scale (UDysRS) objective total (parts III, IV) | 13.5 −1.9 — | 16.7 −4.4 −15% | 18.7 −7.1 −28% | 15.8 −8.3 −41% | Baseline LS change (A-P)/base | Reduction in UDysRS total Objective greater for the treatment groups than placebo |
| Unified Parkinson's Disease Rating Scale (UPDRS, MDS revision), Part IV | 11.7 −1.5 — | 10.6 −2.2 −6.6% | 11.8 −3.9 −20% | 10.5 −4.9 −32% | Baseline LS change (A-P)/base | Reduction in MDS-UPDRS Part IV greater for the treatment groups than placebo |
| ON time without troublesome dyskinesia (hours) | 6.9 0.9 — | 6.6 4.1 48% | 7.7 3.8 38% | 9.0 3.6 30% | Baseline LS change (A-P)/base | Increase in ON time without troublesome dyskinesia for the treatment groups versus placebo |
| ON time with dyskinesia (hours) | 10.2 −1.9 — | 10.0 −3.0 −11% | 8.0 −4.0 −26% | 10.4 −5.0 −30% | Baseline LS change (A-P)/base | Decrease in ON time with dyskinesia for the treatment groups versus placebo |
| ON time with troublesome dyskinesia (hours) | 6.1 −1.4 — | 6.3 −2.7 −21% | 4.5 −3.2 −40% | 5.1 −4.2 −55% | Baseline LS change (A-P)/base | Decrease in ON time with troublesome dyskinesia for the treatment groups versus placebo |
| OFF time (hours) | 3.2 0.3 — | 2.7 −1.0 −48% | 4.3 −0.6 −21% | 2.2 0.4 5% | Baseline LS change (A-P)/base | Decrease in OFF time for the 260 mg and 340 mg treatment groups versus placebo |
| CGIC** | | Mean value at week 8 | | | | Improvement in CGIC |
| | 0.8 — | 1.4 75% | 1.9 138% | 1.3 62% | Mean (A-P)/P** | for all treatment groups versus placebo |

*Baseline is the mean value at the study baseline for the treatment group. LS mean change is the least squares change in the value at the 8 week time point for the treatment group. (A-P)/base equals (the LS mean change for the active group less the LS mean change for the placebo group) divided by the mean baseline value for the active group multiplied by 100%.
**The Clinician's Global Impression of Change (CGIC) is assessed on a 7 point scale (+3 "Marked Improvement" to −3 "Marked worsening") based on a response to the following question: "Considering your observations and impression of the subject's clinical status related to overall Parkinson's disease, including but not limited to Levodopa-induced Dyskinesias, how much has the subject changed between baseline and this visit?"

ON time without dyskinesia increased in all groups from baseline to 8 weeks, however the increase in ON time without dyskinesia for the treatment groups, including the 340 mg treatment group was larger than the increase for the placebo group.

The Clinician's Global Impression of Change in Overall PD symptoms is summarized in the table below. The results for the MITT population show a statistically significant improvement for the 340 mg treatment group, but not for the other groups.

TABLE 9

| Visit: Day 57/ Visit 8 Category | Placebo (N = 22) | 260 mg ADS-5102 (N = 19) | 340 mg ADS-5102 (N = 20) | 420 mg ADS-5102 (N = 19) |
|---|---|---|---|---|
| Marked Improvement | 1 (4.5) | 2 (10.5) | 7 (35.0) | 4 (21.1) |
| Moderate Improvement | 6 (27.3) | 8 (42.1) | 8 (40.0) | 6 (31.6) |
| Minimal Improvement | 4 (18.2) | 5 (26.3) | 1 (5.0) | 5 (26.3) |
| No Change | 10 (45.5) | 3 (15.8) | 4 (20.0) | 2 (10.5) |
| Minimal Worsening | 1 (4.5) | 1 (5.3) | 0 | 0 |
| Moderate Worsening | 0 | 0 | 0 | 2 (10.5) |
| Marked Worsening | 0 | 0 | 0 | 0 |
| P-value[1] | | 0.1042 | 0.0036 | 0.2158 |

[1]The p-value is from the Cochran-Mantel-Haenszel mean score test (using equally spaced scores).

The CGI-C results indicated that 75% of patients in the 340 mg dose group had a moderate to marked improvement in their clinical status (related to overall PD, including but not limited to LID) at week 8, versus 32% of placebo patients. Additional summaries of the analysis are provided in the figures. Additional discussion of this data may be found in US20150087721.

While certain embodiments of the present disclosure have been shown and described herein, such embodiments are provided by way of example only. Numerous variations, changes, and substitutions will now occur to those skilled in the art without departing from the disclosure. It should be understood that various alternatives to the embodiments of the disclosure described herein may be employed in practicing the methods or preparing the compositions as described herein. All references cited herein are incorporated herein by reference in their entirety.

Example 7: A Randomized, Double-Blind, Placebo-Controlled Study of the Efficacy and Safety of Two Formulations of Amantadine Extended Release Oral Capsules for the Treatment of Levodopa-Induced Dyskinesia in Parkinson's Disease Study Objectives: This study is designed to evaluate the efficacy of two different formulations of Amantadine Extended Release (ER) oral capsules dosed once nightly at nighttime for the treatment of levodopa-induced dyskinesia (LID) in subjects with Parkinson's Disease (PD). In addition, the study is designed to demonstrate the safety and tolerability of two formulations of Amantadine ER oral capsules dosed once nightly for the treatment of LID in subjects with PD. Study design: This is a multi-center, randomized, double-blind, placebo-controlled, 3-arm parallel group study of Amantadine ER formulations in patients with PD who have LID. Consenting subjects who meet eligibility criteria are randomized 1:1:1 to receive one of the following 3 treatments, each administered as once nightly, dosed at night:

Treatment A: Placebo,

Treatment B: 340 mg Amantadine Hydrochloride ER (Type C),

Treatment C: 340 mg Amantadine Hydrochloride ER (Type D)

Subjects who are randomized to Treatment B or C received, in double-blind fashion, 170 mg Amantadine Hydrochloride ER of Type C or Type D, respectively, once nightly during week 1, with an increase to 340 mg Amantadine Hydrochloride ER of Type C or Type D, respectively, once nightly at the beginning of week 2. Dosing for all groups is continued at the nominal dose through week 8.

Following completion of the baseline visit and randomization, subjects return to the clinic after 1, 2, 4, 6, and 8 weeks of dosing, with a follow-up visit 14 days following the last dose of study drug. Study visits and assessments are scheduled during the hours between 10 am through 4 pm. A set of two 24-hour diaries are completed during 48 hours prior to randomization and 48 hours prior to selected study visits. The diary is used to score five different conditions in 30-minute intervals: Sleep, OFF, ON without dyskinesias, ON with nontroublesome dyskinesias, ON with troublesome dyskinesias.

Blood samples are collected at selected study visits for determination of amantadine plasma concentrations, and evaluation of steady-state population pharmacokinetics. Subject participation during the study is up to 12 weeks including a 2-week (maximum) screening period, 8-week (maximum) treatment period, and a 2-week follow-up period. Subjects unable to tolerate their assigned study drug assignment permanently are discontinued study drug and are followed for safety through 2 weeks following the last dose of study drug.

Patient Eligibility Criteria: Subjects are eligible to take part in the study if they met the inclusion and do not meet the exclusion criteria. Selected key criteria are as follows:

Inclusion Criteria:
  Male or female adults
  Between 30 and 85 years of age, inclusive
  Ambulatory or ambulatory-aided (e.g. walker or cane) ability while ON, such that the subject can could complete study assessments
  Knowledgeable and reliable caregiver/study partner, if appropriate, to accompany the subject to study visits and assist in completion of study instruments, as needed and allowed
  Sign a current IRB/IEC-approved informed consent form
  Following diary training, the subject is willing and able to understand and complete the 24-hour PD home diary (caregiver/study partner assistance allowed)
  Parkinson's Disease, complicated per UK Parkinson's Disease Society (UKPDS) Brain Bank Clinical Diagnostic Criteria
  On a stable regimen of antiparkinson's medications, including levodopa, for at least 30 days prior to screening, with any levodopa administered not less than three times daily, and willing to continue the same doses and regimens during study participation
  A score of at least 2 on part IV, item 4.2 (functional impact of dyskinesias) of the Unified Parkinson's Disease Rating Scale (MDS-UPDRS), at screening and at Day 1 (baseline)
  Using the 48-hour PD home diaries completed just prior to Day 1 (baseline), at least 2 half-hour time periods between 10 am and 4 pm of each 24-hour period are indicated as "ON with troublesome dyskinesia"

Key Exclusion Criteria:
  History of deep brain simulation; history of exclusively diphasic, off state, myoclonic or akathetic dyskinesia without peak dose dyskinesia
  History of other neurological disease that, in the opinion of the investigator, would affect cognition or motor function, including, but not limited to Alzheimer's dementia, Huntington's disease, Lewy body dementia, frontotemporal dementia, corticobasal degeneration, progressive supranuclear palsy, multiple system atrophy, motor or sensory dysfunction secondary to stroke or brain trauma, or multi-infarct dementia with lacunae.
  Presence of cognitive impairment, as evidenced by a Mini-mental State Examination (MMSE) score of less than 24 during screening.
  Presence of an acute or chronic major psychiatric disorder (e.g., Major Depressive Disorder) or symptom (e.g., hallucinations, agitation, paranoia) that, in the opinion of the investigator, would affect the subject's ability to complete study assessments
  History of sensory impairments (e.g., hearing, vision) that, in the opinion of the investigator, would impair the subject's ability to complete study assessments
  History of alcohol or drug dependence or abuse within 2 years prior to screening
  History of seizures within 2 years prior to screening
  History of stroke or TIA within 2 years prior to screening
  History of myocardial infarction, or NYHA Functional Classification of Heart Failure Class 3 or 4 within 2 years prior to screening
  History of cancer within 5 years prior to screening, with the following exceptions: adequately treated non-melanomatous skin cancers, localized bladder cancer, non-metastatic prostate cancer or in situ cervical cancer
  Any of the following laboratory test results at screening: Hemoglobin<10 g/dL, WBC<3.0×10$^9$/L, Neutrophils<1.5×10$^9$/L, Lymphocytes<0.5×10$^9$/L, Platelets<100×10$^9$/L, Hemoglobin A1C>9%, or Aspartate aminotransferase (AST) and/or alanine aminotransferase (ALT)>2 times the upper limit of normal
  Estimated GFR<50 mL/min/1.73 m$^2$ by Modification of Diet in Renal Disease (MDRD) equation
  Any clinically significant ECG abnormalities, including any findings of abnormal ventricular conduction of rhythm other than isolated PVCs or first degree AV block
  Inability to swallow oral capsules, or a history of gastrointestinal malabsorption that would preclude the use of oral medication Study Endpoints: The primary efficacy endpoint is the change from baseline to week 8 in the Unified Dyskinesia Rating Scale (UDysRS) total score. Key secondary endpoints include change from baseline to week 8:
  Total Objective Score (III, IV) of the UDysRS
  ON time without troublesome dyskinesia (ON without dyskinesia plus ON with non-troublesome dyskinesia), based on the PD home diary
  ON time with troublesome dyskinesia, based on a standardized PD home diary
  Total ON time with dyskinesia (non-troublesome and troublesome)
  Total OFF time
  Unified Parkinson's Disease Rating Scale (MDS-UPDRS), combined score (Parts I, II and III)
  Unified Parkinson's Disease Rating Scale (MDS-UPDRS), part IV, items 4.1 (time spent with dyskinesias) and 4.2 (functional impact of dyskinesias)

Unified Parkinson's Disease Rating Scale (MDS-UP-DRS), individual part scores (I, II, III, and IV)

Clinician's Global Impression of Change in overall PD symptoms, determined by a question completed by the investigator Health-related Quality of Life as measured by a PD-specific HRQoL instrument, the PDQ-39

Fatigue as measured by the Fatigue Severity Scale (FSS). This scale includes 9 questions that are completed by the patient using a rating scale from 1 (strongly disagree) to 7 (strongly agree). Safety, including adverse events, safety-related study drug discontinuations, vital signs, and laboratory tests.

The following mixture of traditional and new scales have been selected for this study:

Unified Dyskinesia Rating Scale (UDysRS) was used for primary outcome measure. This scale has four parts, and a total possible score of 104:

I: Historical Disability (patient perceptions) of On-Dyskinesia impact

II: Historical Disability (patient perceptions) of Off-Dystonia impact

III: Objective Impairment (dyskinesia severity, anatomic distribution, and type, based on 4 observed activities)

IV: Objective Disability based on Part III activities

ON time without troublesome dyskinesia, based on a standardized Parkinson's disease home diary.

MDS-Unified Parkinson's Disease Rating Scale (MDS-UPDRS), part IV, items 4.1 (duration of dyskinesias: 0=none, 4=76-100% of the waking day) and 4.2 (disability of dyskinesias: 0=not disabling, 4=completely disabling) was a secondary outcome measure.

Statistical Methods

Efficacy Analyses: The efficacy analysis population includes all randomized and dosed subjects who provide at least one post-baseline efficacy assessment, and meet pre-specified entry criteria. Unless specified otherwise, all efficacy endpoints are analyzed using analysis of covariance (ANCOVA) models with the change from baseline to Week 8 as the dependent variable, treatment group as a factor, and the baseline value of the corresponding endpoint as a covariate. These models are used for both pair-wise comparisons between each amantadine ER dose group versus placebo. For the efficacy endpoint of UDysRS score, the primary analysis compares each amantadine ER group (Treatment B and Treatment C) to the placebo group using a two-sided test at the 5% level of significance. Similarly, for the efficacy endpoint of UDysRS score, the primary analysis compares the amantadine ER Treatment B to Treatment C using a two-sided test at the 5% level of significance.

The secondary endpoints are analyzed using the same types of ANCOVA models as described for the primary endpoint, except for CGIC which is a CMH analysis. All secondary comparisons between treatment groups are performed using two-sided tests at the 5% level of significance. A last observation carried forward (LOCF) approach is utilized for missing data. The primary efficacy analysis is repeated for the per-protocol population, a subset of the efficacy analysis population who provide week 8 efficacy assessments. The CGI is a CMH analysis.

Results: selected study results are shown in the table below.

TABLE 10

| Instruments | Effect |
| --- | --- |
| Unified Dyskinesia Rating Scale (UDysRS) total score | Reduction in total UDysRS greater for the treatment groups than placebo. Comparable reduction in total UDysRS for Treatment B and Treatment C |
| Unified Dyskinesia Rating Scale (UDysRS) objective total (parts III, IV) | Reduction in UDysRS total Objective greater for the treatment groups than placebo. Comparable reduction in UDysRS total Objective for Treatment B and Treatment C |
| Unified Parkinson's Disease Rating Scale (UPDRS, MDS revision), Part IV | Reduction in MDS-UPDRS Part IV greater for the treatment groups than placebo. Comparable reduction in MDS-UPDRS Part IV for Treatment B and Treatment C |
| ON time without troublesome dyskinesia (hours) | Increase in ON time without troublesome dyskinesia for the treatment groups versus placebo. Comparable increase in ON time without troublesome dyskinesia vs. Placebo for Treatment B and Treatment C |
| ON time with dyskinesia (hours) | Decrease in ON time with dyskinesia for the treatment groups vs. Placebo. Comparable decrease in ON time with dyskinesia vs. Placebo for Treatment B and Treatment C |
| ON time with troublesome dyskinesia (hours) | Decrease in ON time with troublesome dyskinesia vs. Placebo for the treatment groups. Comparable decrease in ON time with troublesome dyskinesia vs. Placebo for Treatment B and Treatment C |
| OFF time (hours) | Decrease in OFF time for the treatment groups vs. Placebo. Comparable decrease in OFF time for the vs. Placebo for Treatment B and Treatment C |
| CGIC** | Improvement in CGIC vs. Placebo for treatment groups. Comparable improvement in CGIC vs. Placebo for Treatment B and Treatment C |

**The Clinician's Global Impression of Change (CGIC) is assessed on a 7 point scale (+3 "Marked Improvement" to -3 "Marked worsening") based on a response to the following question: "Considering your observations and impression of the subject's clinical status related to overall Parkinson's disease, including but not limited to Levodopa-induced Dyskinesias, how much has the subject changed between baseline and this visit?"

ON time without dyskinesia is expected to increase more in Treatment B and Treatment C groups from baseline to 8 weeks than any change for Treatment A (Placebo).

The Clinician's Global Impression of Change in Overall PD symptoms is expected to show improvement for Treatment B and Treatment C groups at the end of the treatment period. The results for Treatment B and Treatment C is expected to be similar.

Safety results: Adverse events are recorded throughout the study and coded MedDRA classifications. Gastrointestinal disorders are expected to be lowest for Treatment Group A (Placebo). The frequency of gastrointestinal disorders is expected to be lower for Treatment C than for Treatment B. Gastrointestinal disorders for Treatment C are expected to be less than the 19.5% rate observed by Hayden (1981) for daily administration of 300 mg amantadine hydrochloride in divided doses. The frequency of sleep related adverse events is expected to be similar across the groups and not statistically significant from one group to another.

Example 8: Approaches to Reducing Residual Solvent

For amantadine ER formulations manufactured in a manner similar to that described in Example 1 (Type C) described above, various approaches to reducing the amount of residual solvent were attempted.

Batches of amantadine extended release coated pellet formulation were prepared using a ratio of isopropyl alcohol (IPA) to purified water of 40:60, 60:40 and 95:5 w/w in the drug coating, seal coating, and ER coating dispersions, respectively. Changes in drug coating process parameters were made in an attempt to reduce the level of residual solvent. These changes included intermittent drying at different times during drug coating, drying at a higher temperature (80° C.), drying at a lower humidity, increasing drying time, and increasing in product (drug coating) temperature during coating. None of these changes in process led to significant reduction in residual IPA.

Figure 4:
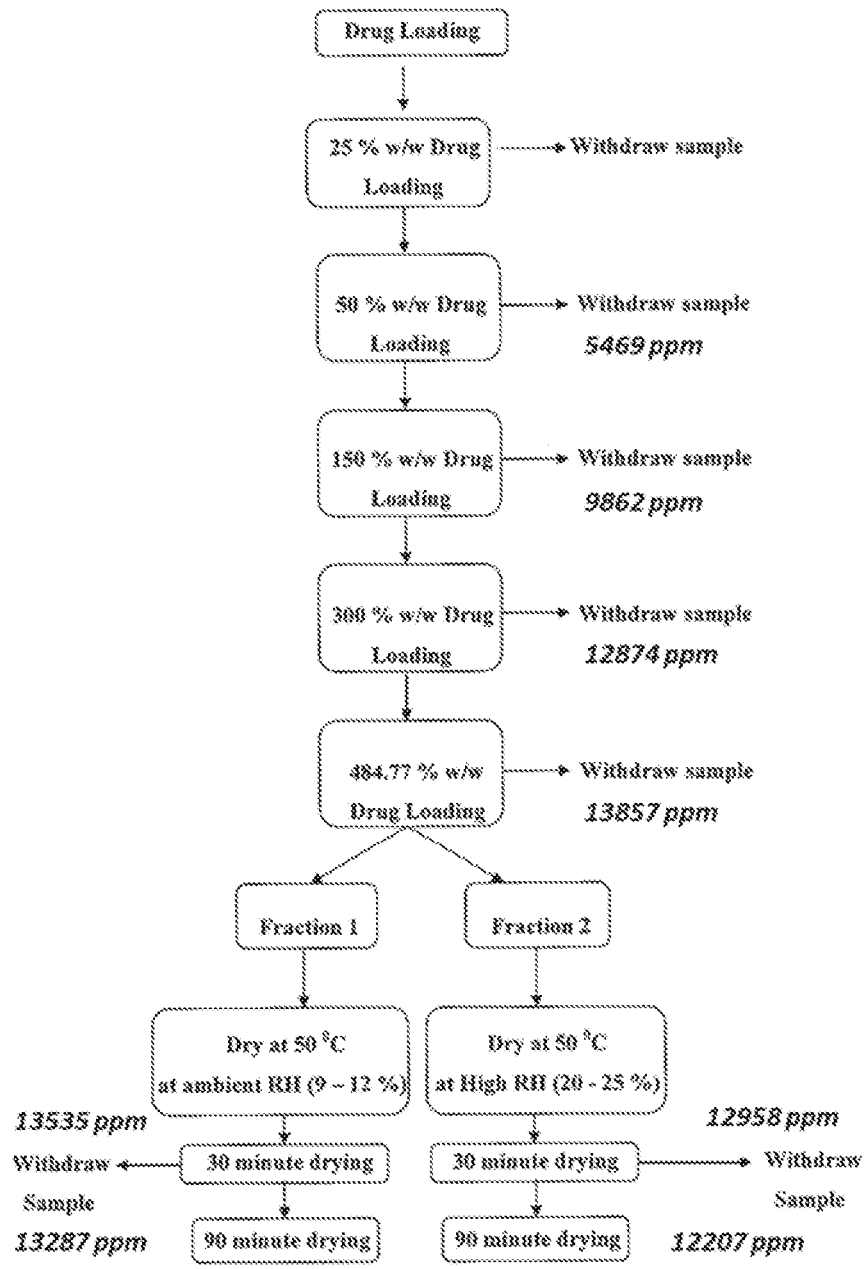
FIG. 4 is a schematic showing the isopropanol content at various points during drug-coating of pellets, without intermediate drying (Batch 166).
Figure 5:
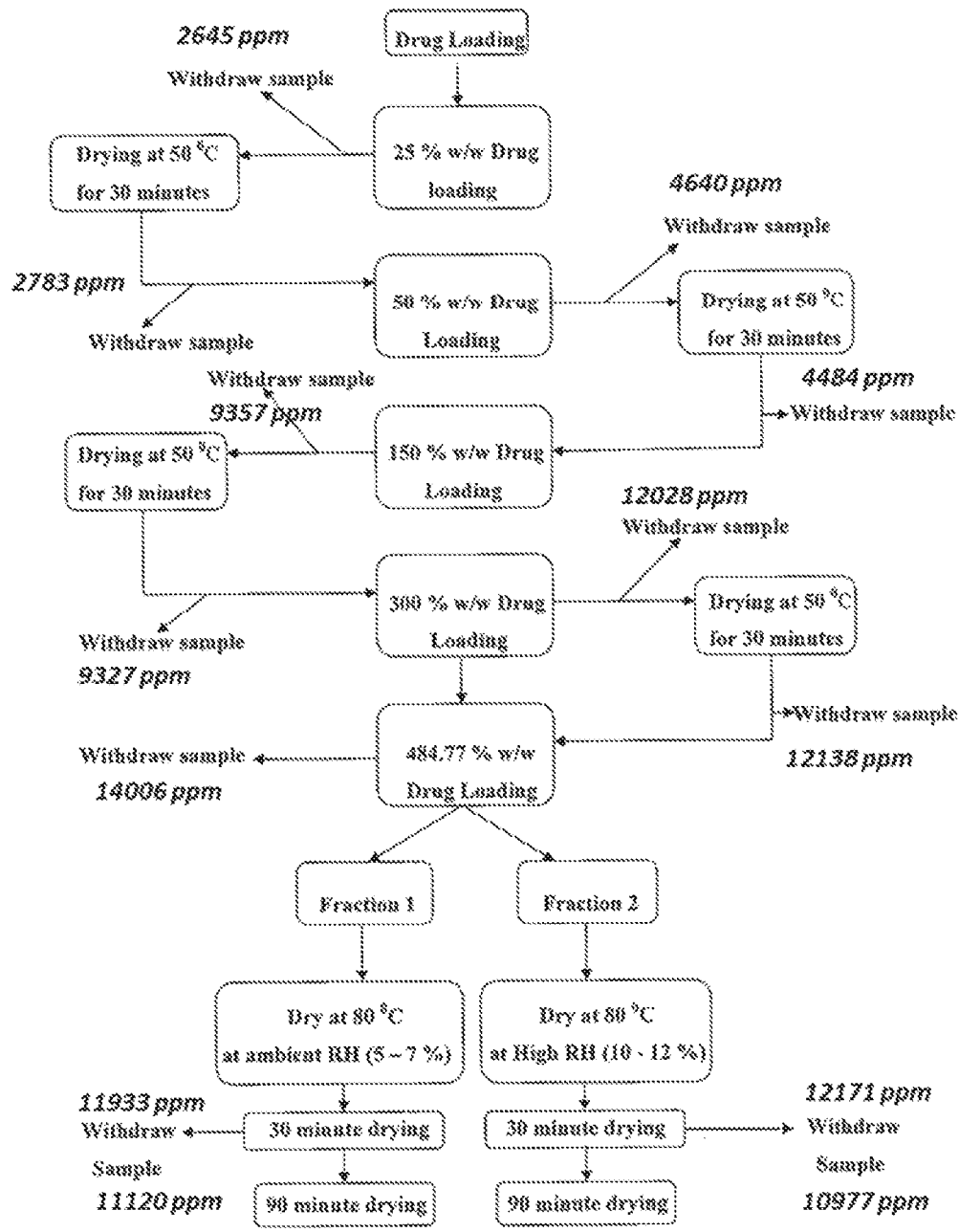
FIG. 5 is a schematic showing the isopropanol content at various points during drug-coating of pellets, using intermediate drying steps (Batch 167).
Figure 6:
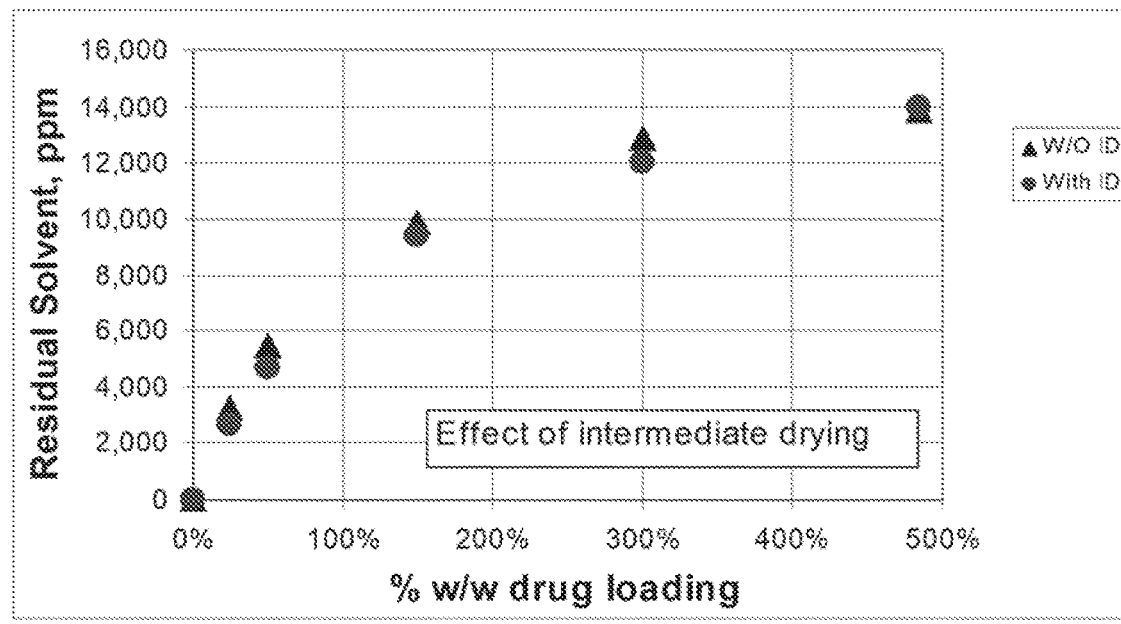
FIG. 6 is a graph demonstrating the effect of intermediate drying on the isopropanol content of drug-coated pellets.

Intermediate drying during drug coating: One approach that was tried to reduce residual solvent was drying the pellets at intermediate stages during the coating process. FIG. 4 presents a schematic of the control procedure for Batch 166, without intermediate drying, while FIG. 5 presents a schematic of intermediate drying procedure for Batch 167, in which the pellets were dried at four points during the drug-coating process. In these schematics, the amount of drug coating added is presented as % w/w compared to the initial weight of the uncoated pellets. At various points during these two procedures, samples were withdrawn and the amount of IPA present evaluated (ppm). The residual IPA present at different times during the intermediate drying process is presented in the schematics of FIG. 4 and FIG. 5, the graph of FIG. 6, and in Table 11 below.

Figure 7:
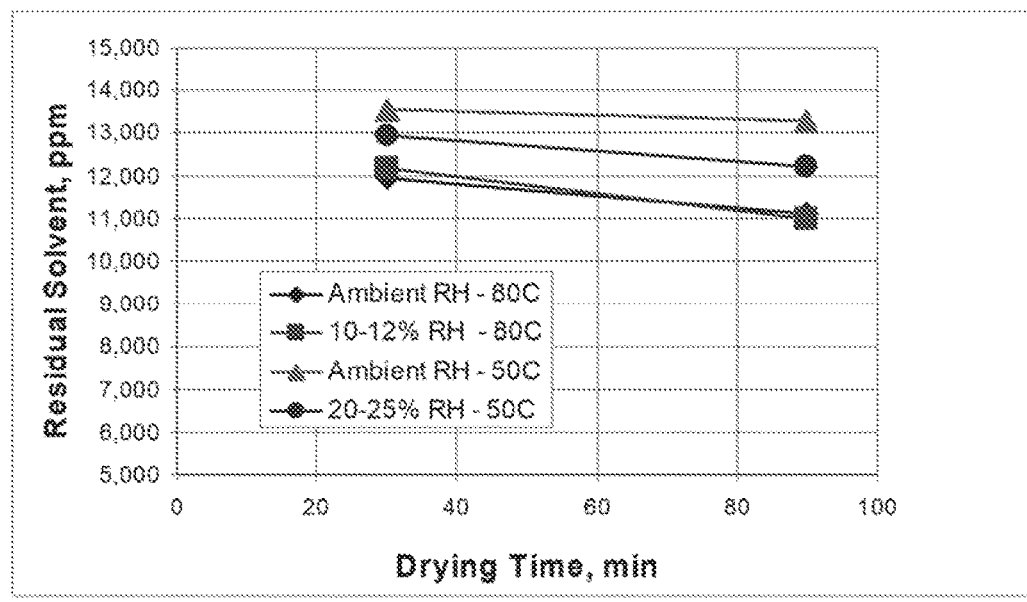
FIG. 7 is a graph demonstrating the effect of different drying conditions on the isopropanol content of drug-coated pellets.

Terminal drying of drug-coated pellets: Another approach that was attempted was to change the time, temperature, and/or humidity used when drying the fully coated pellets. Referring to FIG. 4 (the batch that did not go through intermediate drying), the fully coated pellets were divided into two fractions and dried at 50° C. at ambient or high humidity. Referring to FIG. 5 (intermediate drying), the fully coated pellets were divided into two fractions and dried at 50° C. at ambient or high humidity. Samples were taken at 30 or 90 minutes and the residual IPA evaluated (ppm). The effect of these different terminal drying procedures on the residual IPA level is presented in FIG. 7 and Table 11 below.

Increased temperature of drug coating product during coating: Table 11 also includes data from Batch 168, in which the temperature of the drug coating material was increased to 48-51° C. during the coating process.

TABLE 11

IPA content during and after drug coating

|  | Batch 166 | Batch 167 | Batch 168 |
|---|---|---|---|
| Product temperature (drug coating) | 38-42° C. | 38-42° C. | 48-51° C. |
| Intermittent drying | No | Yes | No |
| IPA Level | | | |
| 25% w/w drug coated, undried | 3258 ppm | 2645 ppm | — |
| 25% w/w drug coated, dried at 50° C. for 30 min | — | 2783 ppm | — |
| 50% w/w drug coated, undried | 5469 ppm | 4640 ppm | 3630 ppm |
| 50% w/w drug coated, dried at 50° C. for 30 min | — | 4484 ppm | — |
| 150% w/w drug coated, undried | 9862 ppm | 9357 ppm | 7338 ppm |
| 150% w/w drug coated, dried at 50° C. for 30 min | — | 9327 ppm | — |
| 300% w/w drug coated, undried | 12874 ppm | 12028 ppm | 8698 ppm |
| 300% w/w drug coated, dried at 50° C. for 30 min | — | 12138 ppm | — |
| 484.4% w/w drug coated, undried | 13857 ppm | 14006 ppm | 10158 ppm |
| 484.4% w/w drug coated, dried for 30 min at 50° C. at ambient RH | 13535 ppm | — | 9786 ppm |

In addition to evaluating IPA content at different points during and after the drug coating process as described above, the amount of IPA present was also evaluated in batches at different points after applying and drying the seal coating and the extended release coating. Table 12 summarizes these data.

TABLE 12

IPA content at each coating stage (At each stage, pooled sample before sieving was used)

| Stage | Drying Time | Batch 09-001 | Batch 9130 | Batch 9131 | Batch 9165 |
|---|---|---|---|---|---|
| Drug Coating | 0 min | — | 9924 ppm | 8587 ppm | 8201 ppm |
| | 30 min | — | 9523 ppm | 8814 ppm | 8057 ppm |
| | 60 min | 8746 ppm | 8607 ppm | 8705 ppm | 8376 ppm |
| Seal Coating | 0 min | — | 9943 ppm | 9454 ppm | 8929 ppm |
| | 30 min | 8746 ppm | 9782 ppm | 8832 ppm | 8992 ppm |
| | 60 min | 8397 ppm | 9151 ppm | 8220 ppm | 9757 ppm |
| Extended Release Coating | 0 min | 6653 ppm | 8026 ppm | 7814 ppm | — |
| | 30 min | 6385 ppm | 8019 ppm | 7705 ppm | — |
| | 60 min | 6273 ppm | 7863 ppm | 7882 ppm | 7191 ppm |

Example 9: Study to Assess the Efficacy and Safety of Amantadine HCl ER in MS Patients with Walking Impairment A 3-arm, multicenter, double-blind, placebo-controlled, randomized study will be used to assess the efficacy and safety of amantadine extended release capsules in Multiple Sclerosis patients with walking impairment. Approximately 570 subjects are to be enrolled in the Single-Blind Placebo Run-In Period to ensure that 540 subjects complete the Single-Blind Placebo Run-In Period and are eligible to be randomized into the Double-Blind Treatment Period. This study will be carried out using an extended release amantadine hydrochloride formulation with low residual organic solvent, similar to the one described in Example 2 (Type D).

Primary Objective:
   To evaluate the efficacy of 274 mg amantadine (as 340 mg amantadine HCl ER) in subjects with multiple sclerosis (MS) with walking impairment as measured by the Timed 25-foot Walk (T25FW, feet/second) at Week 16.

Secondary Objectives:
Key: To evaluate the efficacy of 274 mg amantadine (as 340 mg amantadine HCl ER) and 137 mg amantadine (as 170 mg amantadine HCl ER) in subjects with MS and walking impairment as measured by the T25FW, Timed Up and Go (TUG) test, and the 2-Minute Walk Test (2MWT) at Week 16.
Supportive: To evaluate the efficacy of the two dosages in subjects with MS and walking impairment as measured by the T25FW, the TUG, and the 2MWT across all study visits. To evaluate the efficacy in subjects with MS and walking impairment as measured by the Multiple Sclerosis Walking Scale-12 (MSWS-12).
Safety: To evaluate the safety and tolerability of the two dosages in subjects with MS and walking impairment.

Study Design: This will be a multicenter, 3-arm, randomized, placebo-controlled, double-blind, parallel-group study of amantadine extended release [ER] capsules in MS patients with walking impairment, incorporating a Single-Blind Placebo Run-In Period prior to randomization, and forced up-titration for the high-dose group. Eligibility for inclusion in this study will require all subjects to be on a stable medication regimen for at least 30 days prior to screening, and to continue the same dosing regimen for the duration of their study participation. Subjects may not have been treated with dalfampridine within 30 days prior to screening. Consented subjects who complete the up to 3-week screening period will undergo a 4-week Single-Blind Placebo Run-In Period during which subjects will receive placebo as 2 capsules once daily at bedtime. Subjects who complete the Single-Blind Placebo Run-In Period and continue to meet study eligibility criteria will be randomized with equal probability to 1 of 3 treatment groups: placebo or amantadine at 137 mg or 274 mg per dose (as 170 mg or 340 mg amantadine HCl, respectively). Study drugs will be administered as 2 capsules once daily at bedtime.

Subjects who are randomized to placebo will receive placebo capsules throughout the 12-week Double-Blind Treatment Period.

Subjects who are randomized to 137 mg amantadine will receive 137 mg of amantadine (as 170 mg amantadine HCl) throughout the Double-Blind Treatment Period.

Subjects who are randomized to 274 mg amantadine will receive 137 mg for the first week, 205.5 mg for the second week, and 274 mg for the remainder of the 12-week Double-Blind Treatment Period (as the equivalent amount of amantadine HCl).

During the Double-Blind Treatment Period, subjects will return to the clinic for safety and efficacy assessments at Weeks 6, 8, 12, and 16. In addition, telephone visits for safety assessments will be conducted at Weeks 5 and 7.

Subjects who complete the study through the Week 16 visit will be eligible to enter an optional open-label extension (OLE) study. Subjects who withdraw from the study prior to completion of the Week 16 visit will have an early termination visit that includes safety follow-up and efficacy assessments. Subjects who complete 12 weeks of double-blind treatment and elect not to participate in the OLE study will have a final post-treatment safety and efficacy assessment 2 weeks after their Week 16 visit. The end of study (EOS) is defined as when a subject completes the Week 16 visit (if electing to enter the OLE study) or the safety follow-up visit (if electing not to enter the OLE study).

All study visits and efficacy assessments should be scheduled to occur at approximately the same time of day for each individual subject. To the extent practicable, study visits and efficacy assessments should be scheduled to occur when a subject is not likely to be experiencing acute side effects from a concomitant medication (e.g., flu-like side effects following interferon-beta injection). Efficacy assessments should be conducted in following sequence: MSWS-12; T25FW; TUG; 2MWT. Subjects using an assistive device during the walking assessments at Screening should use the same assistive device for all subsequent walking tests. Each subject's efficacy assessment should be performed by the same clinical rater, if possible.

Adverse events (AEs) and concomitant medications will be recorded beginning with the first dose of study drug during the Single-Blind Placebo Run-In Period and continuing through the last study visit.

Inclusion Criteria:
1. Signed a current IRB-approved informed consent form
2. Male or female subjects between 18 and 70 years of age, inclusive, at the time of Screening
3. Confirmed diagnosis of MS according to the 2017 McDonald criteria (Thompson et al., 2017)
4. Current medication regimen must be stable for at least 30 days prior to screening, and subject must be willing to continue the same dosing regimen for the duration of study participation
5. Maximum Expanded Disability Status Scale (EDSS) score during screening of 6.5
6. Sufficient ambulatory ability (ambulatory aids acceptable if used consistently) to complete two trials of the Timed 25-Foot Walk (T25FW) at the screening visit, with the two trials completed within 5 minutes of each other in accordance with the specific instructions provided by the National MS Society Functional Composite Manual
7. Stable physical activity level (inclusive of prescribed physical therapy) for at least 30 days prior to screening and willing to continue without change for the duration of study participation A score on each of two completed screening T25FW tests between 8 and 45 seconds, inclusive Criteria:
1. Documented inability to tolerate amantadine
2. History of hypersensitivity or allergic reaction to amantadine, rimantadine, or memantine, or to any of the excipients used in the study drug capsules
3. Clinically significant MS relapse with onset less than 30 days prior to screening
4. Presence of neurologic dysfunction or medical condition, the severity of which, in the judgement of the investigator, would preclude the ability to perform walking tests safely
5. Receipt of systemic corticosteroids (intravenous [IV] or oral) or ACTHAR gel within 30 days prior to screening
6. Receipt of dalfampridine (or any 4-aminopyridine or 2,4-diaminopyridine preparation) or amantadine within 30 days prior to screening
7. History of other neurological or medical condition that, in the opinion of the investigator, would affect study outcome assessments
8. History of seizures within 3 years prior to screening
9. History of hallucinations (visual, auditory, or any other type) within 3 years prior to screening
10. History of bipolar disorder, schizophrenia, or psychosis, regardless of treatment 11. For subjects with a history of major depressive disorder, the presence of active depressive symptoms that, in the opinion of the investigator, would affect the subject's ability to complete study assessments, or which would not be in the subject's best interest to participate in the study
12. History of suicide attempt
13. History of suicidal ideation within 3 years of screening, or presence of suicidal ideation at screening, as detected by the Columbia Suicidality Scale (C-SSRS)
14. History of cognitive impairment sufficient, in the clinical judgement of the investigator, to affect the subject's ability to consent or complete study assessments, or to render it not in the subject's best interest to participate in the study
15. History of alcohol or substance dependence or abuse within 2 years prior to screening
16. History of stroke, transient ischemic attack (TIA), or myocardial infarction (MI) within 2 years prior to screening
17. History of cancer within 5 years prior to screening, with the following exceptions: adequately treated non-melanomatous skin cancers, localized bladder cancer, non-metastatic prostate cancer, in situ cervical cancer, or other definitively treated cancer that is considered cured
18. Presence of orthostatic hypotension at screening: a decrease in systolic blood pressure (at least 20 mm Hg) or diastolic blood pressure (at least 10 mm Hg) within 3 minutes of the subject standing up, compared to pressures obtained while sitting
19. Any laboratory test results outside of the central laboratory's normal range at screening that are assessed by the investigator to be clinically significant. Documentation by the investigator of clinical significance or insignificance must accompany out of range laboratory test results at screening
20. Aspartate aminotransferase (AST) and/or alanine aminotransferase (ALT) screening laboratory results>2 times the upper limit of normal
21. Estimated glomerular filtration rate (eGFR)<60 mL/min/1.73 m$^2$ (per Modification of Diet in Renal Disease [MDRD] calculation)
22. Inability to swallow oral capsules, or a history of gastrointestinal malabsorption that would preclude the use of oral medication
23. If female, is pregnant or lactating
24. If a sexually active female, is not surgically sterile or at least 2 years post-menopausal, or does not agree to utilize a highly effective hormonal method of contraception (an IUD, or vasectomized male partner is also acceptable), in combination with a barrier method, from screening through at least 4 weeks after the completion of study treatment. If a sexually active male, does not agree to utilize condoms from screening through at least 4 weeks after the completion of study treatment.
25. Received live attenuated influenza vaccine within 2 weeks prior to randomization or planning to receive live attenuated influenza vaccine during the duration of the study (amantadine may interfere with the efficacy of live attenuated vaccine)
26. Current treatment with medications that may affect urinary pH: carbonic anhydrase inhibitors, sodium bicarbonate, urinary acidification agents, quinine, quinidine, triamterene, or trimethoprim
27. Treatment with an investigational drug or device within 30 days prior to screening
28. Treatment with an investigational biologic within 6 months or 5 half-lives, whichever is longer, prior to screening
29. Current participation in another clinical trial
30. Prior or current participation in an Adamas clinical trial
31. Planned elective surgery, with the exception of minor dermatological procedures, during study participation Investigational Product, Dosage and Mode of Administration: All subjects are to continue their current (prior to screening visit) MS medications and regimens, without change, for the duration of their study participation, to the extent compatible with good neurological care. Consented subjects who complete screening and the Single-Blind Placebo Run-In Period and meet study eligibility criteria will be randomized with equal probability to 1 of 3 treatment groups: placebo, 137 mg amantadine (as 170 mg amantadine HCl), or 274 mg amantadine (as 340 amantadine HCl). Amantadine HCl ER capsules will be administered orally, as 2 capsules once daily at bedtime for the 12-week Double-Blind Treatment Period. The dosing regimens for the 2 active treatment arms are:

137 mg/d (1×137 mg capsule+1 placebo capsule) for 12 weeks for the 137 mg amantadine group (as corresponding amounts of amantadine HCl)

137 mg/d for 1 week (1×137 mg capsule+1 placebo capsule), followed by 205.5 mg/d (1×137 mg capsule+1×68.5 mg capsule) for 1 week, followed by 274 mg/d (2×137 mg capsules) for 10 weeks for the 274 mg amantadine group (as corresponding amounts of amantadine HCl)

Reference Therapy, Dosage and Mode of Administration: Placebo capsules (indistinguishable from amantadine capsules) will be administered orally as 2 capsules once daily at bedtime for the 4-week Single-Blind Placebo Run-In Period for all subjects and for the 12-week Double-Blind Treatment Period for subjects randomized to the placebo arm.

Duration of Treatment: Maximum duration of subject participation is up to approximately 21 weeks and will include a 3-week (maximum) screening period, 4-week Single-Blind Placebo Run-In Period, a 12-week Double-Blind Treatment Period for all subjects, and a 2-week post-treatment safety follow-up period for subjects who choose not to participate in the OLE study.

Criteria for Evaluation:
Primary Efficacy Measure: T25FW (measured in seconds but calculated to a feet/sec measurement)
Secondary Efficacy Measures: TUG (seconds), 2MWT (meters), and MSWS-12
Safety Measures: Adverse events (AEs), clinical laboratory evaluations (hematology, clinical chemistry, urinalysis, serum pregnancy tests for females of child bearing potential), vital signs, and Columbia-Suicide Severity Rating Scale (C-SSRS)

While certain embodiments of the present disclosure have been shown and described herein, such embodiments are provided by way of example only. Numerous variations, changes, and substitutions will now occur to those skilled in the art without departing from the disclosure. It should be understood that various alternatives to the embodiments of the disclosure described herein may be employed in practicing methods or preparing the compositions as described herein. All references cited herein are incorporated herein by reference in their entirety. Examples contained within US20110189273 and US20150087721, both to Went, are incorporated herein in their entirety.

What is claimed is:

1. A method of reducing levodopa-induced dyskinesia (LID) in a subject with Parkinson's disease in need thereof, comprising orally administering once daily to the subject an oral pharmaceutical composition comprising:
   a drug, wherein the drug is amantadine or a pharmaceutically acceptable salt thereof, and wherein said oral pharmaceutical composition comprises from 50 mg to 500 mg of the amantadine or an equivalent amount of the pharmaceutically acceptable salt thereof; and
   at least one excipient that modifies the release of at least a portion of said drug;
   wherein said oral pharmaceutical composition has a dissolution profile of said drug which shows (a) and/or (b):
   (a)
      (i) 0% to 10% in 2 hours, and
      (ii) 3% to 14% in 4 hours, and
      (iii) 23% to 40% in 6 hours, and
      (iv) not less than 80% in 12 hours;
   (b)
      (i) not more than 10% dissolution at 2 hours, and
      (ii) 5% to 13% dissolution at 4 hours, and
      (iii) 20% to 43% dissolution at 6 hours, and
      (iv) at least 80% dissolution at 12 hours;
      wherein the dissolution profile is determined with a USP Type 2 apparatus (paddles) at 50 rpm at 37.0±0.5° C. with 500 ml water as the dissolution medium; and
   wherein said oral pharmaceutical composition provides (i) a Tmax for amantadine of 11 to 19 hours, (ii) an $AUC_{0-inf}$ for amantadine of 44 to 72 ng*hr/ml per mg of said drug, and (iii) a $pAUC_{0-8}$ for amantadine of 1.0 to 2.0 ng*hr/ml per mg of said drug, when said oral pharmaceutical composition is dosed in healthy subjects of a single dose, human pharmacokinetic study, wherein the subjects are dosed in the morning after an overnight fast;
   wherein LID is reduced in the subject.

2. The method of claim 1, wherein reducing LID comprises reducing the severity of dyskinesia.

3. The method of claim 1, wherein the reduction of LID is evaluated with the Unified Dyskinesia Rating Scale (UDysRS).

4. A method of increasing ON time without troublesome dyskinesia in a subject with Parkinson's disease in need thereof, wherein the subject has levodopa-induced dyskinesia (LID), the method comprising orally administering once daily to the subject an oral pharmaceutical composition comprising
   a drug, wherein the drug is amantadine or a pharmaceutically acceptable salt thereof, and wherein said oral pharmaceutical composition comprises from 50 mg to 500 mg of the amantadine or an equivalent amount of the pharmaceutically acceptable salt thereof; and
   at least one excipient that modifies the release of at least a portion of said drug;
   wherein said oral pharmaceutical composition has a dissolution profile of said drug which shows (a) and/or (b):
   (a)
      (i) 0% to 10% in 2 hours, and
      (ii) 3% to 14% in 4 hours, and
      (iii) 23% to 40% in 6 hours, and
      (iv) not less than 80% in 12 hours;
   (b)
      (i) not more than 10% dissolution at 2 hours, and
      (ii) 5% to 13% dissolution at 4 hours, and
      (iii) 20% to 43% dissolution at 6 hours, and
      (iv) at least 80% dissolution at 12 hours;
      wherein the dissolution profile is determined with a USP Type 2 apparatus (paddles) at 50 rpm at 37.0±0.5° C. with 500 ml water as the dissolution medium; and
   wherein said oral pharmaceutical composition provides (i) a Tmax for amantadine of 11 to 19 hours, (ii) an $AUC_{0-inf}$ for amantadine of 44 to 72 ng*hr/ml per mg of said drug, and (iii) a $pAUC_{0-8}$ for amantadine of 1.0 to 2.0 ng*hr/ml per mg of said drug, when said oral pharmaceutical composition is dosed in healthy subjects of a single dose, human pharmacokinetic study, wherein the subjects are dosed in the morning after an overnight fast.

5. The method of claim 4, wherein the increase in ON time without troublesome dyskinesia is determined in a placebo controlled, double blind clinical study.

6. A method of reducing OFF time in a subject with Parkinson's disease in need thereof, wherein the subject has levodopa-induced dyskinesia (LID), the method comprising orally administering once daily to the subject an oral pharmaceutical composition comprising
   a drug, wherein the drug is amantadine or a pharmaceutically acceptable salt thereof, and wherein said oral pharmaceutical composition comprises from 50 mg to 500 mg of the amantadine or an equivalent amount of the pharmaceutically acceptable salt thereof; and
   at least one excipient that modifies the release of at least a portion of said drug;
   wherein said oral pharmaceutical composition has a dissolution profile of said drug which shows (a) and/or (b):
   (a)
      (i) 0% to 10% in 2 hours, and
      (ii) 3% to 14% in 4 hours, and
      (iii) 23% to 40% in 6 hours, and
      (iv) not less than 80% in 12 hours;
   (b)
      (i) not more than 10% dissolution at 2 hours, and
      (ii) 5% to 13% dissolution at 4 hours, and
      (iii) 20% to 43% dissolution at 6 hours, and
      (iv) at least 80% dissolution at 12 hours;
      wherein the dissolution profile is determined with a USP Type 2 apparatus (paddles) at 50 rpm at 37.0±0.5° C. with 500 ml water as the dissolution medium; and
   wherein said oral pharmaceutical composition provides (i) a Tmax for amantadine of 11 to 19 hours, (ii) an $AUC_{0-inf}$ for amantadine of 44 to 72 ng*hr/ml per mg of said drug, and (iii) a $pAUC_{0-8}$ for amantadine of 1.0 to 2.0 ng*hr/ml per mg of said drug, when said oral pharmaceutical composition is dosed in healthy subjects of a single dose, human pharmacokinetic study, wherein the subjects are dosed in the morning after an overnight fast;
   wherein OFF time is reduced in the subject.

7. The method of claim 6, wherein the increase in OFF time is determined in a placebo controlled, double blind clinical study.

8. The method of claim 1, wherein the oral pharmaceutical composition comprises from 100 mg to 450 mg of amantadine, or an equivalent amount of a pharmaceutically acceptable salt thereof.

9. The method of claim 1, wherein the oral pharmaceutical composition comprises one, two, three, or four unit dosage forms.

10. The method of claim 1, wherein the oral pharmaceutical composition comprises one or two unit dosage forms.

11. The method of claim 1, wherein the drug is a pharmaceutically acceptable salt of amantadine.

12. The method of claim 1, wherein the drug is amantadine hydrochloride.

13. The method of claim 1, wherein the oral pharmaceutical composition comprises less than 6000 ppm of organic solvent.

14. The method of claim 1, wherein the oral pharmaceutical composition comprises less than 2000 ppm of organic solvent.

15. The method of claim 1, wherein the oral pharmaceutical composition comprises:
   a plurality of coated pellets, wherein each coated pellet comprises amantadine or a pharmaceutically acceptable salt thereof; and
   a capsule shell.

16. The method of claim 15, wherein the plurality of coated pellets comprises less than 6000 ppm organic solvent.

17. The method of claim 4, wherein the oral pharmaceutical composition comprises from 100 mg to 450 mg of amantadine, or an equivalent amount of a pharmaceutically acceptable salt thereof.

18. The method of claim 4, wherein the oral pharmaceutical composition comprises one, two, three, or four unit dosage forms.

19. The method of claim 4, wherein the oral pharmaceutical composition comprises one or two unit dosage forms.

20. The method of claim 4, wherein the drug is a pharmaceutically acceptable salt of amantadine.

21. The method of claim 4, wherein the drug is amantadine hydrochloride.

22. The method of claim 4, wherein the oral pharmaceutical composition comprises less than 6000 ppm of organic solvent.

23. The method of claim 4, wherein the oral pharmaceutical composition comprises less than 2000 ppm of organic solvent.

24. The method of claim 4, wherein the oral pharmaceutical composition comprises:
   a plurality of coated pellets, wherein each coated pellet comprises amantadine or a pharmaceutically acceptable salt thereof; and
   a capsule shell.

25. The method of claim 24, wherein the plurality of coated pellets comprises less than 6000 ppm organic solvent.

26. The method of claim 6, wherein the oral pharmaceutical composition comprises from 100 mg to 450 mg of amantadine, or an equivalent amount of a pharmaceutically acceptable salt thereof.

27. The method of claim 6, wherein the oral pharmaceutical composition comprises one, two, three, or four unit dosage forms.

28. The method of claim 6, wherein the oral pharmaceutical composition comprises one or two unit dosage forms.

29. The method of claim 6, wherein the drug is a pharmaceutically acceptable salt of amantadine.

30. The method of claim 6, wherein the drug is amantadine hydrochloride.

31. The method of claim 6, wherein the oral pharmaceutical composition comprises less than 6000 ppm of organic solvent.

32. The method of claim 6, wherein the oral pharmaceutical composition comprises less than 2000 ppm of organic solvent.

33. The method of claim 6, wherein the oral pharmaceutical composition comprises:
   a plurality of coated pellets, wherein each coated pellet comprises amantadine or a pharmaceutically acceptable salt thereof; and
   a capsule shell.

34. The method of claim 33, wherein the plurality of coated pellets comprises less than 6000 ppm organic solvent.

* * * * *

UNITED STATES PATENT AND TRADEMARK OFFICE
CERTIFICATE OF CORRECTION

PATENT NO. : 12,233,033 B2
APPLICATION NO. : 17/339618
DATED : February 25, 2025
INVENTOR(S) : Gregory T. Went et al.

It is certified that error appears in the above-identified patent and that said Letters Patent is hereby corrected as shown below:

In the Claims

At Claim number 7, Column 98, Line number 56:
"The method of claim 6, wherein the increase in OFF"
Should read:
-- The method of claim 6, wherein the reduction in OFF --

Signed and Sealed this
Twenty-ninth Day of April, 2025

Coke Morgan Stewart
*Acting Director of the United States Patent and Trademark Office*